US012215377B2

(12) United States Patent
Fozouni et al.

(10) Patent No.: US 12,215,377 B2
(45) Date of Patent: Feb. 4, 2025

(54) HIV OR HCV DETECTION WITH CRISPR-CAS13A

(71) Applicants: The Regents of the University of California, Oakland, CA (US); The J. David Gladstone Institutes, a testamentary trust established under the Will of J. David Gladstone, San Francisco, CA (US)

(72) Inventors: Parinaz Fozouni, San Francisco, CA (US); Melanie Ott, Mill Valley, CA (US); Jennifer A. Doudna, Oakland, CA (US)

(73) Assignees: The J. David Gladstone Institute, a testamentary trust established under the Will of J. David Gladstone, San Francisco, CA (US); The Regents of the University of California, Oakland, CA (US)

( * ) Notice: Subject to any disclaimer, the term of this patent is extended or adjusted under 35 U.S.C. 154(b) by 943 days.

(21) Appl. No.: 17/273,752

(22) PCT Filed: Sep. 6, 2019

(86) PCT No.: PCT/US2019/049954
§ 371 (c)(1),
(2) Date: Mar. 5, 2021

(87) PCT Pub. No.: WO2020/051452
PCT Pub. Date: Mar. 12, 2020

(65) Prior Publication Data
US 2021/0348212 A1    Nov. 11, 2021

Related U.S. Application Data

(60) Provisional application No. 62/728,329, filed on Sep. 7, 2018.

(51) Int. Cl.
| | | |
|---|---|---|
| *C12Q 1/44* | (2006.01) | |
| *C12N 9/22* | (2006.01) | |
| *C12N 15/11* | (2006.01) | |
| *C12Q 1/68* | (2018.01) | |
| *C12Q 1/6806* | (2018.01) | |
| *C12Q 1/6876* | (2018.01) | |
| *C12Q 1/6888* | (2018.01) | |
| *C12Q 1/70* | (2006.01) | |

(52) U.S. Cl.
CPC ............ *C12Q 1/6806* (2013.01); *C12N 9/22* (2013.01); *C12N 15/11* (2013.01); *C12Q 1/6888* (2013.01); *C12Q 1/703* (2013.01); *C12N 2310/20* (2017.05); *C12Q 2600/158* (2013.01)

(58) Field of Classification Search
None
See application file for complete search history.

(56) References Cited

U.S. PATENT DOCUMENTS

| | | | | |
|---|---|---|---|---|
| 10,337,051 | B2 * | 7/2019 | Doudna | ............... C12Q 1/6823 |
| 11,459,599 | B2 * | 10/2022 | Doudna | ............... C12Q 1/6823 |
| 11,827,919 | B2 * | 11/2023 | Doudna | ............... C12Q 1/6823 |
| 11,840,725 | B2 * | 12/2023 | Doudna | ............... C12Q 1/6823 |
| 2008/0118494 | A1 | 5/2008 | Kutsch et al. | |
| 2009/0247570 | A1 | 10/2009 | Mayer | |
| 2014/0162894 | A1 | 6/2014 | Hatchwell et al. | |
| 2016/0281072 | A1 | 9/2016 | Zhang | |
| 2017/0321198 | A1 | 11/2017 | Severinov et al. | |
| 2017/0362644 | A1 | 12/2017 | Doudna et al. | |
| 2018/0208976 | A1 | 7/2018 | Doudna et al. | |

FOREIGN PATENT DOCUMENTS

| | | | | |
|---|---|---|---|---|
| WO | WO-2004024929 A2 | 3/2004 | | |
| WO | WO-2018107129 A1 * | 6/2018 | ............ | B01L 3/5023 |
| WO | WO-2020051452 A2 | 3/2020 | | |

OTHER PUBLICATIONS

Tsang et al., "Implementation and new insights in molecular diagnostics for HIV infection", Expert Rev. Mol. Diagnostics 18:433-441, Apr. 2018 (Year: 2018).*
Qin et al. "Rapid and Fully Microfluidic Ebola Virus Detection with CRISPRCas13a", ACS Sens. 4:1048-1054, Mar. 2019 (Year: 2019).*
"International Application Serial No. PCT/US2019/049954, International Search Report mailed Jan. 27, 2020", 5 pgs.
"International Application Serial No. PCT/US2019/049954, Invitation to Pay Add'l Fees and Partial Search Report mailed Nov. 13, 2019", 3 pgs.
"International Application Serial No. PCT/US2019/049954, Written Opinion mailed Jan. 27, 2020", 10 pgs.
"International Application Serial No. PCT US2019 049954, International Preliminary Report on Patentability mailed Mar. 18, 2021", 12 pgs.
"European Application Serial No. 19856752.1, Response to Communication pursuant to Rules 161(2) and 162 EPC filed Nov. 8, 2021", 19 pgs.
"European Application Serial No. 19856752.1, Response filed Mar. 9, 2023 to Extended European Search Report mailed Aug. 18, 2022", 30 pgs.
"European Application Serial No. 19856752.1, Partial Supplementary European Search Report mailed May 11, 2022", 14 ogs.
"European Application Serial No. 19856752.1, Extended European Search Report mailed Aug. 18, 2022", 11 pgs.

* cited by examiner

*Primary Examiner* — David Steadman
(74) *Attorney, Agent, or Firm* — Schwegman Lundberg & Woessner, P.A.

(57) ABSTRACT

The present disclosure relates to methods using CRISPR-Cas13a enzyme, complexed with HIV or HCV crRNAs to specifically and sensitively detect and quantify the presence of HIV or HCV RNA in a sample. These methods can be used to diagnose HIV or HCV infection, quantify the concentration of HIV or HCV RNA present in a sample, identify the presence of different HIV or HCV splice variants, subtypes, or mutations, and to monitor reactivation of HIV or HCV transcription.

19 Claims, 15 Drawing Sheets
Specification includes a Sequence Listing.

- GUIDE 1 = 3' LTR/POLYA TAIL(LAIRD R)
- GUIDE 2 = 3' LTR (LAIRD F)
- GUIDE 3 = 3' LTR (LAIRD PROBE)
- GUIDE 4 = TAT/REV EXON 1 (KS1)
- GUIDE 5 = TAT/REV EXON 1 (TAT1.4)
- GUIDE 6 = TAT/REV EXON 1 (TAT2/MF84)
- GUIDE 7 = TAT/REV EXON 2 (PROBE)
- GUIDE 8 = TAT/REV EXON 2 (REV/MF83)

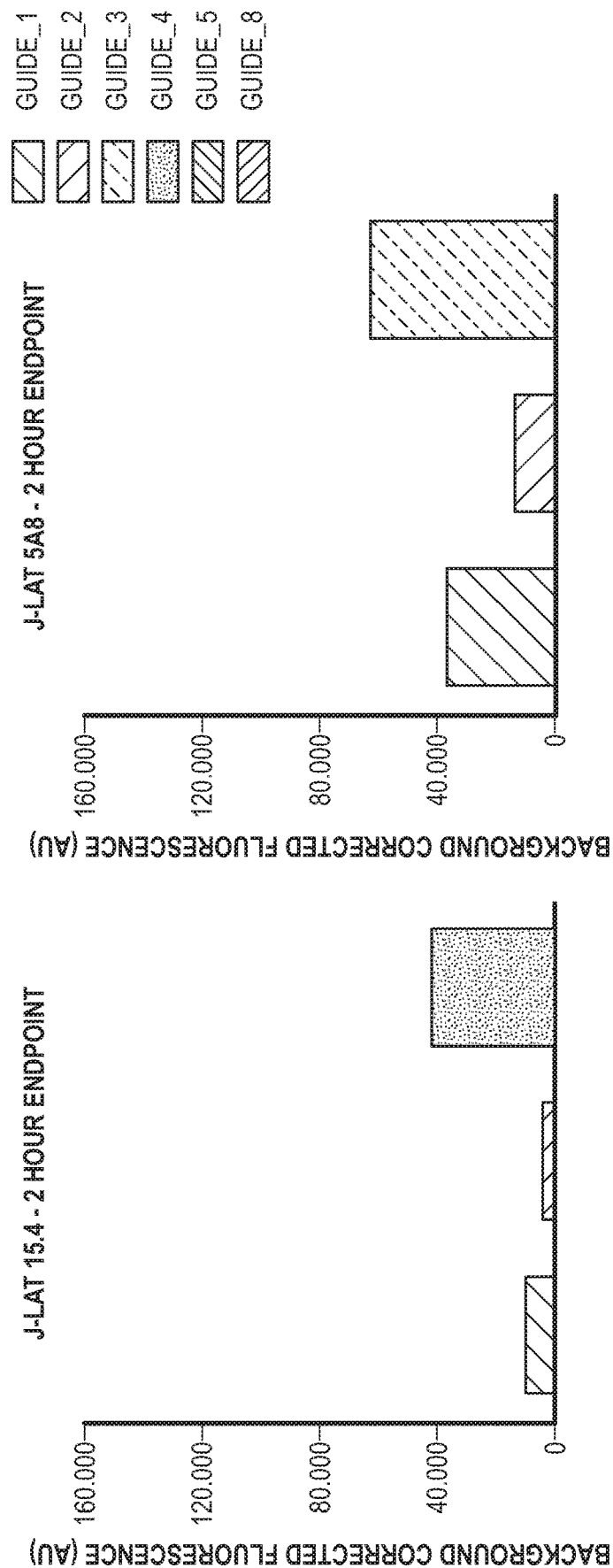

HIV OR HCV DETECTION WITH CRISPR-CAS13A

PRIORITY APPLICATIONS

This application is a U.S. National Stage Filing under 35 U.S.C. 371 from International Patent Application Serial No. PCT/US2019/049954, filed Sep. 6, 2019, published on Mar. 12, 2020 as WO 2020/051452 A2, which application claims benefit of priority to the filing date of U.S. Provisional Application Ser. No. 62/728,329, filed Sep. 7, 2018, the contents of which are specifically incorporated herein by reference in their entireties.

GOVERNMENT FUNDING

This invention was made with government support under DE R61 AI140465 awarded by the National Institutes of Health. The government has certain rights in the invention.

BACKGROUND

There are approximately 36.7 million people worldwide living with HIV/AIDS. It is estimated that 1.8 million new cases of HIV infection occurred in 2016, with about 5,000 new infections per day. In addition, currently only about 70% of people with HIV know of their positive status.

Accurate detection of acute and chronic HIV infections remains a significant challenge. Acute HIV-1 infection is the phase of HIV-1 disease immediately after infection and is characterized by detectable HIV-1 viremia or p24 antigen but having a yet undetectable antibody response. To date, all HIV self-testing products are serology-based, detecting antibodies to HIV-1 four weeks to three months, on average, after exposure. Some assays combine antibody detection with p24 antigen measurements, which allows HIV-1 detection as early as about 18 days after exposure but can have a detection window as large as between about 18 to 90 days. This remains a major detractor against HIV-1 self-testing, as self-tests with such a large window can provide false-negative results during acute infection, false reassurance, and can promote intercourse between discordant partners at the time of highest infectivity.

Early testing is currently laboratory-based and directed against nucleic acids of the viral genome (NAT), reliably detecting HIV-1 RNA about one week after exposure. Frequent NAT-based testing is required after treatment interruptions of chronically infected individuals who all present antibodies and are thus limited to NAT-based, not antibody-based, strategies and subject to frequent laboratory visits. Detection of viral RNA is the gold standard of HIV-1 diagnostics, but current state-of-the-art testing requires laboratory access and cannot be performed at home.

The United Nations has set targets to diagnose 90% of all people living with HIV-1 by 2020, however the World Health Organization (WHO) estimates that only 700% of people infected with HIV-1 currently know their HIV-1 status. As such, there is a critical need to develop new technologies for sensitive, easy-to-handle detection of HIV-1 that allows for frequent at-home testing.

The hepatitis C virus (which may be abbreviated as "HCV" hereinafter) was discovered as a major causative virus of non-A and non-B hepatitis. HCV is a single-stranded (+) RNA virus having a genome length of approximately 9.6 kb, in which the genome encodes a precursor protein that is divided into 10 types of virus protein (i.e., Core, E1, E2, p7, NS2, NS3, NS4A, NS4B, NS5A, and NS5B proteins) via post-translational cleavage by signal peptidase from host or proteases from HCV.

HCV is transmitted from human to human via blood, causing chronic hepatitis among about 60% to 80% of infected persons. When hepatitis is left without any appropriate treatment, it is known to cause cirrhosis or liver cancer within about 20 to 30 years after infection. Therefore, early detection of HCV infection for prevention of the onset of chronic hepatitis and early treatment of the disease after the onset thereof are desired.

SUMMARY

In some respects, this disclosure provides methods that include (a) incubating a sample containing RNA with a Cas13a protein and at least one CRISPR guide RNA (crRNA) for a period of time sufficient to form one or more HIV or HCV RNA cleavage product(s); and (b) detecting level(s) of HIV or HCV RNA cleavage product(s) with a detector, wherein the RNA is not reverse transcribed prior to the detecting step. Such methods are useful for detecting whether the sample contains one or more copies of an HIV or HCV RNA. The methods are also useful for detecting the absence of an HIV or HCV infection.

In some aspects the disclosure provides methods for quantifying HIV or HCV RNA concentration in a sample comprising (a) incubating a sample containing RNA with a Cas13a protein and at least one CRISPR guide RNA (crRNA) for a period of time sufficient to form one or more HIV or HCV RNA cleavage product(s); and (b) analyzing HIV or HCV RNA cleavage product quantity or concentration with a detector, wherein the RNA is not reverse transcribed prior to the detecting step.

In some aspects the disclosure provides methods for identifying the presence or absence of HIV or HCV splice variants and/or mutations in HIV or HCV RNA in a sample comprising (a) incubating a mixture comprising a sample containing RNA, a Cas13a protein, and at least one CRISPR guide RNA (crRNA) for a period of time sufficient to form one or more HIV or HCV RNA cleavage product(s); and (b) detecting any HIV or HCV splice variants and/or mutations in HIV or HCV RNA by analyzing any HIV or HCV RNA cleavage product(s) with a detector, wherein the RNA is not reverse transcribed prior to the detecting step.

In some aspects the disclosure provides methods for monitoring reactivation of HIV or HCV transcription comprising (a) incubating a sample containing RNA with a Cas13a protein and at least one CRISPR guide RNA (crRNA) for a period of time sufficient to form any RNA cleavage product(s); and (b) detecting any amount of HIV or HCV RNA cleavage product(s) in the sample with a detector. In some cases, the RNA in the sample is not reverse transcribed prior to the detecting step.

In some cases, the methods further comprise a step of amplification of RNA in the sample, or amplification of any HIV or HCV RNA cleavage products that may form. For example, the RNA can be amplified using an RNA-Dependent RNA polymerase or an RNA replicase (EC 2.7.7.48) that can replicate single-stranded RNA. Examples of such RNA replicases include the Qβ replicase, the RNA Polymerase from Rabbit Hemorrhagic Disease Virus (PDB: 1KHV); the RNA Polymerase from Sapporo Virus (PDB: 2CKW); the Hepatitis C RNA Polymerase (PDB: 2D41); the *Neurospora Crassa* RNA Polymerase (PDB: 2J7N); the RNA Polymerase Birnavirus (PDB: 2PGG); the RNA Polymerase from Infectious Bursal Disease Virus (PDB: 2PUS); the RNA Polymerase from Rotavirus (PDB: 2R7T); the RNA Polymerase from Infectious Pancreatic Necrosis Virus (PDB: 2YI8); the RNA Polymerase from Cypoviruses (PDB: 3JA4); the Enterovirus A RNA Polymerase (PDB: 3N6L); the RNA Polymerase from Norwalk Virus (PDB: 3UQS); the RNA Polymerase from Rotavirus A (PDB: 4AU6); the RNA Polymerase from Thosea Assigns Virus (PDB: 4XHA); the Rhinovirus A RNA polymerase (PDB: 1XR7); the Enterovirus C RNA polymerase (PDB: 3OL6); the Foot-and-Mouth Disease Virus RNA polymerase (PDB: 1U09); the Cardiovirus A RNA polymerase (PDB: 4NZ0); the Japanese Encephalitis Virus RNA polymerase (PDB: 4HDH); the Bovine Viral Diarrhea Virus 1 RNA polymerase (PDB: 1S48); the Qbeta Virus RNA polymerase (PDB: 3MMP); the Reovirus RNA polymerase (PDB: 1MUK); and the La Crosse Bunyavirus RNA polymerase.

In other cases, the RNA and/or the HIV or HCV RNA cleavage product(s) are not amplified.

In some embodiments, the detector is a fluorescence detector, optionally a short quenched-fluorescent RNA detector.

In some embodiments, the at least one HIV crRNA has a sequence such as any one of SEQ ID NO:1-8. In some embodiments, the sample is incubated with at least two, or at least three, or at least four, or at least five, or at least six, or at least seven, or at least eight, or at least nine, or at least nine, or at least ten, or more crRNAs.

In some embodiments, the HIV or HCV RNA cleavage product concentration is determined using a standard curve. In some embodiments, the HIV or HCV RNA cleavage product concentration is determined using a standard curve and comparing the detected level of the HIV or HCV RNA cleavage against the standard curve.

In some embodiments, the methods further comprise depleting a portion of the sample prior to other step(s) or inhibiting a nuclease in the sample prior to the other step(s). For example, the sample can be depleted of protein, enzymes, lipids, nucleic acids, or a combination thereof. In some embodiments, the depleted portion of the sample is a human nucleic acid portion.

In some embodiments, the methods further comprise removing ribonuclease(s)(RNase) from the sample. In some embodiments, the RNase is removed from the sample using an RNase inhibitor and/or heat.

In some embodiments, the Cas13a protein and/or the crRNA is lyophilized prior to incubation with the sample.

BRIEF DESCRIPTION OF THE DRAWINGS

Many aspects of the present disclosure can be better understood with reference to the following drawings. The components in the drawings are not necessarily to scale. Instead, emphasis is placed on illustrating clearly the principles of the present disclosure. Furthermore, components can be shown as transparent in certain views for clarity of illustration only and not to indicate that the illustrated component is necessarily transparent.

FIGS. 3A-3D demonstrate that not all crRNAs are equally effective.

DETAILED DESCRIPTION

Figure 1A:
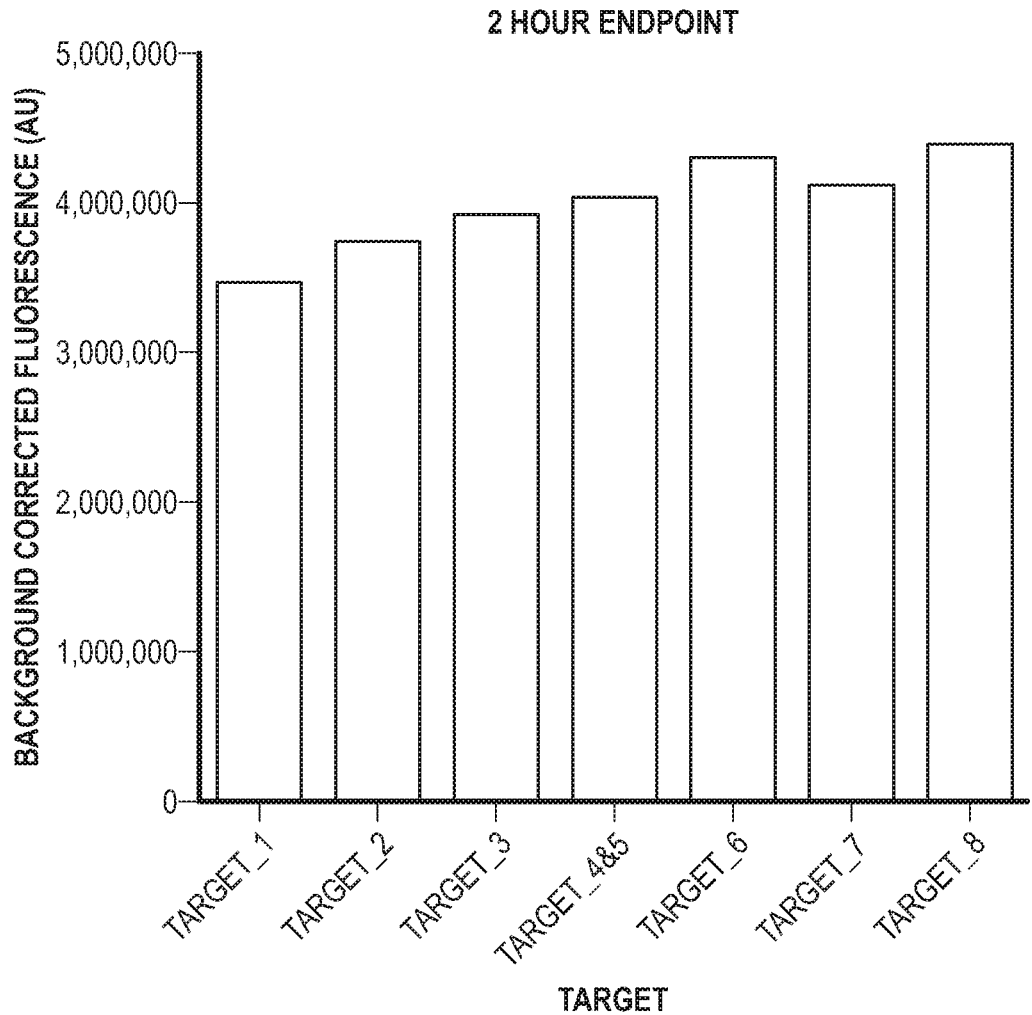
FIG. 1A demonstrates HIV CRISPR RNA (crRNA) can be used to detect corresponding HXB2 sequences.

While the present disclosure is capable of being embodied in various forms, the description below of several embodiments is made with the understanding that the present disclosure is to be considered as an exemplification of the invention and is not intended to limit the invention to the specific embodiments illustrated. Headings are provided for convenience only and are not to be construed to limit the invention in any manner. Embodiments illustrated under any heading may be combined with embodiments illustrated under any other heading.

All numerical designations, e.g., pH, temperature, time, concentration, and molecular weight, including ranges, are approximations which are varied (+) or (−) by increments of 0.1 or 1.0, where appropriate. It is to be understood, although not always explicitly stated that all numerical designations are preceded by the term "about." It also is to be understood, although not always explicitly stated, that the reagents described herein are merely exemplary and that in some cases equivalents may be available in the art.

It must be noted that as used herein and in the appended claims, the singular forms "a", "an", and "the" include plural referents unless the context clearly dictates otherwise. Thus, for example, reference to "a cell" includes a plurality of cells.

The term "about" when used before a numerical designation, e.g., temperature, time, amount, concentration, and such other, including a range, indicates approximations which may vary by (+) or (−) 20%, 10%, 5% or 1%.

Also, as used herein, "and/or" refers to and encompasses any and all possible combinations of one or more of the associated listed items, as well as the lack of combinations when interpreted in the alternative ("or").

The term "treatment" or "treating" in relation to a given disease or disorder, includes, but is not limited to, inhibiting the disease or disorder, for example, arresting the development of the disease or disorder; relieving the disease or disorder, for example, causing regression of the disease or disorder; or relieving a condition caused by or resulting from the disease or disorder, for example, relieving, preventing, or treating symptoms of the disease or disorder. The term "prevention" in relation to a given disease or disorder means: preventing the onset of disease development if none had occurred, preventing the disease or disorder from occurring in a subject that may be predisposed to the disorder or disease but has not yet been diagnosed as having the disorder or disease, and/or preventing further disease/disorder development or further disease/disorder progression if already present.

The present disclosure provides methods and compositions for diagnosing HIV or HCV infections, quantifying HIV or HCV RNA concentrations, identifying the presence of different HIV or HCV splice variants and/or mutations, and/or monitoring reactivation of HIV or HCV transcription.

Provided herein are methods and compositions for diagnosing HIV or HCV infection comprising incubating a mixture comprising a sample containing RNA, a Cas13a protein, and at least one CRISPR RNA (crRNA) for a period of time to form RNA cleavage products that may be present in the mixture and detecting a level of any such HIV or HCV RNA cleavage products with a detector.

Provided herein are methods and compositions for quantifying HIV or HCV RNA concentration comprising incubating a mixture comprising a sample, a Cas13a protein, and at least one CRISPR guide RNA (crRNA) for a period of time and analyzing the mixture with a detector to determine the concentration of any HIV or HCV RNA(s) that may be present in the mixture.

Provided herein are methods and compositions for identifying the presence or absence of different HIV or HCV splice variants and/or HIV or HCV mutations comprising incubating a mixture comprising a sample containing RNA, a Cas13a protein, and at least one CRISPR guide RNA (crRNA) for a period of time to form any RNA cleavage product(s) that may be present in the mixture, and detecting any different HIV or HCV splice variants and/or any different HIV or HCV mutations by analyzing any RNA cleavage product(s) with a detector, wherein the at least one crRNA recognizes the HIV or HCV splice variants and/or mutations.

Also provided herein are methods and compositions for monitoring reactivation of HIV or HCV transcription comprising incubating a mixture comprising a sample, a Cas13a protein, and at least one CRISPR guide RNA (crRNA) for a period of time and analyzing the mixture for the presence and/or amount of the RNA cleavage product with a detector.

In some aspects provided herein are methods for diagnosing the presence or absence of an HIV or HCV infection comprising incubating a mixture comprising a sample containing RNA, a Cas13a protein, and at least one CRISPR guide RNA (crRNA) for a period of time to form any RNA cleavage product(s) that may be present in the mixture; and detecting level(s) of HIV or HCV RNA cleavage product(s) that may be present in the mixture with a detector, wherein the RNA is not reverse transcribed prior to the detecting step. The presence or absence of an HIV or HCV infection in patient is detected by detecting level of HIV or HCV RNA cleavage product(s) that may be present in the mixture.

In some embodiments, the sample is isolated from a patient. Non-limiting examples of suitable samples include blood, serum, plasma, urine, aspirate, and biopsy samples. Thus, the term "sample" with respect to a patient encompasses blood and other liquid samples of biological origin, solid tissue samples such as a biopsy specimen or tissue cultures or cells derived therefrom and the progeny thereof. The definition also includes samples that have been manipulated in any way after their procurement, such as by treatment with reagents, washed, or enrichment for certain cell populations. The definition also includes sample that have been enriched for particular types of molecules, e.g., RNAs. The term "sample" encompasses biological samples such as a clinical sample such as blood, plasma, serum, aspirate, cerebral spinal fluid (CSF), and also includes tissue obtained by surgical resection, tissue obtained by biopsy, cells in culture, cell supernatants, cell lysates, tissue samples, organs, bone marrow, and the like. A "biological sample" includes biological fluids derived therefrom (e.g., infected cell, etc.), e.g., a sample comprising RNAs that is obtained from such cells (e.g., a cell lysate or other cell extract comprising RNAs). A sample can comprise, or can be obtained from, any of a variety of cells, tissues, organs, or acellular fluids.

In some embodiments, the sample is isolated from a patient known to have or suspected to have HIV. In other embodiments, the sample is isolated from a patient known to not have or suspected to not have HIV. In some embodiments, the HIV is HIV-1, including, for example, HIV-1 group M and HIV-1 group O. In other embodiments, the HIV is HIV-2.

In some embodiments, the sample is incubated with a Cas13a protein (previously known as C2c2). Cas13a binds and cleaves RNA substrates, rather than DNA substrates, which Cas9 can bind. Cas13a contains two HEPN domains for RNA cleavage, consistent with known roles for HEPN domains in other proteins. In some embodiments, the Cas13a proteins are from the following bacteria and/or have at least 75%, at least 80%, at least 85%, at least 90%, at least 95%, at least 98%, at least 99%, or 100% sequence identity to Cas13 in the following bacteria: *Leptotrichia wadei, Rhodobacter capsulatus, Herbinix hemicellulosilytica, Leptotrichia buccalis* (Lbu), *Listeria seeligeri, Paludibacter propionicigenes, Lachnospiraceae bacterium,* [*Eubacterium*] *rectale, Listeria newyorkensis, Clostridium aminophilum,* and/or *Leptotrichia shahii*.

For example, a *Leptotrichia wadei* Cas13a endonuclease can be used that has the following sequence (SEQ ID NO:10; National Center for Biotechnology Information (NCBI) accession no. WP_036059678.1).

```
  1 mkitkidgvs hykkqdkgil kkkwkdlder kqrekieary
 41 nkqieskiyk effrlknkkr iekeedqnik slyffikely
 81 lnekneewel kninleildd kervikgykf kedvyffkeg
121 ykeyylrilf nnliekvqne nrekvrknke fldlkeifkk
161 yknrkidlll ksinnnkinl eykkenvnee iygtnptndr
201 emtfyellke iiekkdeqks ileekldnfd itnfleniek
241 ifneeteini ikgkvlnelr eyikekeenn sdnklkqiyn
281 lelkkyienn fsykkqksks kngkndylyl nflkkimfie
321 evdekkeink ekfknkinsn fknlfvqkil dygkllyyke
361 ndeyikntgq letkdleyik tketlirkma vlvsfaansy
401 ynlfgrvsgd ilgtevvkss ktnvikvgsh ifkekmlnyf
441 fdfeifdank iveilesisy siynvrngvg hfnklilgky
481 kkkdintnkr ieedlnnnee ikgyfikkrg eierkvkekf
521 lsnnlqyyys kekienyfev yefeilkrki pfapnfkrii
561 kkgedlfnnk nnkkyeyfkn fdknsaeekk eflktrnfll
601 kelyynnfyk eflskkeefe kivlevkeek ksrgninnkk
641 sgvsfqsidd ydtkinisdy iasihkkeme rvekyneekq
681 kdtakyirdf veeifltgfi nylekdkrlh flkeefsilc
721 nnnnnvvdfn inineekike flkendsktl nlylffnmid
761 skrisefrne lvkykqftkk rldeekeflg ikielyetli
801 efviltrekl dtkkseeida wlvdklyvkd sneykeyeei
841 lklfvdekil sskeapyyat dnktpillsn fektrkygtq
881 sflseiqsny kyskvekeni edynkkeeie qkkksniekl
921 qdlkvelhkk weqnkiteke iekynnttrk ineynylknk
961 eelqnvyllh emlsdllarn vaffnkwerd fkfiviaikq
1001 flrendkekv neflnppdns kgkkvyfsvs kykntvenid
1041 gihknfmnli flnnkfmnrk idkmncaiwv yfrnyiahfl
1081 hlhtknekis lxsqmnllik lfsydkkvqn hilkstktll
1121 ekyniqinfe isndknevfk ykiknrlysk kgkmlgknnk
1161 lenefle nvkamleyse
```

Other sequences for *Leptotrichia wadei* Cas13a endonucleases are also available, such as those NCBI accession nos. BBM46759.1, BBM48616.1, BBM48974.1, BBM48975.1, and WP_021746003.1.

In another example, a *Herbinix hemicellulosilytica* Cas13a endonuclease can be used that has the following sequence (SEQ ID NO: 11, NCBI accession no. WP_103203632.1).

```
  1 MKLTRRRISG NSVDQKITAA FYRDMSQGLL YYDSEDNDCT
 41 DKVIESMDFE RSWRGRILKN GEDDKNPFYM FVKGLVGSND
 81 KIVCEPIDVD SDPDNLDILI NKNLTGFGRN LKAPDSNDTL
121 ENLIRKIQAG IPEEEVLPEL KKIKEMIQKD IVNRKEQLLK
161 SIKNNRIPFS LEGSKLVPST KKMKWLFKLI DVPNKTFNEK
201 MLEKYWEIYD YDKLKANITN RLDKTDKKAR SISRAVSEEL
241 REYHKNLRTN YNRFVSGDRP AAGLDNGGSA KYNPDKEEFL
281 LFLKEVEQYF KKYFPVKSKH SNKSKDKSLV DKYKNYCSYK
321 VVKKEVNRSI INQLVAGLIQ QGKLLYYFYY NDTWQEDFLN
361 SYGLSYIQVE EAFKKSVMTS LSWGINRLTS FFIDDSNTVK
401 FDDITTKKAK EAIESNYFNK LRTCSRMQDH FKEKLAFFYP
441 VYVKDKKDRP DDDIENLIVL VKNAIESVSY LRNRTFHFKE
481 SSLLELLKEL DDKNSGQNKI DYSVAAEFIK RDIENLYDVF
521 REQIRSLGIA EYYKADMISD CFKTCGLEFA LYSPKNSLMP
561 AFKNVYKRGA NLNKAYIRDK GPKETGDQGQ NSYKALEEYR
601 ELTWYIEVKN NDQSYNAYKN LLQLIYYKAF LPEVRENEAL
641 ITDFINRTKE WNRKETEERL NTKNNKKHKN FDENDDITVN
681 TYRYESIPDY QGESLDDYLK VLQRKQMARA KEVNEKEEGN
721 NNYIQFIRDV VVWAFGAYLE NKLKNYKNEL QPPLSKENIG
761 LNDTLKELFP EEKVKSPFNI KCRFSISTFI DNKGKSTDNT
801 SAEAVKTDGK EDEKDKKNIK RKDLLCFYLF LRLLDENEIC
841 KLQHQFIKYR CSLKERRFPG NRTKLEKETE LLAELEELME
881 LVRFTMPSIP EISAKAESGY DTMIKKYFKD FIEKKVFKNP
921 KTSNLYYHSD 5KTPVTRKYM ALLMRSAPLH LYKDIFKGYY
961 LITKKECLEY IKLSNIIKDY QNSLNELHEQ LERIKLKSEK
1001 QNGKDSLYLD KKDFYKVKEY VENLEQVARY KHLQHKINFE
1041 SLYRIFRIHV DIAARMVGYT QDWERDMHFL FKALVYNGVL
1081 EERRFEAIFN NNDDNNDGRI VKKIQNNLNN KNRELVSMLC
1121 WNKKLNKNEF GAIIWKRNPI AHLNHFTQTE QNSKSSLESL
1161 INSLRILLAY DRKRQNAVTK TINDLLLNDY HIRIKWEGRV
1201 DEGQIYFNIK EKEDIENEPI IHLKHLHKKD CYIYKNSYMF
1241 DKQKEWICNG IKEEVYDKSI LKCIGNLFKF DYEDKNKSSA
1281 NPKHT
```

For example, a *Leptotrichia buccalis* Cas13a endonuclease can be used that has the following sequence (SEQ ID NO:12; NCBI accession no. WP_015770004.1).

```
  1 MKVTKVGGIS HKKYTSEGRL VKSESEENRT DERLSALLNM
 41 RLDMYIKNPS STETKENQKR IGKLKKFFSN KMVYLKDNTL
 81 SLKNGKKENI DREYSETDIL ESDVRDKKNF AVLKKIYLNE
121 NVNSEELEVF RNDIKKKLNK INSLKYSFEK NKANYQKINE
161 NNIEKVEGKS KRNIIYDYYR ESAKRDAYVS NVKEAFDKLY
201 KEEDIAKLVL EIENLTKLEK YKIREFYHEI IGRKNDKENF
241 AKIIYEEIQN VNNMKELIEK VPDMSELKKS QVFYKYYLDK
281 EELNDKNIKY AFCHFVEIEM SQLLKNYVYK RLSNISNDKI
321 KRIFEYQNLK KLIENKLLNK LDTYVRNCGK YNYYLQDGEI
```

```
361  ATSDFIARNR QNEAFLRNII GV5SVAYFSL RNILETENEN

401  DITGRMRGKT VKNNKGEEKY VSGEVDKIYN ENKKNEVKEN

441  LKMFYSYDFN MDNKNEIEDF FANIDEAISS IRHGIVHFNL

481  ELEGKDIFAF KNIAPSEISK KMFQNEINEK KLKLKIFRQL

521  NSANVFRYLE KYKILNYLKR TRFEFVNKNI PFVPSFTKLY

561  SRIDDLKNSL GIYWKTPKTN DDNKTKEIID AQIYLLKNIY

601  YGEFLMYFMS NNGNFFEISK EIIELNKNDK RNLKTGFYKL

641  QKFEDIQEKI PKEYLANIQS LYMINAGNQD EEEKDTYIDF

681  IQKIFLKGFM TYLANNGRLS LIYIGSDEET NTSLAEKKQE

721  FDKFLKKYEQ NNNIKIPYEI NEFLREIKLG NILKYTERLN

761  MFYLILKLLN HKELTNLKGS LEKYQSANKE EAFSDQLELI

801  NLLNLDNNRV TEDFELEADE IGKFLDFNGN KVKDNKELKK

841  FDTMKIYFDG ENIIKHRAFY NIKKYGMLNL LEKIADKAGY

881  KISIEELKKY SNKKNEIEKN HKMQENLHRK YARPRKDEKF

921  TDEDYESYKQ AIENIEEYTH LKNKVEFNEL NLLQGLLLRI

961  LHRLVGYTSI WERDLRFRLK GEFPENQYIE EIFNFENKKN

1001 VKYKGGQIVE KYIKFYKELH QNDEVKINKY SSANIKVLKQ

1041 EKKDLYIRNY IAHFNYIPHA EISLLEVLEN LRKLLSYDRK

1081 LKNAVMKSVV DILKEYGFVA TFKIGADKKI GIQTLESEKI

1121 VHLKNLKKKK LMTDRNSEEL CKLVKIMFEY KMEEKKSEN
```

For example, a *Leptotrichia seeligeri* Cas13a endonuclease can be used that has the following sequence (SEQ ID NO:13; NCBI accession no. WP_012985477.1).

```
  1  MWISIKTLIH HLGVLFFCDY MYNRREKKII EVKTMRITKV

41  EVDRKKVLIS RDKNGGKLVY ENEMQDNTEQ IMHHKKSSFY

81  KSVVNKTICR PEQKQMKKLV HGLLQENSQE KIKVSDVTKL

121  NISNFLNHRF KKSLYYFPEN SPDKSEEYRI EINLSQLLED

161  SLKKQQGTFI CWESFSKDME LYIMWAENYI SSKTKLIKKS

201  IRNNRIQSTE SRSGQLMDRY MKDILNKNKP FDIQSVSEKY

241  QLEKLTSALK ATFKEAKKND KEINYKLKST LQNHERQIIE

281  ELKENSELNQ FNIEIRKHLE TYFPIKKTNR KVGDIRNLEI

321  GEIQKIVNHR LKNKIVQRIL QEGKLASYEI ESTVNSNSLQ

361  KIKIEEAFAL KFINACLFAS NNLRNMVYPV CKKDILMIGE

401  FKNSFKEIKH KKFIRQWSQF FSQEITVDDI ELASWGLRGA

441  IAPIRNEIIH LKKHSWKKFF NNPTFKVKKS KIINGKTKDV

481  TSEFLYKETL FKDYFYSELD SVPELIINKM ESSKILDYYS

521  SDQLNQVFTI PNFELSLLTS AVPFAPSFKR VYLKGFDYQN

561  QDEAQPDYNL KLNIYNEKAF NSEAFQAQYS LFKMVYYQVF

601  LPQFTTNNDL FKSSVDFILT LNKERKGYAK AFQDIRKMKK

641  DEKPSEYMSY IQSQLMLYQK KQEEKEKINH FEKFINQVFI

681  KGFNSFIEKN RLTYICHPTK NTVPENDNIE IPFHTDMDDS
```

```
721  NIAFWLMCKL LDAKQLSELR NEMIKFSCSL QSTEEISTFT

761  KAREVIGLAL LNGEKGCNDW KELFDDKEAW KKNMSLYVSE

801  ELLQSLPYTQ EDGQTPVINR SIDLVKKYGT ETILEKLFSS

841  SDDYKVSAKD IAKLHEYDVT EKIAQQESLH KQWIEKPGLA

881  RDSAWTKKYQ NVINDISNYQ WAKTKVELTQ VRHLHQLTID

921  LLSRLAGYMS IADRDFQFSS NYILERENSE YRVTSWILLS

961  ENKNKNKYND YELYNLKNAS IKVSSKNDPQ LKVDLKQLRL

1001 TLEYLELFDN RLKEKRNNIS HFNYLNGQLG NSILELFDDA

1041 RDVLSYDRKL KNAVSKSLKE ILSSHGMEVT FKPLYQTNHH

1081 LKIDKLQPKK IHHLGEKSTV SSNQVSNEYC QLVRTLLTMK
```

For example, a *Paludibacter propionicigenes* Cas13a endonuclease can be used that has the following sequence (SEQ ID NO:14; NCBI accession no. WP_013443710.1).

```
  1  MRVSKVKVKD GGKDKMVLVH RKTTGAQLVY SGQPVSNETS

41  NILPEKKRQS FDLSTLNKTI IKFDTAKKQK LNVDQYKIVE

81  KIFKYPKQEL PKQIKAEEIL PFLNHKFQEP VKYWKNGKEE

121  SFNLTLLIVE AVQAQDKRKL QPYYDWKTWY IQTKSDLLKK

161  SIENNRIDLT ENLSKRKKAL LAWETEFTAS GSIDLTHYHK

201  VYMTDVLCKM LQDVKPLTDD KGKINTNAYH RGLKKALQNH

241  QPAIFGTREV PNEANRADNQ LSIYHLEVVK YLEHYFPIKT

281  SKRRNTADDI AHYLKAQTLK TTIEKQLVNA IRANIIQQGK

321  TNHHELKADT TSNDLIRIKT NEAFVLNLTG TCAFAANNIR

361  NMVDNEQTND ILGKGDFIKS LLKDNTNSQL YSFFFGEGLS

401  TNKAEKETQL WGIRGAVQQI RNNVNHYKKD ALKTVFNISN

441  FENPTITDPK QQTNYADTIY KARFINELEK IPEAFAQQLK

481  TGGAVSYYTI ENLKSLLTTF QFSLCRSTIP FAPGFKKVFN

521  GGINYQNAKQ DESFYELMLE QYLRKENFAE ESYNARYFML

561  KLIYNNLFLP GFTTDRKAFA DSVGFVQMQN KKQAEKVNPR

601  KKEAYAFEAV RPMTAADSIA DYMAYVQSEL MQEQNKKEEK

641  VAEETRINFE KFVLQVFIKG FDSFLRAKEF DFVQMPQPQL

681  TATASNQQKA DKLNQLEASI TADCKLTPQY AKADDATHIA

721  FYVFCKLLDA AHLSNLRNEL IKFRESVNEF KFHHLLEIIE

761  ICLLSADVVP TDYRDLYSSE ADCLARLRPF IEQGADITNW

801  SDLFVQSDKH SPVIHANIEL SVKYGTTKLL EQIINKDTQF

841  KTTEANFTAW NTAQKSIEQL IKQREDHHEQ WVKAKNADDK

881  EKQERKREKS NFAQKFIEKH GDDYLDICDY INTYNWLDNK

921  MHFVHLMRLH GLTIELLGRM AGFVALFDRD FQFFDEQQIA

961  DEFKLHGFVN LHSIDKKLNE VPTKKIKEIY DIRNKIIQIN

1001 GNKINESVRA NLIQFISSKR NYYNNAFLHV SNDEIKEKQM

1041 YDIRNHIAHF NYLTKDAADF SLIDLINELR ELLHYDRKLK
```

```
1081 NAVSKAFIDL FDKHGMILKL KLNADHKLKV ESIEPKKIYH

1121 LGSSAKDKPE YQYCTNQVMM AYCNMCRSLL EMKK
```

For example, a *Lachnospiraceae bacterium* Cas13a endonuclease can be used that has the following sequence (SEQ ID NO: 15; NCBI accession no. WP_022785443.1).

```
   1 MKISKVREEN RGAKLTVNAK TAVVSENRSQ EGILYNDPSR

41 YGKSRKNDED RDRYIESRLK SSGKLYRIFN EDKNKRETDE

81 LQWFLSEIVK KINRRNGLVL SDMLSVDDRA FEKAFEKYAE

121 LSYTNRRNKV SGSPAFETCG VDAATAERLK GIISETNFIN

161 RIKNNIDNKV SEDIIDRIIA KYLKKSLCRE RVKRGLKKLL

201 MNAFDLPYSD PDIDVQRDFI DYVLEDFYHV RAKSQVSRSI

241 KNMNMPVQPE GDGKFAITVS KGGTESGNKR SAEKEAFKKF

281 LSDYAELDER VRDDMLRRMR RLVVLYFYGS DDSKLSDVNE

321 KFDVWEDHAA RRVDNREFIK LPLENKIANG KTDKDAERIR

361 KNTVKELYRN QNIGCYRQAV KAVEEDNNGR YFDDKMLNMF

401 FIHRIEYGVE KIYANLKQVT EFKARTGYLS EKIWKDLINY

441 ISIKYIAMGK AVYNYAMDEL NASDKKEIEL GKISEEYLSG

481 ISSFDYELIK AEEMLQRETA VYVAFAARHL SSQTVELDSE

521 NSDFILLKPK GTMDKNDKNX LASNNILNFL KDKETLRDTI

561 LQYFGGHSLW TDFPFDKYLA GGKDDVDFLT DLKDVIYSMR

601 NDSFHYATEN HNNGKWNKEL ISAMFEHETE RMTVVMKDKF

641 YSNNLPMFYK NDDLKKLLID LYKDNVERAS QVPSFNKVFV

681 RKNFPALVRD KDNLGIELDL KADADKGENE LKFYNALYYM

721 FKEIYYNAFL NDKNVRERFI TKATKVADNY DRNKERNLKD

761 RIKSAGSDEK KKLREQLQNY IAENDFGQRI KNIVQVNPDY

801 TLAQICQLIM TEYNQQNNGC MQKKSAARKD INKDSYQHYK

841 MLLLVNIRKA FLEFIKENYA FVLKPYKHDL CDKADFVPDF

881 AKYVKPYAGL ISRVAGSSEL QKWYIVSRFL SPAQANHMLG

921 FLHSYKQYVW DIYRRASETG TEINHSIAED KIAGVDITDV

961 DAVIDLSVKL CGTISSEISD YFKDDEVYAE YISSYLDFEY

1001 DGGNYKDSLN RFCNSDAVND QKVALYYDGE HPKLNRNIIL

1041 SKLYGERRFL EKITDRVSRS DIVEYYKLKK ETSQYQTKGI

1081 FDSEDEQKNI KKFQEMKNIV EFRDLMDYSE IADELQGQLI

1121 NWIYLRERDL MNFQLGYHYA CLNNDSNKQA TYVTLDYQGK

1161 KNRKINGAIL YQICAMYING LPLYYVDKDS SEWTVSDGKE

1201 STGAKIGEFY RYAKSFENTS DCYASGLEIF ENISEHDNIT

1241 ELRNYIEHFR YYSSFDRSFL GIYSEVFDRF FTYDLKYRKN

1281 VPTILYNILL QHFVNVRFEF VSGKKMIGID KKDRKIAKEK

1321 ECARITIREK NGVYSEQFTY KLKNGTVYVD ARDKRYLQSI

1361 IRLLFYPEKV NMDEMIEVKE KKKPSDNNTG KGYSKRDRQQ

1401 DRKEYDKYKE KKKKEGNFLS GMGGNINWDE INAQLKN
```

For example, a *Leptotrichia shahii* Cas13a endonuclease can be used that has the following sequence (SEQ ID NO: 16; NCBI accession no. BBM39911.1).

```
   1 MGNLFGHKRW YEVRDKKDFK IKRKVKVKRN YDGNKYILNI

41 NENNNKEKID NNKFIRKYIN YKKNDNILKE FTRKFHAGNI

81 LFKLKGKEGI IRIENNDDFL ETEEVVLYIE AYGKSEKLKA

121 LGITKKKIID EAIRQGITKD DKKIEIKRQE NEEEIEIDIR

161 DEYTNKTLND CSIILRIIEN DELETKKSIY EIFKNINMSL

201 YKIIEKIIEN ETEKVFENRY YEEHLREKLL KDDKIDVILT

241 NFMEIREKIK SNLEILGFVK FYLNVGGDKK KSKNKKMLVE

281 KILNINVDLT VEDIADFVIK ELEFWNITKR IEKVKKVNNE

321 FLEKRRNRTY IKSYVLLDKH EKFKIFRENK KDKIVKFFVE

361 NIKNNSIKEK IEKILAEFKI DELIKKLEKE LKKGNCDTEI

401 FGIFKKHYKV NFDSKKFSKK SDEEKELYKI IYRYLKGRIE

441 KILVNEQKVR LKKMEKIEIE KILNESILSE KILKRVKQYT

481 LEHIMYLGKL RHNDIDMTTV NTDDFSRLHA KEELDLELIT

521 FFASTNMELN KIFSRENINN DENIDFFGGD REKNYVLDKK

561 ILNSKIKIIR DLDFIDNKNN ITNNFIRKFT KIGTNERNRI

601 LHAISKERDL QGTQDDYNKV INIIQNLKIS DEEVSKALNL

641 DVVFKDKKNI ITKINDIKIS EENNNDIKYL PSFSKVLPEI

681 LNLYRNNPKN EPFDTIETEK IVLNALIYVN KELYKKLILE

721 DDLEENESKN IFLQELKKTL GNIDEIDENI IENYYKNAQI

761 SASKGNNKAI KKYQKKVIEC YIGYLRKNYE ELFDFSDFKM

801 NIQEIKKQIK DINDNKTYER ITVKTSDKTI VINDDFEYII

841 SIFALLNSNA VINKIRNRFF ATSVWLNTSF YQNIIDILDE

881 IMQLNTLRNE CITENWNLNL EEFIQKMKEI EKDFDDFKIQ

921 TKKEIFNNYY EDIKNNILTE FKDDINGCDV LEKKLEKIVI

961 FDDETKFEID KKSNILQDEQ RKLSNINKKD LKKKVDQYIK

1001 DKDQEIKSKI LCRIIFNSDF LKKYKKEIDN LIEDMESENE

1041 NKFQEIYYPK ERKNELYIYK KNLFLNIGNP NFDKIYGLIS

1081 NDIKMADAKF LFNIDGKNIR KNKISEIDAI LKNLNDKLNG

1121 YSKEYKEKYI KKLKENDDFF AKNIQNKNYK SFEKDYNRVS

1161 EYKKIRDLVE FNYLNKIESY LIDINWKLAI QMARFERDMH

1201 YIVNGLRELG IIKLSGYNTG ISRAYPKRNG SDGFYTTTAY

1241 YKFFDEESYK KFEKICYGFG IDLSENSEIN KPENESIRNY

1281 ISHFYIVRNP FADYSIAEQI DRVSNLLSYS TRYNNSTYAS

1321 VFEVFKKDVN LDYDELKKKF KLIGNNDILE RLMKPKKVSV

1361 LELESYNSDY IKNLIIELLT KIENTNDTL
```

In another example, a *Leptotrichia buccalis* C-1013-b Cas13a endonuclease can be used that has the following sequence (SEQ ID NO: 17, NCBI accession no. C7NBY4; AltName LbuC2c2).

```
  1 MKVTKVGGIS HKKYTSEGRL VKSESEENRT DERLSALLNM
 41 RLDMYIKNPS STETKENQKR IGKLKKFFSN KMVYLKDNTL
 81 SLKNGKKENI DREYSETDIL ESDVRDKKNF AVLKKIYLNE
121 NVNSEELEVF RNDIKKKLNK INSLKYSFEK NKANYQKINE
161 NNIEKVEGKS KRNIIYDYYR ESAKRDAYVS NVKEAFDKLY
201 KEEDIAKLVL EIENLTKIEK YKIREFYHEI IGRKNDKENF
241 AKIIYEEIQN VNNMKELIEK VPDMSELKKS QVFYKYYLDK
281 EELNDKNIKY AFCHFVEIEM SQLLKNYVYK RLSNISNDKI
321 KRIFEYQNLK KLIENKLLNK LDTYVRNCGK YNYYLQDGEI
361 ATSDFIARNR QNEAFLRNII GVSSVAYFSL RNILETENEN
401 DITGRMRGKT VKNNKGEEKY VSGEVDKIYN ENKKNEVKEN
441 LKMFYSYDEN MDNKNEIEDF FANIDEAISS IRHGIVHFNL
481 ELEGKDIFAF KNIAPSEISK KMFQNEINEK KLKLKIFRQL
521 NSANVFRYLE KYKILNYLKR TRFEFVNKNI PFVPSFTKLY
561 SRIDDLKNSL GIYWKTPKTN DDNKTKEIID AQIYLLKNIY
601 YGEFLNYFMS NNGNFFEISK EIIELNKNDK RNLKTGFYKL
641 QKFEDIQEKI PKEYLANIQS LYMINAGNQD EEEKDTYIDF
681 IQKIFLKGFM TYLANNGRLS LIYIGSDEET NTSLAEKKQE
721 FDKFLKKYEQ NNNIKIPYEI NEFLREIKLG NILKYTERLN
761 MFYLILKLLN HKELTNLKGS LEKYQSANKE EAFSDQLELI
801 NLLNLDNNRV TEDFELEADE IGKFLDFNGN KVKDNKELKK
841 FDTNKIYFDG ENIIKHRAFY NIKKYGMLNL LEKIADKAGY
881 KISIEELKKY SNKKNEIEKN HKMQENLHRK YARPRKDEKF
921 TDEDYESYKQ AIENIEEYTH LKNKVEFNEL NLLQGLLLRI
 961 LHRLVGYTSI WERDLRFRLK GEFPENQYIE EIFNFENKKN
1001 VKYKGGQIVE KYIKFYKELH QNDEVKINKY SSANIKVLKQ
1041 EKKDLYIRNY IAHFNYIPHA EISLLEVLEN LRKLLSYDRK
1081 LKNAVMKSVV DILKEYGFVA TFKIGADKKI GIQTLESEKI
1121 VHLKNLKKKK LMTDRNSEEL CKLVKIMFEY KMEEKKSEN
```

In some embodiments, the sample is incubated with at least one CRISPR RNA (crRNA) and the Cas13a protein. However, incubation of the crRNA and Cas13a protein without the sample is preferred, so that the crRNA and the Cas13a protein can form a complex. The sample RNA (e.g., HIV or HCV RNA) can then be added and act as an activating RNA. Once activated by complex formation with the activating RNA, the crRNA/Cas13a complex becomes a non-specific RNase to produce RNA cleavage products that can be detected using, for example, a short quenched-fluorescent RNA.

For example, the Cas13a and crRNA are incubated for a period of time to form the inactive complex. In some embodiments, the Cas13a and crRNA complexes are formed by incubating together at 37° C. for 30 minutes, 1 hour, or 2 hours (for example, 0.5 to 2 hours) to form an inactive complex. The inactive complex can then be incubated with the RNase Alert Substrate "Target" and complementary ssRNA activator (e.g., sample HIV or HCV RNA) so that the Cas13a/crRNA becomes an activated complex that cleaves in cis and trans. The at least one crRNA can bind to a region in the HIV RNA genome or in the HCV RNA genome. In some embodiments, the region is a single stranded region of the HIV or HCV RNA genome. In other embodiments, the region is a hairpin region of the HIV RNA or HCV genome.

In some embodiments, the at least one HIV crRNA is any one of SEQ ID NOs: 1-8. In some embodiments, the at least one crRNA has about 70%, about 75%, about 80%, about 85%, about 90%, about 95%, or more sequence identity to any one of SEQ ID NO 1-8. Table 1 provides examples of HIV crRNAs.

TABLE 1

Examples of HIV crRNA Sequences

| SEQ ID NO | Name | Sequence |
| --- | --- | --- |
| SEQ ID NO: 1 | PF001_crLbu_HXB2_1 | GACCACCCCAAAAAUGAAGGGGACUA AACUUUUUUUUUUUUGAAGCAC |
| SEQ ID NO: 2 | PF002_crLbu_HXB2_2 | GACCACCCCAAAAAUGAAGGGGACUA AAACCUGCUUAUAUGCAGGAUCUG |
| SEQ ID NO: 3 | PF003_crLbu_HXB2_3 | GACCACCCCAAAAAUGAAGGGGACUA AAACCCAGAGAGACCCAGUACAGG |
| SEQ ID NO: 4 | PF004_crLbu_HXB2_4 | GACCACCCCAAAAAUGAAGGGGACUA AAACCCUGCCAUAGGAGAUGCCUA |
| SEQ ID NO: 5 | PF005_crLbu_HXB2_5 | GACCACCCCAAAAAUGAAGGGGACUA AAACGUCUCCGCUUCUUCCUGCCA |
| SEQ ID NO: 6 | PF006_crLbu_HXB2_6 | GACCACCCCAAAAAUGAAGGGGACUA AAACAGCUUGAUGAGUCUGACUGU |
| SEQ ID NO: 7 | PF007_crLbu_HXB2_7 | GACCACCCCAAAAAUGAAGGGGACUA AAACUUCCUUCGGGCCUGUCGGGU |
| SEQ ID NO: 8 | PF008_crLbu_HXB2_8 | GACCACCCCAAAAAUGAAGGGGACUA AAACGGAUCUGUCUCUGUCUCUCU |

TABLE 1-continued

Examples of HIV crRNA Sequences

| SEQ ID NO | Name | Sequence |
|---|---|---|
| SEQ ID NO: 9 | Stem for all crRNAs | GACCACCCCAAAAAUGAAGGGGACUAAAAC |

In some embodiments, the at least one HCV crRNA is any one of SEQ ID NOs: 18-26. In some embodiments, the at least one crRNA has about 70%, about 75%, about 80%, about 85%, about 90%, about 95%, or more sequence identity to any one of SEQ ID NO: 18-26. Table 2 provides examples of HCV crRNAs.

TABLE 2

Examples of HCV crRNA Sequences

| SEQ ID NO: | Name | Sequence |
|---|---|---|
| 18 | PF016_crLbu_JFH1_1 | GACCACCCCAAAAAUGAAGGGGACUAAACGUGUACUCACCGGUUCCGCA |
| 19 | PF017_crLbu_JFH1_2 | GACCACCCCAAAAAUGAAGGGGACUAAACCCCUAUCAGGCAGUACCACA |
| 20 | PF018_crLbu_JFH1_3 | GACCACCCCAAAAAUGAAGGGGACUAAACACCGGGUAGGUUCCCUGUUG |
| 21 | PF019_crLbu_JFH1_4 | GACCACCCCAAAAAUGAAGGGGACUAAACGGGCGACCAGUUCAUCAUCA |
| 22 | PF020_crLbu_JFH1_5 | GACCACCCCAAAAAUGAAGGGGACUAAACGACGAUGACCUUCUUCUCCA |
| 23 | PF021_crLbu_JFH1_6 | GACCACCCCAAAAAUGAAGGGGACUAAACUUCCACUGCCAGUUGGAGCA |
| 24 | PF022_crLbu_JFH1_7 | GACCACCCCAAAAAUGAAGGGGACUAAACGUUCAUCCAUUGGACCGCGC |
| 25 | PF023_crLbu_JFH1_8 | GACCACCCCAAAAAUGAAGGGGACUAAACGGCUCGAGAAAGUCCAGAAC |
| 26 | PF024_crLbu_JFH1_9 | GACCACCCCAAAAAUGAAGGGGACUAAACUCUGCAGAGAGACCAGUUAC |

In some embodiments, the at least one crRNA recognizes the HIV or HCV splice variants and/or mutations.

In some embodiments, the sample is incubated with a single crRNA. In other embodiments, the sample is incubated with 2, 3, 4, 5, 6, 7, 8, 9, 10 or more crRNAs having a different sequence.

In some embodiments, the Cas13a protein and/or crRNA is lyophilized prior to incubation with the sample.

In some embodiments, the sample is incubated with the Cas13a protein and crRNA for a period of time sufficient to form RNA cleavage products. In some embodiments, the period of time is about 5 hours or less, about 4 hours or less, about 3 hours or less, about 2 hours or less, about 1.5 hours or less, about 1 hour or less, about 40 minutes or less, about 35 minutes or less, about 30 minutes or less, about 25 minutes or less, about 20 minutes or less, about 15 minutes or less, about 10 minutes or less, about 5 minutes or less, or about 1 minute or less.

In some embodiments, the RNA cleavage products (e.g., HIV or HCV RNA cleavage products) are detected using detector RNA using a fluorescence-emitting dye pair, i.e., a fluorescence resonance energy transfer (FRET) pair and/or a quencher/fluorophore pair.

In some embodiments, HIV or HCV RNA, and/or the RNA cleavage products (e.g., HIV or HCV RNA cleavage products) are present in the sample or the mixture along with non-target RNA (e.g., non-HIV RNA or non-HCV RNA). In some embodiments, the RNA cleavage products (e.g., HIV or HCV RNA cleavage products) are present at from about one copy per $10^{10}$ non-target RNAs (e.g., non-HIV or non-HCV RNAs) to about one copy per 10 non-target RNAs (e.g., non-HIV or non-HCV RNAs), at from about one copy per $10^9$ non-target RNAs (e.g., non-HIV RNA or non-HCV RNAs) to about one copy per $10^2$ non-target RNAs (e.g., non-HIV RNA or non-HCV RNAs), at from about one copy per $10^8$ non-target RNAs (e.g., non-HIV RNA or non-HCV RNAs) to about one copy per $10^3$ non-target RNAs (e.g., non-HIV RNA or non-HCV RNAs), at from about one copy per $10^7$ non-target RNAs (e.g., non-HIV RNA or non-HCV RNAs) to about one copy per $10^4$ non-target RNAs (e.g., non-HIV RNA or non-HCV RNAs), at from about one copy per $10^6$ non-target RNAs (e.g., non-HIV RNA or non-HCV RNAs) to about one copy per $10^5$ non-target RNAs (e.g., non-HIV RNA or non-HCV RNAs), at from about one copy per $10^{10}$ non-target RNAs (e.g., non-HIV RNAs or non-HCV RNAs) to about one copy per 100 non-target RNAs (e.g., non-HIV RNAs or non-HCV RNAs), at from about one copy per $10^9$ non-target RNAs (e.g., non-HIV RNAs or non-HCV RNAs) to about one copy per 100 non-target RNAs (e.g., non-HIV RNAs or non-HCV RNAs), at from about one copy per $10^8$ non-target RNAs (e.g., non-HIV RNAs or non-HCV RNAs) to about one copy per 100 non-target RNAs (e.g., non-HIV RNAs or non-HCV RNAs), at from about one copy per $10^7$ non-target RNAs (e.g., non-HIV RNA or non-HCV RNAs) to about one copy per 100 non-target RNAs (e.g., non-HIV RNAs or non-HCV RNAs), at from about one copy per $10^6$ non-target RNAs (e.g., non-HIV RNAs or non-HCV RNAs) to about one copy per 100 non-target RNAs (e.g., non-HIV RNAs or non-HCV RNAs), at from about one copy per $10^5$ non-target RNAs (e.g., non-HIV RNAs or non-HCV RNAs) to about one copy per 100 non-target RNAs (e.g., non-HIV RNAs or non-HCV RNAs), at from about one copy per $10^4$ non-target RNAs (e.g., non-HIV RNAs or non-HCV RNAs) to about one copy per 100 non-target RNAs (e.g., non-HIV RNAs or non-HCV RNAs), or at from about one copy per $10^3$ non-target RNAs (e.g., non-HIV RNAs or non-HCV RNAs) to about one copy per 100 non-target RNAs (e.g., non-HIV RNA or non-HCV RNAs).

In some embodiments, the methods described and disclosed herein can detect an amount of RNA cleavage products (e.g., HIV or HCV RNA cleavage products) in an amount of about 10 nM or less, about 5 nM or less, about 1 nM or less, about 0.5 nM or less, about 0.1 nM or less, about 0.05 nM or less, about 0.01 nM or less, about 0.005 nM or less, about 0.001 nM or less, about 0.0005 nM or less, about 0.0001 nM or less, about 0.00005 nM or less, or about 0.00001 nM or less. In some embodiments, the methods described and disclosed herein can detect an amount of RNA cleavage products (e.g., HIV or HCV RNA cleavage products) in an amount of about 10 pM or less, about 5 pM or less, about 1 pM or less, about 0.5 pM or less, about 0.1 pM or less, about 0.05 pM or less, about 0.01 pM or less, about 0.005 pM or less, about 0.001 pM or less, about 0.0005 pM or less, about 0.0001 pM or less, about 0.00005 pM or less, or about 0.00001 pM or less. In some embodiments, the methods described and disclosed herein can detect an amount of RNA cleavage products (e.g., HIV or HCV RNA cleavage products) in an amount of about 100 fM or less, about 50 fM or less, about 25 fM or less, about 20 fM or less, about 15 fM or less, about 10 fM or less, about 5 fM or less, or about 1 fM or less.

In some embodiments, the methods described and disclosed herein can detect an amount of RNA cleavage products (e.g., HIV or HCV RNA cleavage products) in an amount of about 1 fM or more, about 5 fM or more, about 10 fM or more, about 15 fM or more, about 20 fM or more, about 25 fM or more, about 50 fM or more, about 100 fM or more. In some embodiments, the methods described and disclosed herein can detect an amount of RNA cleavage products (e.g., HIV or HCV RNA cleavage products) in an amount of about 0.00001 pM or more, about 0.00005 pM or more, about 0.0001 pM or more, about 0.0005 pM or more, about 0.001 pM or more, about 0.005 pM or more, about 0.01 pM or more, about 0.05 pM or more, about 0.1 pM or more, about 0.5 pM or more, about 1 pM or more, about 5 pM or more, or about 10 pM or more. In some embodiments, the methods described and disclosed herein can detect an amount of RNA cleavage products (e.g., HIV or HCV RNA cleavage products) in an amount of about 0.00001 nM or more, about 0.00005 nM or more, about 0.0001 nM or more, about 0.0005 nM or more, about 0.001 nM or more, about 0.005 nM or more, about 0.01 nM or more, about 0.05 nM or more, about 0.1 nM or more, about 0.5 nM or more, about 1 nM or more, about 5 nM or more, or about 10 nM or more.

In some embodiments, the methods described and disclosed herein can detect an amount of RNA cleavage products (e.g., HIV or HCV RNA cleavage products) in an amount of from about $10^6$ nM to about 1 nM, from about $10^6$ nM to about $5 \times 10^6$ nM, from about $5 \times 10^6$ nM to about $10^5$ nM, from about $10^5$ nM to about $5 \times 10^5$ nM, from about $5 \times 10^5$ nM to about $10^4$ nM, from about $10^4$ nM to about $5 \times 10^4$ nM, from about $5 \times 10^4$ nM to about $10^3$ nM, from about $10^3$ nM to about $5 \times 10^3$ nM, from about $5 \times 10^3$ nM to about $10^2$ nM, from about $10^2$ nM to about $5 \times 10^2$ nM, from about $5 \times 10^2$ nM to about 0.1 nM, from about 0.1 nM to about 0.5 nM, from about 0.5 nM to about 1 nM, from about 1 nM to about 5 nM, or from about 5 nM to about 10 nM.

In some embodiments, the methods include detecting a level of the RNA cleavage product (e.g., HIV or HCV RNA cleavage products) with a detector. Detection of the RNA cleavage product can occur by any method known to one of skill in the art. Non-limiting examples of suitable detectors include gold nanoparticle-based detectors, fluorescence polarization, colloid phase transition/dispersion, electrochemical detection, semiconductor-based sensing, and detection of a labeled detector RNA. In some embodiments, the labeled detector is a fluorescence detector, optionally a short quenched-fluorescent RNA. The readout of such detectors can be any convenient readout, including mobile phone-based detectors, to read a measured amount of detectable fluorescent signal; a visual analysis of bands on a gel (e.g., bands that represent cleaved product versus uncleaved substrate), a visual or sensor based detection of the presence or absence of a color (i.e., color detection method), and the presence or absence of (or a particular amount of) an electrical signal.

In some embodiments, the RNA cleavage product concentration is determined using a standard curve and the level of the RNA cleavage product. In some embodiments, a standard curve can be created by running a series of different, known concentrations of "target" ssRNAs with complementarity to the crRNA(s) (that complex with Cas13a protein) and a reporter. Fluorescence can then be tracked over a period of time, for example, over about 10 minutes, over about 20 minutes, over about 30 minutes, over about 45 minutes, over about 1 hour, over about 2 hours, over about 3 hours, over about 4 hours, over about 5 hours, over about 6 hours, or more. In some embodiments, the fluorescence is tracked for over about 2 hours. The initial rate of each reaction is then determined and plotted to create a linear standard curve. In parallel, a sample of unknown concentration is also run. The initial rate of the fluorescence curve (e.g., 2-hour fluorescence curve) for the unknown sample is, for example, plotted on the standard curve to interpolate the concentration of HIV-1 RNA.

In some embodiments, the RNA is not reverse transcribed prior to the detecting step. In some embodiments, the methods further comprise comprising a step of amplification of the RNA and/or the RNA cleavage product. In other embodiments, the methods do not comprise comprising a step of amplification of the RNA and/or the RNA cleavage product. In some embodiments, the methods do not include reverse transcribing the RNA prior to the detecting step and do not amplify the RNA and/or RNA cleavage product.

In some embodiments, a portion of the sample or the reaction mixture is depleted prior to the detecting step. A non-limiting example of a suitable method for depletion is Depletion of Abundant Sequences by Hybridization (DASH) as described in US Publication No. 2018/0051320 which is incorporated by reference in its entirety. In some embodiments, the portion of the sample that is depleted is a human nucleic acid portion, for example human RNA.

In some embodiments, RNase is removed from the sample. In some embodiments, RNase is removed from the sample using an RNase inhibitor and/or heat.

Also described herein are kits that are useful for performing the methods detailed herein. Such kits can include a package that has at least one Cas13a protein, at least one CRISPR guide RNA (crRNA), and instructions for performing a method described herein, where each of the CRISPR guide RNA(s) can have a sequence with about 70%, about 75%, about 80%, about 85%, about 90%, about 95%, or more sequence identity to any one of SEQ ID NO: 1-8, 18-25 or 26. The kit can also contain at least one short quenched-fluorescent RNA.

The CRISPR guide RNAs (crRNAs) can be provided in an array where each crRNA is present within a well of a microarray or where each type of crRNA is attached to a discrete location on a solid surface. The crRNA(s) are supplied in a form that allows or facilitates complex formation with at least one Cas13a protein. Hence, any crRNAs are attached to a solid surface in a manner that does not interfere with complex formation with at least one Cas13a protein.

The kits can also include components such as nuclease-free water, a buffer to regulate the pH of a solution, reaction vessel(s), and/or implements for collection of a sample from a patient. Implements for collection of a sample can include at least one receptacle for a sample, at least one lancet, a capillary tube for collection of small samples (e.g., blood), at least one needle, at least one syringe, at least one alcohol swab, a nuclease inhibitor (e.g., an RNase inhibitor), at least one component for stabilizing the sample, or a combination thereof.

Optionally, the methods include a further step of treating HIV or HCV in subjects where HIV or HCV is detected or where monitored HIV or HCV levels have increased. Such a method can include administration of a therapeutic agent to a patient with detectable HIV or HCV.

Such treatment when HIV is detected can involve antiretroviral therapy (ART), combined antiretroviral therapy (cART), high active antiretroviral therapy (HAART), latency reversal agent(s) (LRAs), integrase strand transfer inhibitor (INSTI)-based regimens, regimens that include one or more boosted protease inhibitor active against HIV-2 (e.g., darunavir or lopinavir), or a combination of HIV therapeutic agents.

Such treatment when HCV is detected can, for example, involve administration of a therapeutic agent such as Daclatasir, Elbasvir-Grazoprevir, Glecaprevir-Pibrentasvir, Harvoni, Ledipasvir-Sofosbuvir, Ombitasvir-Paritaprevir-Ritonavir, Ombitasvir-Paritaprevir-Ritonavir and Dasabuvir, Peginterferon alfa-2a, Peginterferon alfa-2b, Ribavirin, Simeprevir, Sofosbuvir, Technivie, Sofosbuvir-Velpatasvir, Sofosbuvir-Velpatasvir-Voxilaprevir, Zepatier, or combinations thereof.

In some embodiments, the kits described herein can also include a therapeutic agent for treatment of HIV or HCV.

EXAMPLES

Example 1: Validation of Cas13a Detection of HIV Transcripts

Figure 1B:
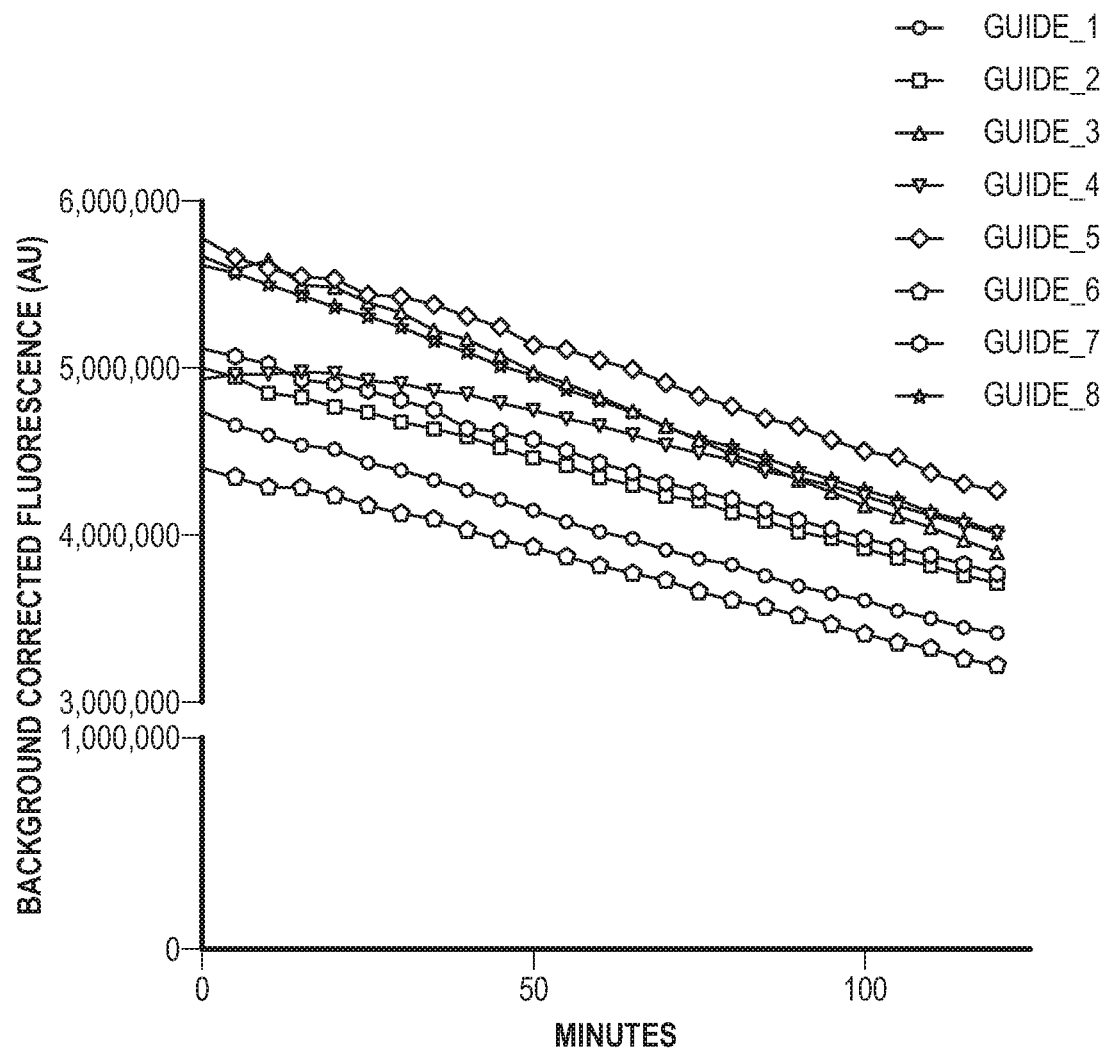
FIG. 1B demonstrates HIV crRNAs can be used to detect corresponding HXB2 targets over time.

CRISPR RNA guides (crRNAs) were designed and validated for HIV. Eight crRNAs were designed with 20-nt spacers corresponding to TILDA (tat/rev) & Laird et al. (J. Clin Invest 125(5): 1901-1912 (2015))(3'LTR/polyA tail). Each crRNA includes a crRNA stem that is derived from a bacterial sequence, while the spacer sequence is derived from the HIV genome (reverse complement). See Table 1 (reproduced below) for crRNA sequences. The crRNAs were validated against 50 nucleotide ssRNAs spanning corresponding portions of the HXB2 genome. Results demonstrated that the HIV crRNAs detected their corresponding HXB2 "activators" and HXB2 targets, as illustrated in FIGS. 1A and 1B.

TABLE 1

Examples of HIV crRNA Sequences

| SEQ ID NO | Name | Sequence |
| --- | --- | --- |
| SEQ ID NO: 1 | PF001_crLbu_HXB2_1 | GACCACCCCAAAAAUGAAGGGGACUA AACUUUUUUUUUUUUUGAAGCAC |
| SEQ ID NO: 2 | PF002_crLbu_HXB2_2 | GACCACCCCAAAAAUGAAGGGGACUA AAACCUGCUUAUAUGCAGGAUCUG |
| SEQ ID NO: 3 | PF003_crLbu_HXB2_3 | GACCACCCCAAAAAUGAAGGGGACUA AAACCCAGAGAGACCCAGUACAGG |
| SEQ ID NO: 4 | PF004_crLbu_HXB2_4 | GACCACCCCAAAAAUGAAGGGGACUA AAACCCUGCCAUAGGAGAUGCCUA |
| SEQ ID NO: 5 | PF005_crLbu_HXB2_5 | GACCACCCCAAAAAUGAAGGGGACUA AAACGUCUCCGCUUCUUCCUGCCA |
| SEQ ID NO: 6 | PF006_crLbu_HXB2_6 | GACCACCCCAAAAAUGAAGGGGACUA AAACAGCUUGAUGAGUCUGACUGU |
| SEQ ID NO: 7 | PF007_crLbu_HXB2_7 | GACCACCCCAAAAAUGAAGGGGACUA AAACUUCCUUCGGGCCUGUCGGGU |
| SEQ ID NO: 8 | PF008_crLbu_HXB2_8 | GACCACCCCAAAAAUGAAGGGGACUA AAACGGAUCUGUCUCUGUCUCUCU |
| SEQ ID NO: 9 | Stem for all crRNAs | GACCACCCCAAAAAUGAAGGGGACUA AAAC |

The crRNAs were then tested using several HIV cell lines. Briefly, crRNAs were diluted to 28 pM in TE buffer, pH 8. Activator ssRNA targets were prepared at 100 pM in TE buffer, pH 8. In some experiments, RNA from J-Lat cells (e.g., NIH AIDS Reagent Program catalog #9849) was used as the activator ssRNA target. J-Lat cells are Jurkat-derived human T cells that are latently infected with the packaged retroviral construct HIV-R7/E-/GFP, which is full length HIV-1 minus env, minus nef J-Lat RNA was calculated to 325 ng in 0.65 μL water containing diethyl pyrocarbonate (DEPC water). A complex master mix was made by mixing 5× buffer, DEPC water, and crRNA, which was then combined with Cas13a protein. Controls without Cas13a protein were also made. The complex master mixes were then incubated at 37° C. for 30-60 minutes. DEPC water was added to lyophilized RNaseAlert (ThermoFisher Scientific) to resuspend. Target mixes were then made by adding RNase Alert, DEPC water, and 5× buffer to individually aliquoted HIV RNA activator samples. Five μL of target mix was added to each well of a 384-well plate along with 15 μL of appropriate complex master mix. The formation of RNA cleavage products was monitored with a fluorometer.

Figure 2:
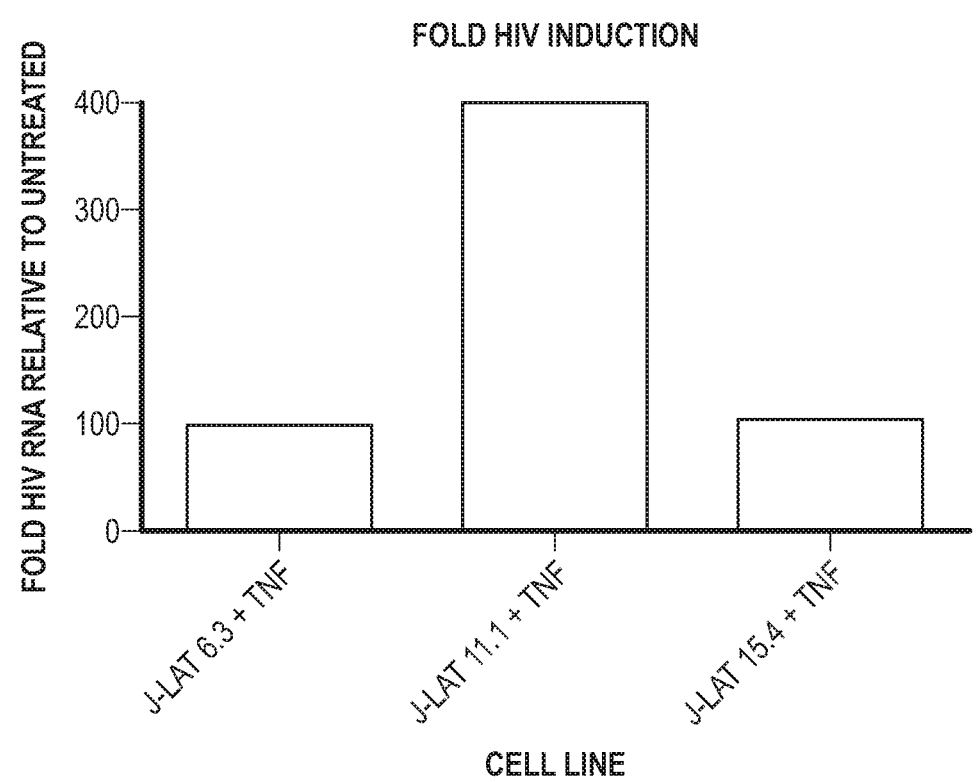
FIG. 2 demonstrates reactivation of multiple HIV cell lines using RNA isolated from J-Lat cells activated with TNF-α detected by qPCR.

Multiple HIV cell lines were reactivated with tumor necrosis factor alpha (TNF-α). FIG. 2 illustrate the amount of reactivated HIV detected by determining the amount of HIV RNA in the different reaction mixtures.

Figure 3B:
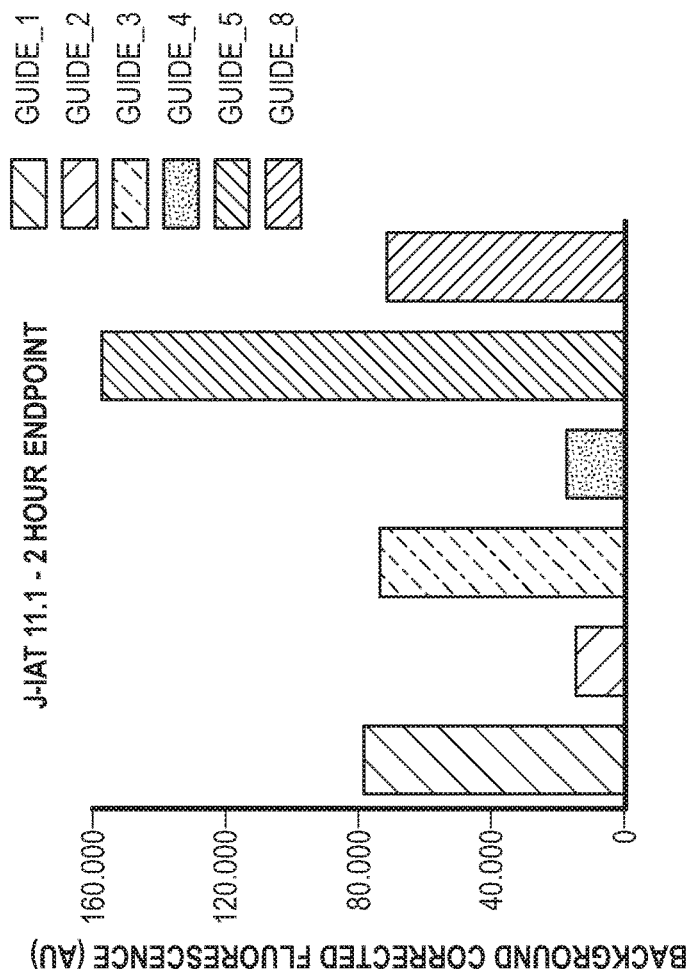
Figure 3A:
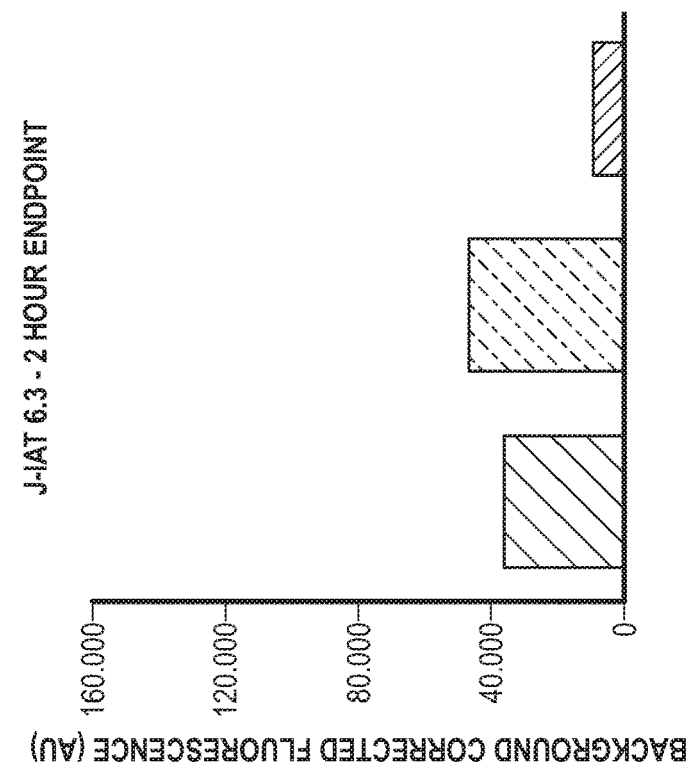
Figure 4:
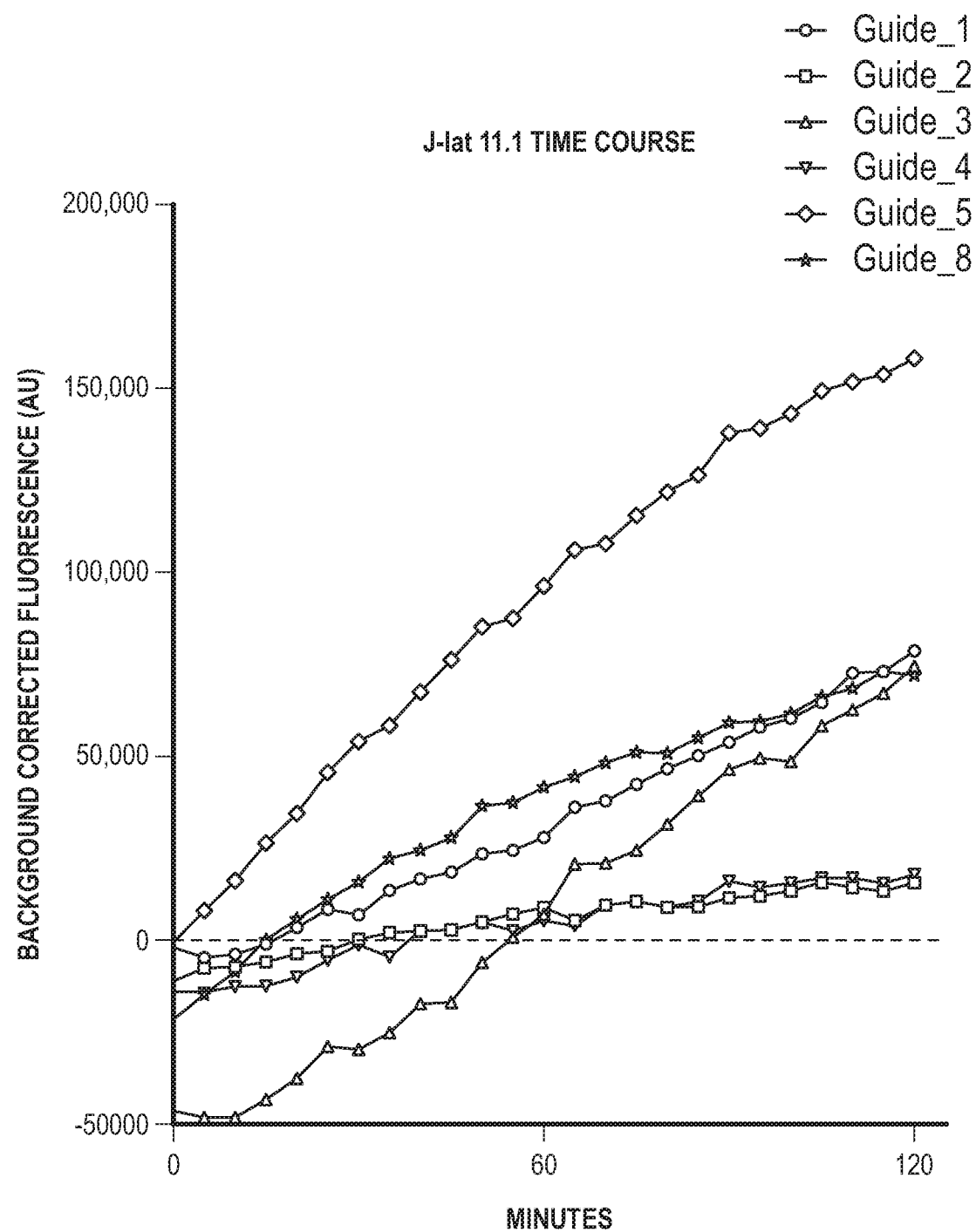
FIG. 4 demonstrates that not all crRNAs are equally effective overtime.

Further experimental results showed that "accessible" regions of HIV RNA are most favorable targets for crRNA: HIV RNA binding. Both cell-associated RNA (J-Lat cell lines) and supernatant RNA (ACH-2 & U-1 cell lines) were evaluated. Using RNase A, maximum signals can be detected. Importantly, not all crRNAs were equally effective as illustrated in FIGS. 3A-3D. FIG. 4 shows same data as FIG. 3B, plotted over time.

Figure 6:
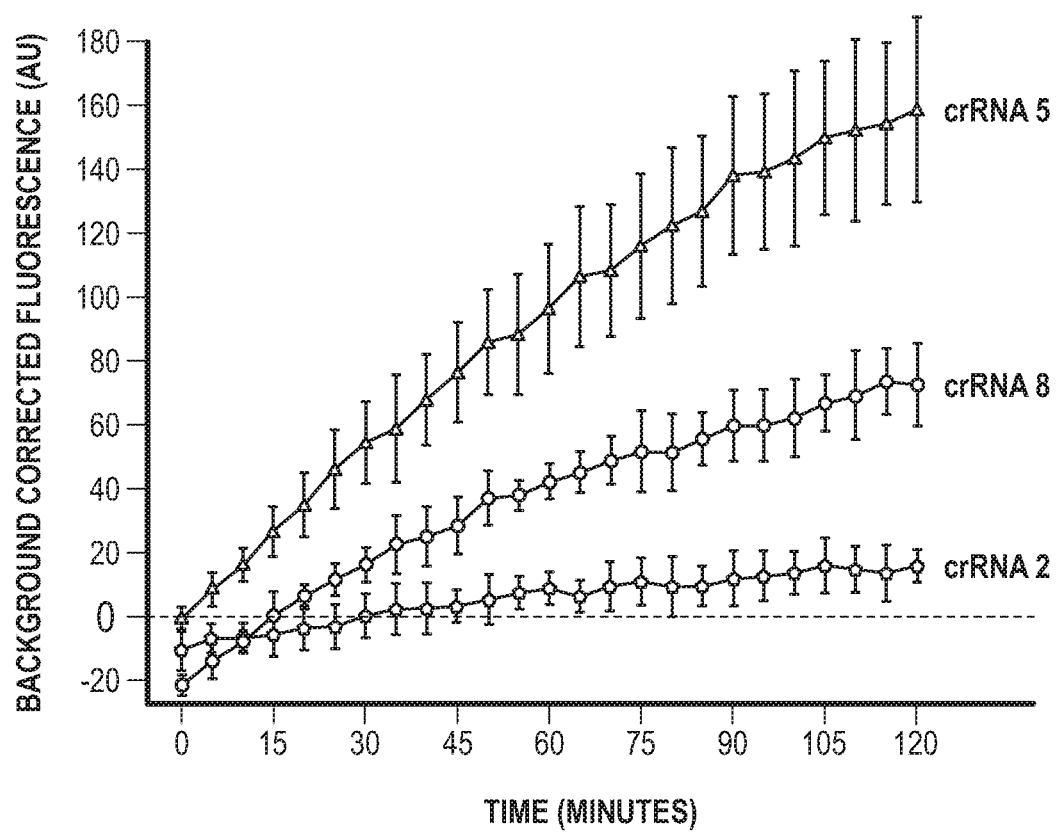
FIG. 6 shows specific detection of HIV-1 RNA with Cas13a:crRNA complexes and RNaseAlert detection reagent. Three different crRNAs were tested in total RNAs isolated from J-Lat 11.1 cells reactivated with TNFα (10 ng/ml). Shown are means SD of three replicate measurements of one RNA sample. Fluorescence values are $\times 10^3$.

FIG. 6 shows specific detection of HIV-1 RNA with Cas13a:crRNA complexes and RNaseAlert detection reagent using three different crRNAs. The crRNAs were tested with total RNAs isolated from J-Lat 11.1 cells reactivated with TNFα (10 ng/ml). As illustrated, different crRNAs provide somewhat different results, indicating that different crRNA may have more or less access to the HIV RNA.

Figure 5:
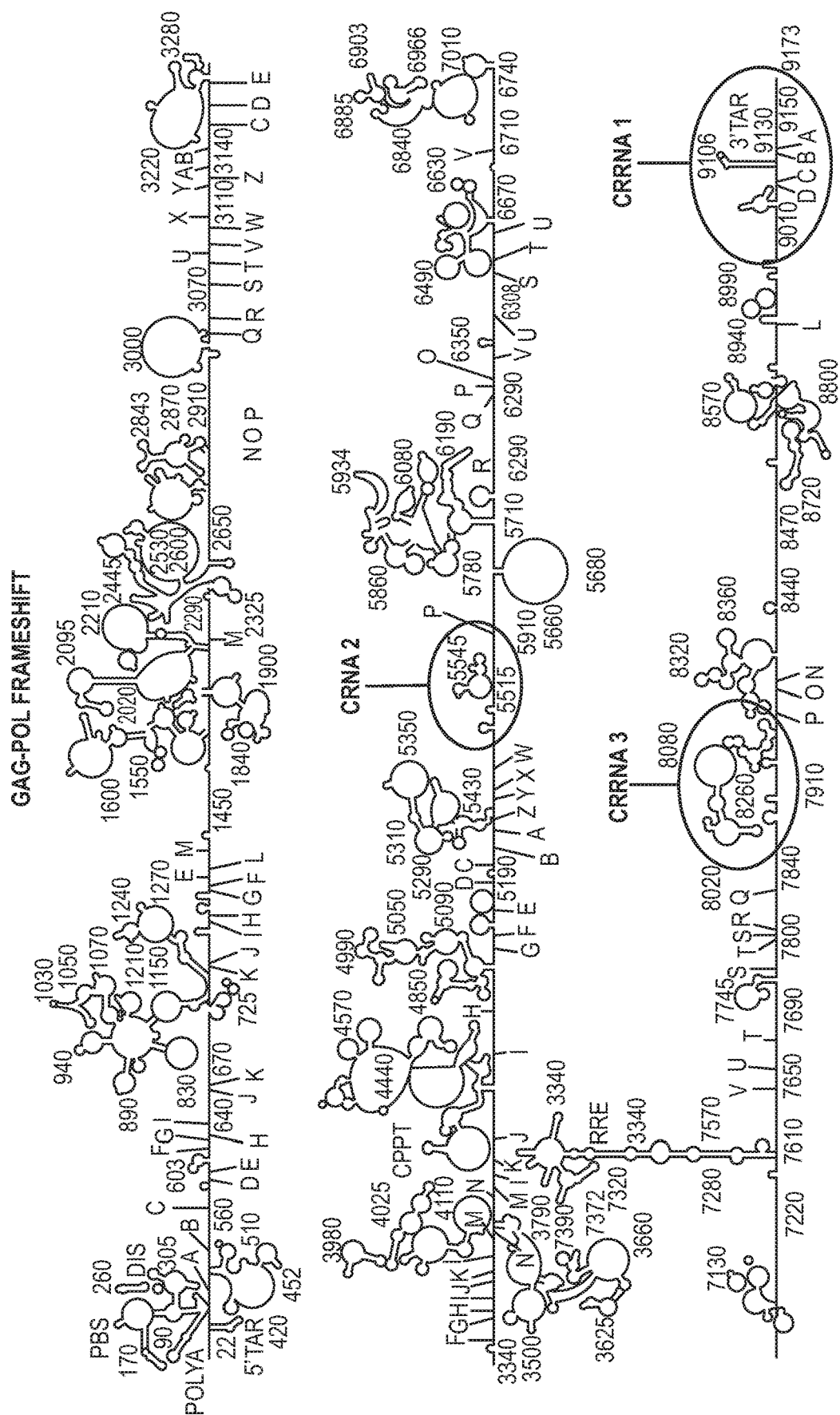
FIG. 5 is a schematic of the HIV-1 RNA genome and the extensive secondary structure composed of many local and long-distance interactions. Also shown are different crRNA recognition sites within the HIV-1 RNA genome.

FIG. 5 shows a schematic of the HIV-1 RNA genome and the extensive secondary structure composed of many local and long-distance interactions. Also shown are different crRNA recognition sites within the HIV-1 RNA genome for the crRNAs used for the detection of HIV shown in FIG. 6.

Figure 7:
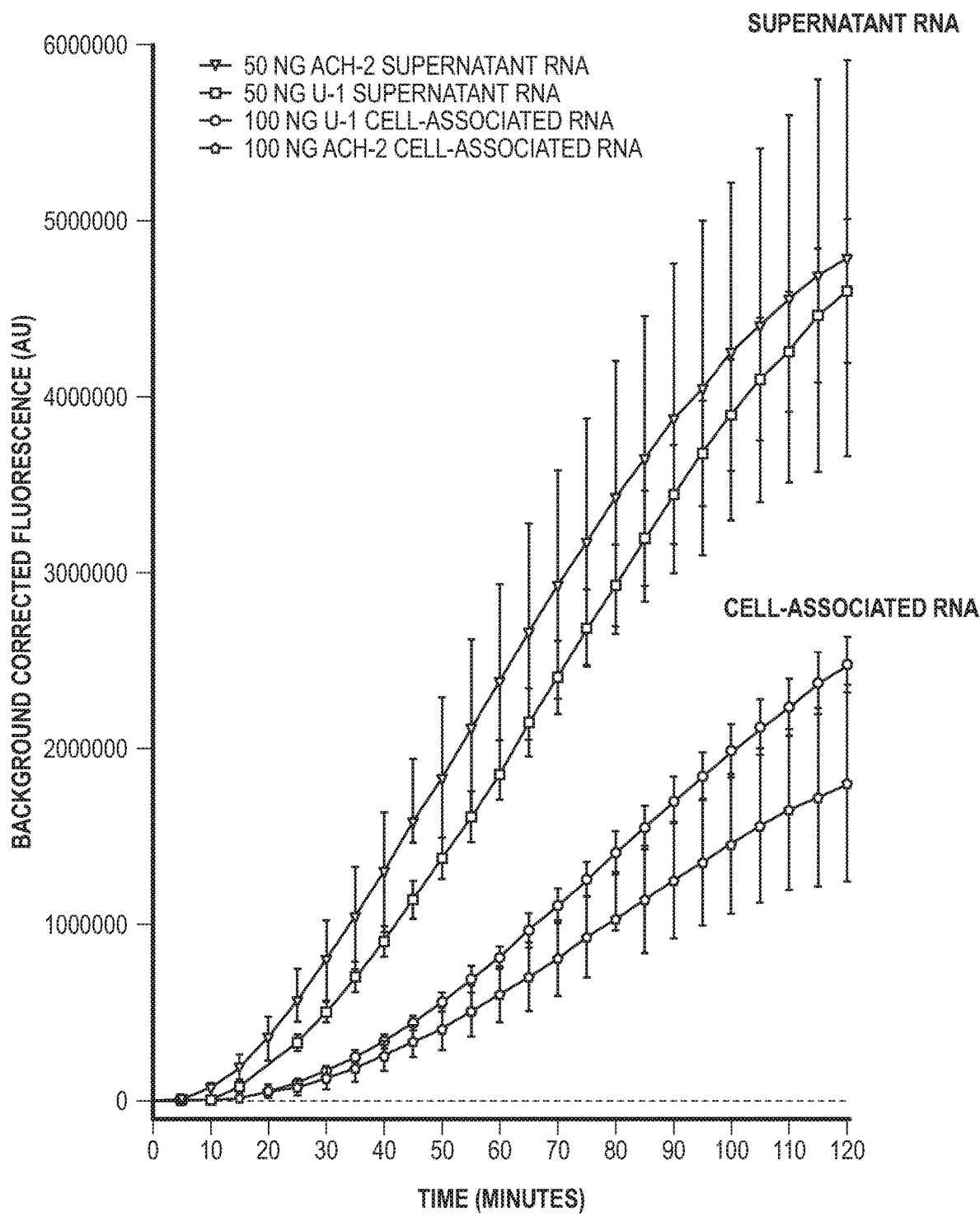
FIG. 7 demonstrates that supernatant (or virion) RNA is more easily detected with lower RNA input compared to cell-associated RNA from two replication competent cell lines.
Figure 8:
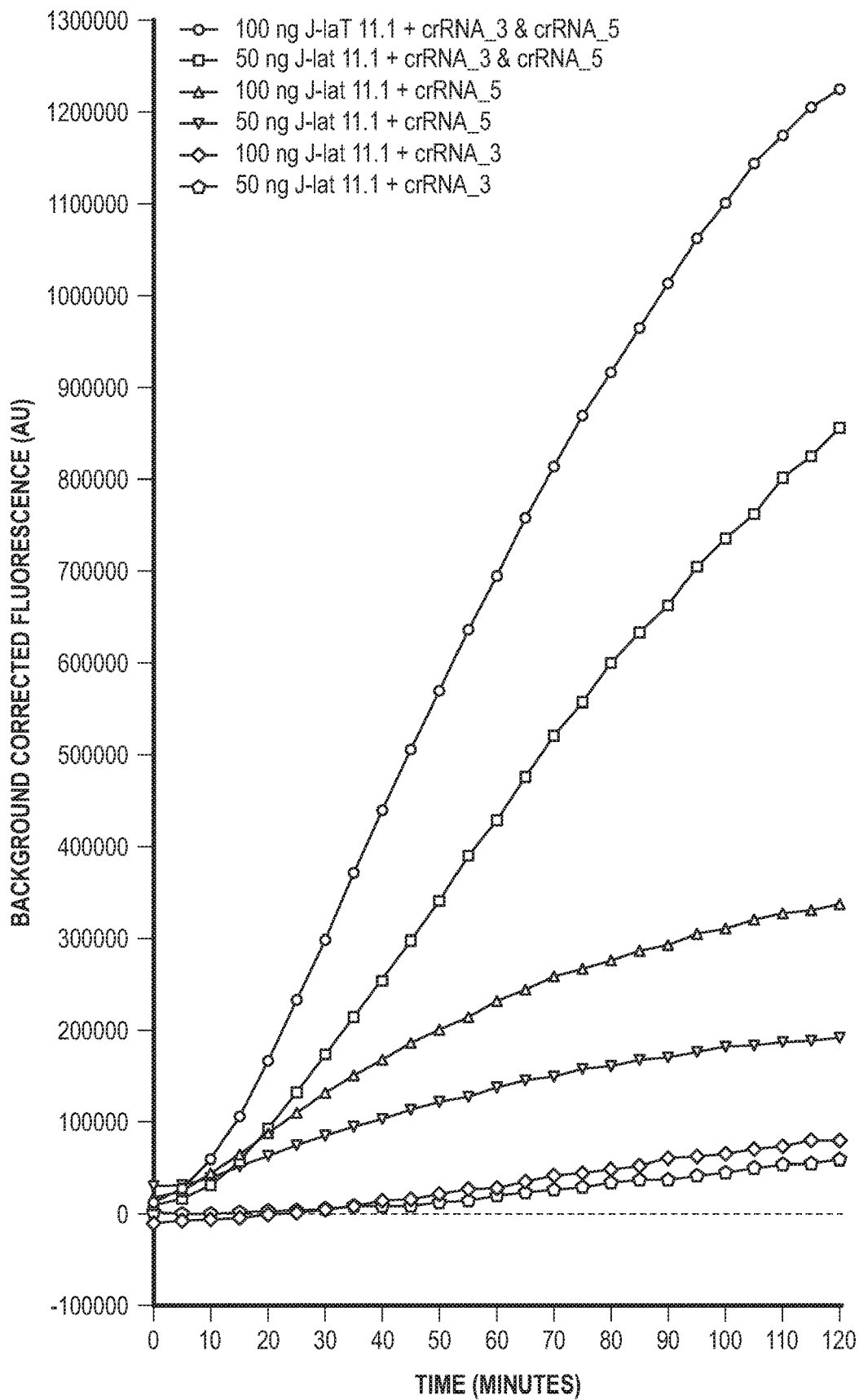
FIG. 8 demonstrates that the use of multiple crRNAs (multiplexing) can improve detection of HIV-1 RNA.
Figure 9:
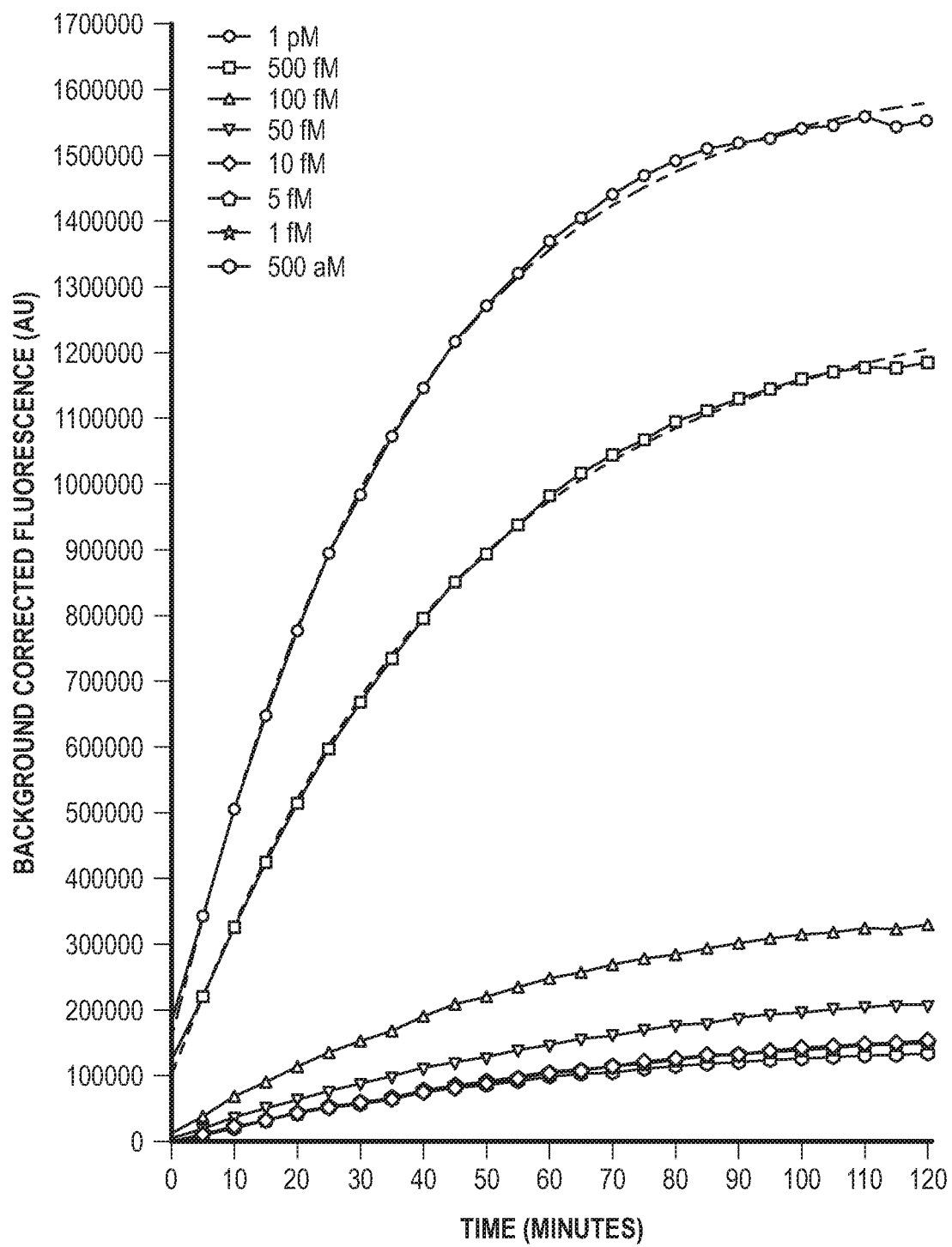
FIG. 9 demonstrates that Cas13a:crRNA RNP complexes can detect target RNA down to 500 attomole (aM), or $3.01 \times 10^5$ copies/mL.
Figure 10:
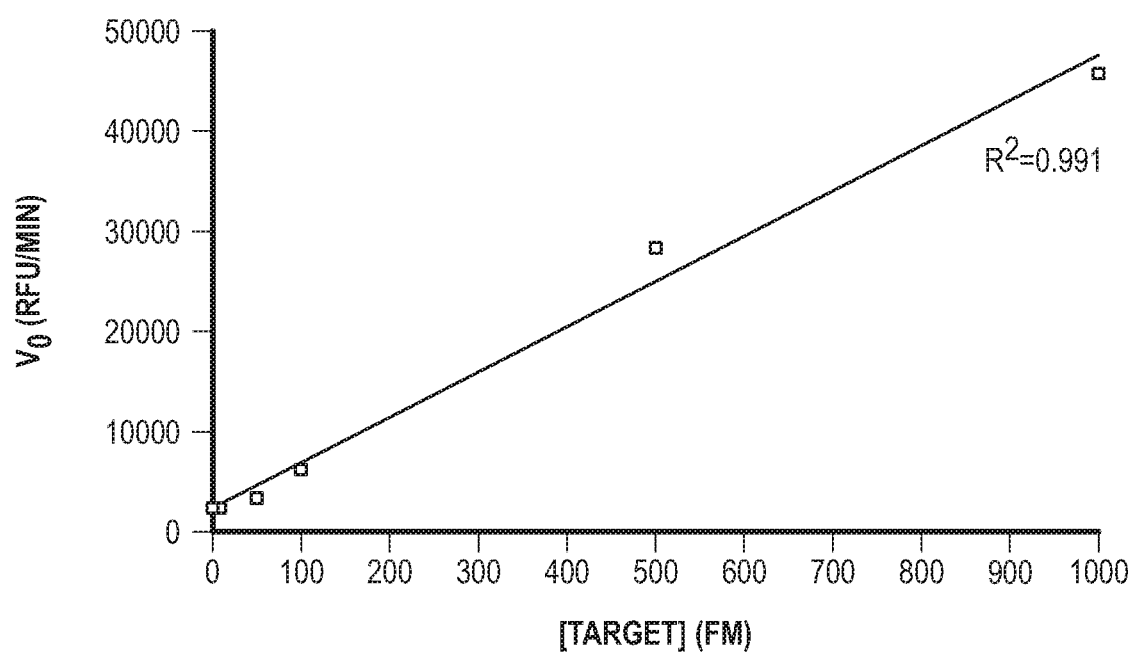
FIG. 10 illustrates that linear regression of a plot of the initial rates of fluorescence (x-intercept in FIG. 9) versus the concentration calculated for each "target" RNA allows a best fit line to be calculated, which provides a standard curve to interpolate concentrations of unknown samples.

FIG. 7 shows that supernatant (or virion) RNA is more easily detected with lower RNA input compared to cell-associated RNA from two replication competent cell lines, ACH-2 and U-1 cell lines. FIG. 8 shows that the use of multiple crRNAs (multiplexing) can improve detection of HIV-1 RNA. FIG. 9 shows that Cas13a:crRNA RNP complexes can detect target RNA (in this instance, a 50-nucleotide synthetic ssRNA containing a complimentary sequence to the crRNA) down to 500 aM, or $3.01 \times 10^5$ copies/mL. The initial rates at the x-intercept of FIG. 9 were calculated for each concentration of "target" RNA and plotted (FIG. 10). Linear regression allows for a best fit line to be calculated, which can be used as a standard curve to interpolate concentrations of unknown samples.

Example 2: Optimized CRISPR RNA (crRNA) Selection and Cas13a Protein

Cas13a activity is governed by target accessibility as the secondary structure of the target RNA influences the ability of the Cas13a:crRNA complex to bind the target sites. The HIV-1 RNA transcript contains several well-characterized RNA elements, and more recent studies have mapped the secondary structure of the entire HIV-1 genome at single nucleotide resolution (see, e.g. FIG. 5). These studies have shown extensive RNA secondary structure, in addition to long-range inter-genomic interactions, which will inform design of HIV-1 specific crRNAs.

To optimize accessibility and minimize hindrance by structure, crRNA spacer sequences will be synthesized across regions of the HIV-1 RNA genome identified as highly conserved among isolates. Comprehensive sequence information for many subtypes is available from the Los Alamos National Laboratory (LANL) HIV Sequence Database. This data will be analyzed to identify regions of conservation and low secondary structure for crRNA design and synthesis (Synthego). Conservation among the 3352 HIV isolates currently listed in the LANL HIV database will be calculated using the "Consensus Maker" tool, and further verified via multiple sequence alignment program ClustalX. Tiling of spacers will include a 5-nt overlap and will be designed in 20-nt intervals. Of special interest are regions used for primers previously used in RT-PCR including, if available, in FDA-approved detection kits.

The crRNAs will be pre-incubated with LbuCas13a protein and then with either the synthetic target HIV RNAs or isolated RNAs from infected and uninfected cells. Other Cas13 homologs will also be tested. RNA isolated from cell supernatant from ACH-2 and U1 cell lines, which contain HIV virions after activation with TNFα, to phenocopy detection of circulating viruses in the blood will be included. Samples will be analyzed on a Spectramax plate reader. Normalized reporter signal curve time courses will be fitted with single-exponential decays and the apparent rates will be compared with a standard curve of defined activator RNA concentrations. RNA from uninfected cells or mismatched synthetic target RNAs will be included as controls and the findings will be compared to parallel RT-qPCR and ddPCR results from the same samples.

LbuCas13a is a robust multiple-turnover enzyme capable of at least $10^4$ turnovers per target RNA recognized, even in the presence of low target RNA concentrations. This indicates that crRNA-directed trans cleavage is potent and detectable even at low levels of activated protein. Eleven homologs of Cas13a have been cloned, purified, and tested for the following characteristics: trans-ssRNA cleavage rate, sensitivity for HIV-1 RNA, and false-positive rate as a result of aberrant or nonspecific activation of the complex, all in the context of background RNA. These homologs will be tested with the crRNAs described above and all identified crRNAs will also be tested, alone or in combination. The Cas13a proteins to be tested are from the following bacteria: *Leptotrichia wadei, Rhodobacter capsulatus, Herbinix hemicellulosilytica, Leptotrichia buccalis, Listeria seeligeri, Paludibacter propionicigenes, Lachnospiraceae bacterium, [Eubacterium] rectale, Listeria newyorkensis, Clostridium aminophilum, Leptotrichia shahii*. Open reading frames of Cas13a proteins are cloned and available for bacterial expression and purification as described in East-Seletsky Nature (2016) and East-Seletsky Molecular Cell (2017).

For example, a *Leptotrichia wadei* Cas13a endonuclease can have the following sequence (SEQ ID NO:10; NCBI accession no. WP_036059678.1).

```
  1 MKITKIDGVS HYKKQDKGIL KKKWKDLDER KQREKIEARY

41 NKQIESKIYK EFFRLKNKKR IEKEEDQNIK SLYFFIKELY

81 LNEKNEEWEL KNINLEILDD KERVIKGYKF KEDVYFFKEG

121 YKEYYLRILF NNLIEKVQNE NREKVRKNKE FLDLKEIFKK

161 YKNRKIDLLL KSINNNKINL EYKKENVNEE IYGINPTNDR

201 EMTFYELLKE IIEKKDEQKS ILEEKLDNFD ITNFLENIEK

241 IFNEETEINI IKGKVLNELR EYIKEKEENN SDNKLKQIYN

281 LELKKYIENN FSYKKQKSKS KNGKNDYLYL NFLKKIMFIE

321 EVDEKKEINK EKFKNKINSN FKNLFVQHIL DYGKLLYYKE

361 NDEYIKNTGQ LETKDLEYIK TKETLIRKMA VLVSFAANSY

401 YNLFGRVSGD ILGTEVVKSS KTNVIKVGSH IFKEKMLNYF

441 FDFEIFDANK IVEILESISY SIYNVRNGVG HFNKLILGKY

481 KKKDINTNKR IEEDLNNNEE IKGYFIKKRG EIERKVKEKF

521 LSNNLQYYYS KEKIENYFEV YEFEILKRKI PFAPNFKRII

561 KKGEDLFNNK NNKKYEYFKN FDKNSAEEKK EFLKTRNFLL

601 KELYYNNFYK EFLSKKEEFE KIVLEVKEEK KSRGNINNKK

641 SGVSFQSIDD YDTKINISDY IASIHKKEME RVEKYNEEKQ
```

```
 681 KDTAKYIRDF VEEIFLTGFI NYLEKDKRLH FLKEEFSILC
 721 NNNNNVVDFN ININEEKIKE FLKENDSKTL NLYLFFNMID
 761 SKRISEFRNE LVKYKQFTKK RLDEEKEFLG IKIELYETLI
 801 EFVILTREKL DTKKSEEIDA WLVDKLYVKD SNEYKEYEEI
 841 LKLFVDEKIL SSKEAPYYAT DNKTPILLSN FEKTRKYGTQ
 881 SFLSEIQSNY KYSKVEKENI EDYNKKEEIE QKKKSNIEKL
 921 QDLKVELHKK WEQNKITEKE IEKYNNTTRK INEYNYLKNK
 961 EELQNVYLLH EMLSDLLARN VAFFNKWERD FKFIVIAIKQ
1001 FLRENDKEKV NEFLNPPDNS KGKKVYFSVS KYKNTVENID
1041 GIHKNFMNLI FLNNKEMNRK IDKMNCAIWV YFRNYIAHFL
1081 HLHTKNEKIS LISQMNLLIK LFSYDKKVQN HILKSTKTLL
1121 EKYNIQINFE ISNDKNEVFK YKIKNRLYSK KGKMLGKNNK
1162 LENEFLE NVKAMLEYSE
```

Other sequences for *Leptotrichia wadei* Cas13a endonucleases are also available, such as those NCBI accession nos. BBM46759.1, BBM48616.1, BBM48974.1, BBM48975.1, and WP_021746003.1.

In another example, a *Herbinix hemicellulosilytica* Cas13a endonuclease can have the following sequence (SEQ ID NO: 11; NCBI accession no. WP_103203632.1).

```
   1 MKLTRRRISG NSVDQKITAA FYRDMSQGLL YYDSEDNDCT
  41 DKVIESMDFE RSWRGRILKN GEDDKNPFYM FVKGLVGSND
  81 KIVCEPIDVD SDPDNLDILI NKNLTGFGRN LKAPDSNDTL
 121 ENLIRKIQAG IPEEEVLPEL KKIKEMIQKD IVNRKEQLLK
 161 SIKNNRIPFS LEGSKLVPST KKMKWLFKLI DVPNKTFNEK
 201 MLEKYWEIYD YDKLKANITN RLDKTDKKAR SISRAVSEEL
 241 REYHKNLRTN YNRFVSGDRP AAGLDNGGSA KYNPDKEEFL
 281 LFLKEVEQYF KKYFPVKSKH SNKSKDKSLV DKYKNYCSYK
 321 VVKKEVNRSI INQLVAGLIQ QGKLLYYFYY NDTWQEDFLN
 361 SYGLSYIQVE EAFKKSVMTS LSWGINRLTS FFIDDSNTVK
 401 FDDITTKKAK EAIESNYFNK LRTCSRMQDH FKEKLAFFYP
 441 VYVKDKXDRP DDDIENLIVL VKNAIESVSY LRNRTFHFKE
 481 SSLLELLKEL DDKNSGQNKI DYSVAAEFIK RDIENLYDVF
 521 REQIRSLGIA EYYKADMISD CFKTCGLEFA LYSPKNSLMP
 561 AFKNVYKRGA NLNKAYIRDK GPKETGDQGQ NSYKALEEYR
 601 ELTWYIEVKN NDQSYNAYKN LLQLIYYHAF LPEVRENEAL
 641 ITDFINRTKE WNRKETEERL NTKNNKKHKN FDENDDITVN
 681 TYRYESIPDY QGESLDDYLK VLQRKQMARA KEVNEKEEGN
 721 NNYIQFIRDV VWAFGAYLE NKLKNYKNEL QPPLSKENIG
 761 LNDTLKELFP EEKVKSPFNI KCRFSISTFI DNKGKSTDNT
 801 SAEAVKTDGK EDEKDKKNIK RKDLLCFYLF LRLLDENEIC
 841 KLQHQFIKYR CSLKERRFPG NRTKLEKETE LLAELEELME
 881 LVRFTMPSIP EISAKAESGY DTMIKKYFKD FIEKKVFKNP
 921 KTSNLYYHSD SKTPVTRKYM ALLMRSAPLH LYKDIFKGYY
 961 LITKKECLEY IKLSNIIKDY QNSLNELHEQ LERIKLKSEK
1001 QNGKDSLYLD KKDFYKVKEY VENLEQVARY KHLQHKINFE
1041 SLYRIFRIHV DIAARMVGYT QDWERDMHFL FKALVYNGVL
1081 EERRFEAIFN NNDDNNDGRI VKKIQNNLNN KNRELVSMLC
1121 WNKKLNKNEF GAIIWKRNPI AHLNHFTQTE QNSKSSLESL
1161 INSLRILLAY DRKRQNAVTK TINDLLLNDY HIRIKWEGRV
1201 DEGQIYFNIK EKEDIENEPI IHLKHLHKKD CYIYKNSYMF
1241 DKQKEWICNG IKEEVYDKSI LKCIGNLFKF DYEDKNKSSA
1281 NPKHT
```

For example, a *Leptotrichia buccalis* Cas13a endonuclease can have the following sequence (SEQ ID NO: 12; NCBI accession no. WP_015770004.1).

```
   1 MKVTKVGGIS HKKYTSEGRL VKSESEENRT DERLSALLNM
  41 RLDMYIKNPS STETKENQKR IGKLKKFFSN KMVYLKDNTL
  81 SLKNGKKENI DREYSETDIL ESDVRDKKNF AVLKKIYLNE
 121 NVNSEELEVF RNDIKKKLNK INSLKYSFEK NKANYQKINE
 161 NNIEKVEGKS KRNIIYDYYR ESAKRDAYVS NVKEAFDKLY
 201 KEEDIAKLVL EIENLTKLEK YKIREFYHEI IGRKNDKENF
 241 AKIIYEEIQN VNNMKELIEK VPDMSELKKS QVFYKYYLDK
 281 EELNDKNIKY AFCHFVEIEM SQLLKNYVYK RLSNISNDKI
 321 KRIFEYQNLK KLIENKLLNK LDTYVRNCGK YNYYLQDGEI
 361 ATSDFIARNR QNEAFLRNII GVSSVAYFSL RNILETENEN
 401 DITGRMRGKT VKNNKGEEKY VSGEVDKIYN ENKKNEVKEN
 441 LKMFYSYDFN MDNKNEIEDF FANIDEAISS IRHGIVHFNL
 481 ELEGKDIFAF KNIAPSEISK KMFQNEINEK KLKLKIFRQL
 521 NSANVFRYLE KYKILNYLKR TRFEFVNKNI PFVPSFTKLY
 561 SRIDDLKNSL GIYWKTPKTN DDNKTKEIID AQIYLLKNIY
 601 YGEFLNYFMS NNGNFFEISK EIIELNKNDK RNLKTGFYKL
 641 QKFEDIQEKI PKEYLANIQS LYMINAGNQD EEEKDTYIDF
 681 IQKIFLKGFM TYLANNGRLS LIYIGSDEET NTSLAEKKQE
 721 FDKFLKKYEQ NNNIKIPYEI NEFLREIKLG NILKYTERLN
 761 MFYLILKLLN HKELTNLKGS LEKYQSANKE EAFEDQLELI
 801 NLLNLDNNRV TEDFELEADE IGKFLDFNGN KVKDNKELKK
 841 FDTNKIYFDG ENIIKHRAFY NIKKYGMLNL LEKIADKAGY
 881 KISIEELKKY SNKKNEIEKN HKMQENLHRK YARPRKDEKF
 921 TDEDYESYKQ AIENIEEYTH LKNKVEFNEL NLLQGLLLRI
 961 LHRLVGYTSI WERDLRFRLK GEFPENQYIE EIFNFENKKN
1001 VKYKGGQIVE KYIKFYKELH QNDEVKINKY SSANIKVLKQ
```

```
1041 EKKDLYIRNY IAHFNYIPHA EISLLEVLEN LRKLLSYDRK

1081 LKNAVMKSVV DILKEYGFVA TFKIGADKKI GIQTLESEKI

1121 VHLKNLKKKK LMTDRNSEEL CKLVKIMFEY KMEEKKSEN
```

For example, a *Leptotrichia seeligeri* Cas13a endonuclease can have the following sequence (SEQ ID NO:13, NCBI accession no. WP_012985477.1).

```
   1 MWISIKTLIH HLGVLFFCDY MYNRREKKII EVKTMRITKV

41 EVDRKKVLIS RDKNGGKLVY ENEMQDNTEQ IMHHKKSSFY

81 KSVVNKTICR PEQKQMKKLV HGLLQENSQE KIKVSDVTKL

121 NISNFLNHRF KKSLYYFPEN SPDKSEEYRI EINLSQLLED

161 SLKKQQGTFI CWESFSKDME LYINWAENYI SSKTKLIKKS

201 IRNNRIQSTE SRSGQLMDRY MKDILNKNKP FDIQSVSEKY

241 QLEKLTSALK ATFKEAKKND KEINYKLKST LQNHERQIIE

281 ELKENSELNQ FNIEIRKHLE TYFPIKKTNR KVGDIRNLEI

321 GEIQKIVNHR LKNKIVQRIL QEGKLASYEI ESTVNSNSLQ

361 KIKIEEAFAL KFINACLFAS NNLRNMVYPV CKKDILMIGE

401 FKNSFKEIKH KKFIROWSQF FSQEITVDDI ELASWGLRGA

441 IAPIRNEIIH LKKHSWKKFF NNPTFKVKKS KIINGKTKDV

481 TSEFLYKETL FKDYFYSELD SVPELIINKM ESSKILDYYS

521 SDQLNQVFTI PNFELSLLTS AVPFAPSFKR VYLKGFDYQN

561 QDEAQPDYNL KLNIYNEKAF NSEAFQAQYS LFKMVYYQVF

601 LPQFTTNNDL FKSSVDFILT LNKERKGYAK AFQDIRKMNK

641 DEKPSEYMSY IQSQLMLYQK KQEEKEKINH FEKFINQVFI

681 KGFNSFIEKN RLTYICHPTK NTVPENDNIE IPFHTDMDDS

721 NIAFWLMCKL LDAKQLSELR NEMIKFSCSL QSTEEISTFT

761 KAREVIGLAL LNGEKGCNDW KELFDDKEAW KKNMSLYVSE

801 ELLQSLPYTQ EDGQTPVINR SIDLVKKYGT ETILEKLFSS

841 SDDYKVSAKD IAKLHEYDVT EKIAQQESLH KQWIEKPGLA

881 RDSAWTKKYQ NVINDISNYQ WAKTKVELTQ VRHLHQLTID

921 LLSRLAGYMS IADRDFQFSS NYILERENSE YRVTSWILLS

961 ENKNKNKYND YELYNLKNAS IKVSSKNDPQ LKVDLKQLRL

1001 TLEYLELFDN RLKEKRNNIS HFNYLNGQLG NSILELFDDA

1041 RDVLSYDRKL KNAVSKSLKE ILSSHGMEVT FKPLYQTNHH

1081 LKIDKLQPKK IHHLGEKSTV SSNQVSNEYC QLVRTLLTMK
```

For example, a *Paludibacter propionicigenes* Cas13a endonuclease can have the following sequence (SEQ ID NO: 14, NCBI accession no. WP_013443710.1).

```
   1 MRVSKVKVKD GGKDKMVLVH RKTTGAQLVY SGQPVSNETS

41 NILPEKKRQS FDLSTLNKTI IKFDTAKKQK LNVDQYKIVE

81 KIFKYPKQEL PKQIKAEEIL PFLNHKFQEP VKYWKNGKEE

121 SFNLTLLIVE AVQAQDKRKL QPYYDWKTWY IQTKSDLLKK

161 SIENNRIDLT ENLSKRKKAL LAWETEFTAS GSIDLTHYHK

201 VYMTDVLCKM LQDVKPLTDD KGKINTNAYH RGLKKALQNH

241 QRAIFGTREV PNEANRADNQ LSIYHLEVVK YLEHYFPIKT

281 SKRRNTADDI AHYLKAQTLK TTIEKQLVNA IRANIIQQGK

321 TNHHELKADT TSNDLIRIKT NEAFVLNLTG TCAFAANNIR

361 NMVDNEQTND ILGKGDFIKS LLKDNINSQL YSFFFGEGLS

401 TNKAEKETQL WGIRGAVQQI RNNVNHYKKD ALKTVFNISN

441 FENPTITDPK QQTNYADTIY KARFINELEK IPEAFAQQLK

481 TGGAVSYYTI ENLKSLLTTF QFSLCRSTIP FAPGFKKVFN

521 GGINYQNAKQ DESFYELMLE QYLRKENFAE ESYNARYFML

561 KLIYNNLFLP GFTTDRKAFA DSVGFVOMQN KKQAEKVNPR

601 KKEAYAFEAV RPMTAADSIA DYMAYVQSEL MQEQNKKEEK

641 VAEETRINFE KFVLQVFIKG FDSFLRAKEF DFVQMPQPQL

681 TATASNQQKA DKLNQLEASI TADCKLTPQY AKADDATHIA

721 FYVFCKLLDA AHLSNLRNEL IKFRESVNEF KFHHLLEIIE

761 ICLLSADVVP TDYRDLYSSE ADCLARLRPF IEQGADITNW

801 SDLFVQSDKH SPVIHANIEL SVKYGTTKLL EQIINKDTQF

841 KTTEANFTAW NTAQKSIEQL IKQREDHHEQ WVKAKNADDK

881 EKQERKREKS NFAQKFIEKH GDDYLDICDY INTYNWLDNK

921 MHFVHLNRLH GLTIELLGRM AGFVALFDRD FQFFDEQQIA

961 DEFKLHGFVN LHSIDKKLNE VPTKKIKEIY DIRNKIIQIN

1001 GNKINESVRA NLIQFISSKR NYYNNAFLHV SNDEIKEKQM

1041 YDIRNHIAHF NYLTKDAADF SLIDLINELR ELLHYDRKLK

1081 NAVSKAFIDL FDKHGMILKL KLNADHKLKV ESLEPKKIYH

1121 LGSSAKDKPE YQYCTNQVMM AYCNMCRSLL EMKK
```

For example, a *Lachnospiraceae bacterium* Cas13a endonuclease can have the following sequence (SEQ ID NO: 15, NCBI accession no. WP_022785443.1).

```
   1 MKISKVREEN RGAKLTVNAK TAVVSENRSQ EGILYNDPSR

41 YGKSRKNDED RDRYIESRLK SSGKLYRIFN EDKNKRETDE

81 LQWFLSEIVK KINRRNGLVL SDMLSVDDRA FEKAFEKYAE

121 LSYTNRRNKV SGSPAFETCG VDAATAERLK GIISETNFIN

161 RIKNNIDNKV SEDIIDRIIA KYLKKSLCRE RVKRGLKKLL

201 MNAFDLPYSD PDIDVQRDFI DYVLEDFYHV RAKSQVSRSI

241 KNMNMPVQPE GDGKFAITVS KGGTESGNKR SAEKEAFKKF

281 LSDYASLDER VRDDMLRRMR RLVVLYFYGS DDSKLSDVNE

321 KFDVWEDHAA RRVDNREFIK LPLENKLANG KTDKDAERIR

361 KNTVKELYRN QNIGCYRQAV KAVEEDNNGR YFDDKMLNMF

401 FIHRIEYGVE KIYANLKQVT EFKARTGYLS EKIWKDLINY

441 ISIKYIAMGK AVYNYAMDEL NASDKKEIEL GKISEEYLSG
```

```
481 ISSFDYELIK AEEMLQRETA VYVAFAARHL SSQTVELDSE
521 NSDFLLLKPK GTMDKNDKNK LASNNILNFL KDKETLRDTI
561 LQYFGGHSLW TDFPFDKYLA GGKDDVDFLT DLKDVIYSMR
601 NDSFHYATEN HNNGKWNKEL ISAMFEHETE RMTVVMKDKF
641 YSNNLPMFYK NDDLKKLLID LYKDNVERAS QVPSFNKVFV
681 RKNFPALVRD KDNLGIELDL KADADKGENE LKFYNALYYM
721 FKEIYYNAFL NDKNVRERFI TKATKVADNY DRNKERNLKD
761 RIKSAGSDEK KKLREQLQNY IAENDFGQRI KNIVQVNPDY
801 TLAQICQLIM TEYNQQNNGC MQKKSAARKD INKDSYQHYK
841 MLLLVNLRKA FLEFIKENYA FVLKPYKHDL CDKADFVPDF
881 AKYVKPYAGL ISRVAGSSEL QKWYIVSRFL SPAQANHMLG
921 FLHSYKQYVW DIYRRASETG TEINHSIAED KIAGVDITDV
961 DAVIDLSVKL CGTISSEISD YFKDDEVYAE YISSYLDFEY
1001 DGGNYKDSLN RFCNSDAVND QKVALYYDGE HPKLNRNIIL
1041 SKLYGERRFL EKITDRVSRS DIVEYYKLKK ETSQYQTKGI
1081 FDSEDEQKNI KKFQEMKNIV EFRDLMDYSE IADELQGQLI
1121 NWIYLRERDL MNFQLGYHYA CLNNDSNKQA TYVTLDYQGK
1161 KNRKINGAIL YQICAMYING LPLYYVDKDS SEWTVSDGKE
1201 STGAKIGEFY RYAKSFENTS DCYASGLEIF ENISEHDNIT
1241 ELRNYIEHFR YYSSFDRSFL GIYSEVFDRF FTYDLKYRKN
1281 VPTILYNILL QHFVNVRFEF VSGKKMIGID KKDRKIAKEK
1321 ECARITIREK NGVYSEQFTY KLKNGTVYVD ARDKRYLQSI
1361 IRLLFYPEKV NMDEMIEVKE KKKPSDNNTG KGYSKRDRQQ
1401 DRKEYDKYKE KKKKEGNFLS GMGGNINWDE INAQLKN
```

For example, a *Leptotrichia shahii* Cas13a endonuclease can have the following sequence (SEQ ID NO: 16; NCBI accession no. BBM39911.1).

```
  1 MGNLFGHKRW YEVRDKKDFK IKRKVKVKRN YDGNKYILNI
 41 NENNNKEKID NNKFIRKYIN YKKNDNILKE FTRKFHAGNI
 81 LFKLKGKEGI IRIENNDDFL ETEEVVLYIE AYGKSEKLKA
121 LGITKKKIID EAIRQGITKD DKKIEIKRQE NEEEIEIDIR
161 DEYTNKTLND CSIILRIIEN DELETKKSIY EIFKNINMSL
201 YKIIEKIIEN ETEKVFENRY YEEHLREKLL KDDKIDVILT
241 NFMEIREKIK SNLEILGFVK FYLNVGGDKK KSKNKKMLVE
281 KILNINVDLT VEDIADFVIK ELEFWNITKR IEKVKKVNNE
321 FLEKRRNRTY IKSYVLLDKH EKFKIERENK KDKIVKFFVE
361 NIKNNSIKEK IEKILAEFKI DELIKKLEKE LKKGNCDTEI
401 FGIFKKHYKV NFDSKKFSKK SDEEKELYKI IYRYLKGRIE
441 KILVNEQKVR LKKMEKIEIE KILNESILSE KILKRVKQYT
481 LEHIMYLGKL RHNDIDMTTV NTDDFSRLHA KEELDLELIT
521 FFASTNMELN KIFSRFNINN DENIDFFGGD REKNYVLDKK
561 ILNSKIKIIR DLDFIDNKNN ITNNFIRKFT KIGTNERNRI
601 LHAISKERDL QGTQDDYNKV INIIQNLKIS DEEVSKALNL
641 DVVFKDKKNI ITKINDIKIS EENNNDIKYL PSFSKVLPEI
681 LNLYRNNPKN EPFDTIETEK IVLNALIYVN KELYKKLILE
721 DDLEENESKN IFLQELKKTL GNIDEIDENI IENYYKNAQI
761 SASKGNNKAI KKYQKKVIEC YIGYLRKNYE ELFDFSDFKM
801 NIQEIKKQIK DINDNKTYER ITVKTSDKTI VINDDFEYII
841 SIFALLNSNA VINKIRNRFF ATSVWLNTSE YQNIIDILDE
881 IMQLNTLRNE CITENWNLNL EEFIQKMKEI EKDFDDFKIQ
921 TKKEIFNNYY EDIKNNILTE FKDDINGCDV LEKKLEKIVI
961 FDDETKFEID KKSNILQDEQ RKLSNINKKD LKKKVDQYIK
1001 DKDQEIKSKI LCRIIFNSDF LKKYKKEIDN LIEDMESENE
1041 NKFQEIYYPK ERKNELYIYK KNLFLNIGNP NEDKIYGLIS
1081 NDIKMADAKF LFNIDGKNIR KNKISEIDAI LKNINDKLNG
1121 YSKEYKEKYI KKLKENDDFF AKNIQNKNYK SFEKDYNRVS
1161 EYKKIRDLVE FNYLNKIESY LIDINWKLAI QMARFERDMH
1201 YIVNGLRELG IIKLSGYNTG ISRAYPKRNG SDGFYTTTAY
1241 YKFFDEESYK KFEKICYGFG IDLSENSEIN KPENESIRNY
1281 ISHFYIVRNP FADYSIAEQI DRVSNLLSYS TRYNNSTYAS
1321 VFEVFKKDVN LDYDELKKKF KLIGNNDILE RLMKPKKVSV
1361 LELESYNSDY IKNLIIELLT KIENTNDTL
```

In another example, a *Leptotrichia buccalis* C-1013-b Cas13a endonuclease can have the following sequence (SEQ ID NO:17, NCBI accession no. C7NBY4; AltName LbuC2c2).

```
  1 MKVTKVGGIS HKKYTSEGRL VKSESEENRT DERLSALLNM
 41 RLDMYIKNPS STETKENQKR IGKLKKFFSN KMVYLKDNTL
 81 SLKNGKKENI DREYSETDIL ESDVRDKKNF AVLKKIYLNE
121 NVNSEELEVF RNDIKKKLNK INSLKYSFEK NKANYQKINE
161 NNIEKVEGKS KRNIIYDYYR ESAKRDAYVS NVKEAFDKLY
201 KEEDIAKLVL EIENLTKLEK YKIREFYHEI IGRKNDKENF
241 AKIIYEEIQN VNNMKELIEK VPDMSELKKS QVFYKYYLDK
281 EELNDKNIKY AFCHFVEIEM SQLLKNYVYK RLSNISNDKI
321 KRIFEYQNLK KLIENKLLNK LDTYVRNCGK YNYYLQDGEI
361 ATSDFIARNR QNEAFLRNII GVSSVAYFSL RNILETENEN
401 DITGRMRGKT VKNNKGEEKY VSGEVDKIYN ENKKNEVKEN
441 LKMFYSYDFN MDNKNEIEDF FANIDEAISS IRHGIVHFNL
481 ELEGKDIFAF KNIAPSEISK KMFQNEINEK KLKLKIFRQL
521 NSANVFRYLE KYKILNYLKR TRFEFVNKNI PFVPSFTKLY
561 SRIDDLKNSL GIYWKTPKTN DDNKTKEIID AQIYLLKNIY
601 YGEFLNYFMS NNGNFFEISK EIIELNKNDK RNLKTGFYKL
```

```
641 QKFEDIQEKI PKEYLANIQS LYMINAGNQD EEEKDTYIDF

681 IQKIFLKGFM TYLANNGRLS LIYIGSDEET NTSLAEKKQE

721 FDKFLKKYEQ NNNIKIPYEI NEFLREIKLG NILKYTERLN

761 MFYLILKLLN HKELTNLKGS LEKYQSANKE EAFSDQLELI

801 NLLNLDNNRV TEDFELEADE IGKFLDFNGN KVKDNKELKK

841 FDTNKIYFDG ENIIKHRAFY NIKKYGMLNL LEKIADKAGY

881 KISIEELKKY SNKKNEIEKN HKMQENLHRK YARPRKDEKF

921 TDEDYESYKQ AIENIEEYTH LKNKVEFNEL NLLQGLLLRI

961 LHRLVGYTSI WERDLRFRLK GEFPENQYIE EIFNFENKKN

1001 VKYKGGQIVE KYIKFYKELH QNDEVKINKY SSANIKVLKQ

1041 EKKDLYIRNY IAHFNYIPHA EISLLEVLEN LRKLLSYDRK

1081 LKNAVMKSVV DILKEYGFVA TFKIGADKKI GIQTLESEKI

1121 VHLKNLKKKK LMTDRNSEEL CKLVKIMFEY KMEEKKSEN
```

Purified proteins will first be assayed for trans-ssRNA cleavage rates with HIV-specific crRNAs. This rate measures the trans cleavage of the fluorophore quencher-labeled ssRNA, which serves as an outread for complex activation and as a surrogate for the presence of HIV RNA. Notably, the rate at which trans cleavage reaches saturation varies greatly among Cas13a homologs. If the trans rate is too low, fluorescence outread will be undetectable, especially in the context of an excess of unlabeled human RNA. To systematically study the rate of trans cleavage in this context, we will test the ability of a preassembled ternary complex comprising the Cas13a:crRNA ribonucleoprotein (RNP) complex plus a bound synthetic ssRNA activator to degrade in trans the fluorophore quencher-labeled RNaseAlert substrate in the context of increasing amounts of tRNAs or purified human non-targeting RNAs. How the rate of trans cleavage reaches saturation over time will be monitored to identify ideal homologs with the fastest rate. Variables tested in this assay include concentrations of the Cas13a:crRNA RNP and concentrations of the reporter RNA to achieve optimized rates.

Next, the sensitivity of the homologs for cis cleavage of activating HIV ssRNA in the context of competitor RNA will be analyzed. A broad range of sensitivities (~$10^7$ fold) exist for these homologs in the context of just isolated activator RNA, but the influence of additional non-targeting RNAs on the cis cleavage rate is unknown. Background RNA, especially at high concentrations, can inhibit access to HIV RNA, precluding activation of the Cas13a:crRNA complex and downstream trans-cleavage. To test the influence of background RNA on cis-cleavage, a high-throughput screen will be used. For each Cas13a homolog, dilutions of the complementary fluorescent ssRNA activator will be systematically added with and without increasing amounts of tRNAs or purified human mRNAs and analyze cis cleavage rates of the reporter over time. Each resulting time course will allow the apparent rate of complementary target sensitivity to be calculated in the context of the defined competitor RNA background.

The specificity of the homologs will also be tested in the context of background competitor RNA to ensure that related RNA sequences cannot aberrantly or non-specifically activate the Cas13a:crRNA complex. Different Cas13a homologs tolerate different numbers of mismatches in the crRNA-target duplex. For example, Cas13a from *Leptotrichia shahii* (LshCas13a) is sensitive to double, but not single, mismatches in the crRNA-target duplex. Moreover, the location of these mismatches within the spacer sequence is important. For example, LshCas13a is sensitive to double mismatches in the center, or in the "seed region," of the crRNA-target duplex, but not at the 5' or 3' ends. It was recently discovered that LbuCas13a has a mismatch sensitive seed region that correlates well with observations for LshCas13a and the structure of LbuCas13a and that LbuCas13a has a mismatch sensitive switch region that effectively communicates activator RNA binding to the Higher Eukaryotes and Prokaryotes Nucleotide-binding (HEPN) nuclease for activation. We have generated a comprehensive mismatch sensitivity profile for LbuCas13a.

Data suggests that the mismatch sensitivity profile of homologs is quite variable. To test this comprehensively across all homologs, each homolog will be tested with crRNAs carrying systematic variations of mismatches against a known complimentary HIV-derived target sequence. Here, positions in the center of the spacer (positions 6 to 16) will be focused on. Double, triple, and quadruple consecutive and non-consecutive mismatches in this region of the crRNA will be generated by mutating the bases to the respective complementary base (e.g. A to U). A 50-nucleotide complimentary target RNAs will also be synthesized based on the no-mismatch crRNA sequence. A high-throughput screen will be used, and the screen mixtures will be fluorescence monitored to determine permissiveness to mismatches. Once the levels of permissiveness for each homolog with complimentary target RNA alone have been determined, the assay will be repeated in the presence of dilutions of tRNAs or human cellular RNAs to test for nonspecific activation of the complex by other RNA sequences. Homologs with some flexibility in low-number base-pair mismatches towards the target RNA will be accepted to allow for sequence variation in the HIV RNA sequence, but we aim to identify crRNA sequences and Cas13a homologs that together show the lowest aberrant activation by competitor RNAs.

Figure 11:
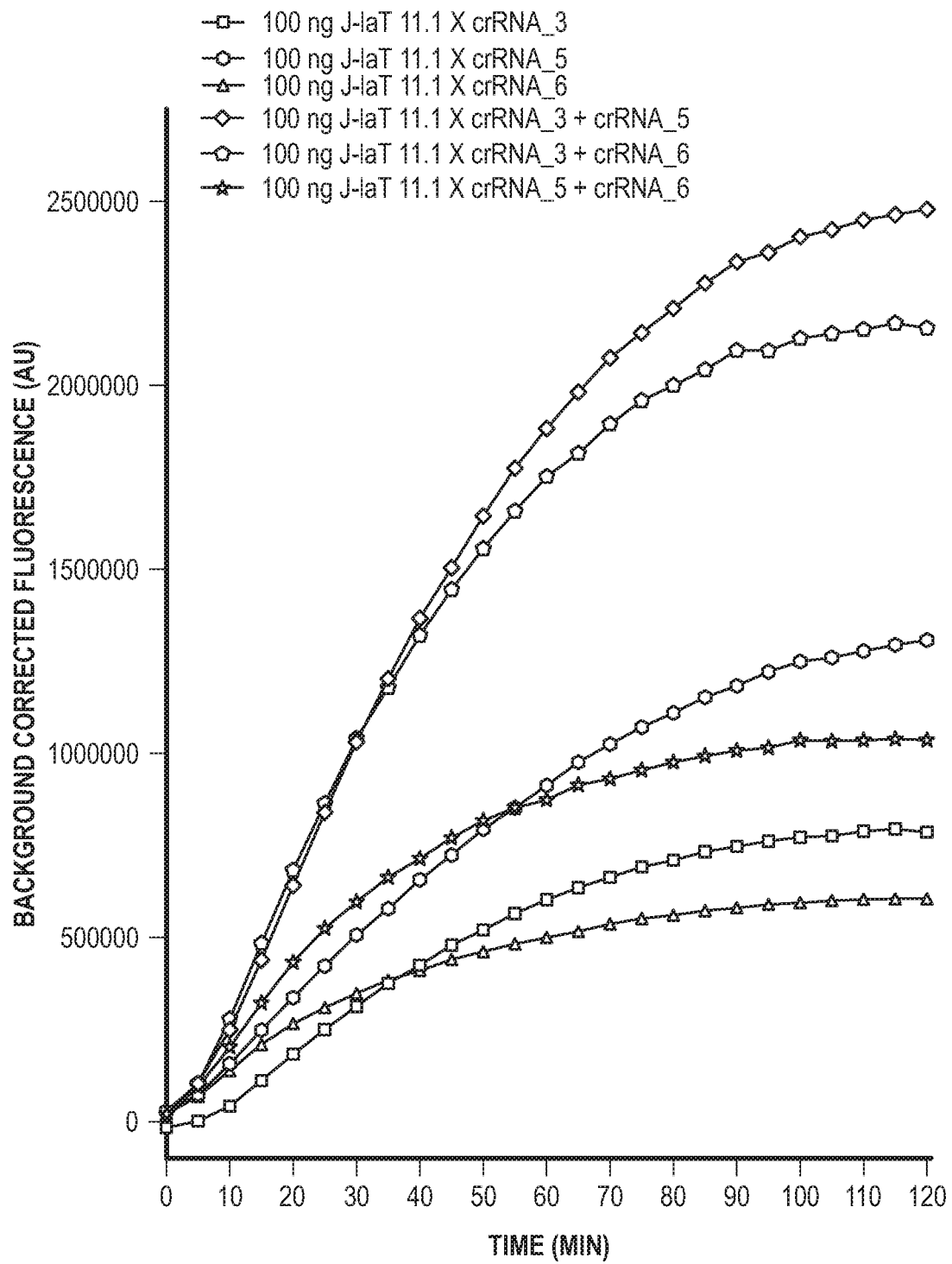
FIG. 11 illustrates detection of target HIV using specific combinations of crRNAs. As shown, the combination of crRNAs used are significant in terms of maximally improving sensitivity of the assay. Here, combining RNPs using crRNA #3 and crRNA #5 or crRNA #3 and crRNA #6 give improved results relative to single crRNAs. Combining crRNA #5 and crRNA #6 RNPs does not lead to improved sensitivity compared to using RNPs containing crRNA #5 alone.

FIG. 11 demonstrates that specific combinations of crRNAs matter maximally improved the sensitivity of the assay. As shown in FIG. 11, combining RNPs using crRNA #3 and crRNA #5 or crRNA #3 and crRNA #6 give improved results relative to single crRNAs. However, combining crRNA #5 and crRNA #6 RNPs did not lead to improved sensitivity compared to using RNPs containing crRNA #5 alone. Hence, the detection limits of the assays can be optimized by selection of particular crRNAs for use in reaction mixtures with different samples.

Example 3: Optimized Cas13a Assay for Self-Testing

Current home testing for HIV-1 has several limitations: 1) antibody-based testing utilizes saliva, where levels are generally lower than in blood; 2) this approach cannot be used for assessment of viral rebound after treatment interruptions as chronically infected individuals remain antibody-positive; and 3) advanced testing includes measurements of HIV p24 antigen but is hampered by circulating antibodies in chronically infected individuals. The gold standard for early and sensitive HIV detection is HIV RNA detection circulating in the blood, but this currently requires laboratory testing.

Here, a sensitive and single-step test for HIV RNA detection method is described that can be adapted to home testing methods that are being developed. A remaining concern is that RNases present in bodily fluids will non-specifically activate the read-out technology. As such, background fluorescence in blood, serum, and plasma samples due to circulating cellular RNases will be reduced. Cas13a and crRNA samples will be lyophilized to work towards electricity independence of the assay before rigorous analysis of cryopreserved or fresh clinical samples in comparison with FDA-approved HIV RNA testing.

Briefly, to optimize the assay for future finger-prick applications, comprehensive testing in whole blood, plasma and serum samples (without RNA extractions) obtained from uninfected blood donors will be obtained to assess and minimize background activation of the reporter readout by cellular RNases. Briefly, an RNase reporter oligonucleotide will be added directly to samples with and without dilutions of HIV-specific Cas13a:crRNA RNPs. Dilutions of purified NL4.3 HIV virions (NL4.3 generated in 293T cells after transfection) of known concentrations will then be added into each blood component and detection of HIV RNA will be measured by Cas13a:crRNA RNPs against the uninfected background. Positive detection will be confirmed and validated using RT-qPCR. If background fluorescence is found to be high in the various blood components and is not easily distinguishable from a true HIV-positive sample, RNase activity will be decreased using, for example, RNase A inhibitors (i.e. RNAsecure (Invitrogen), 5'8 diphosphoadenosine 3'-phosphate, Ribonucleoside Vanadyl Complex (NEB), and RNase OUT Recombinant Ribonuclease Inhibitor (Thermo Fisher)).

It is contemplated that some RNase A inhibitors will inhibit RNase A, but not Cas13a. As RNase A is not a HEPN-nuclease, its specific inhibitors are unlikely to inhibit the HEPN-nuclease of Cas13a dose-dependently. Briefly, dilutions of each ribonuclease inhibitor will be included into the assay both with and without Cas13a:crRNA RNP, the reporter oligonucleotide and isolated HIV virions of known concentration. Ribonuclease inhibitors that do not interfere with Cas13a activity will be tested directly in blood components mixed with reporter oligonucleotide with and without Cas13a:crRNAs to determine if background cleavage is minimized. Alternatively, samples will be heated to remove RNase activity. Previous studies have shown that virions from other RNA viruses (Zika and Dengue) can be spiked into human serum and heated to 95° C. for 1-2 minutes to increase release of viral RNA for detection. It will be determined whether a heating step facilitates detection of HIV RNA and if it reduces background RNase, but not specific Cas13a, detection. Additional testing of other methods (e.g., mechanical or chemical lysis) may also be performed. All experiments will be optimized with spiked-in HIV virions into blood components containing our reporter and Cas13a:crRNA RNPs with or without heat pre-treatment. For all studies, read-out fluorescence will be monitored using CellScope and a plate reader as control.

Example 4: Amplification of HIV RNA Before Testing

The Example illustrates that isolated HIV RNA can first be amplified, for example, using the bacteriophage-derived RNA-dependent RNA polymerase, Qβ replicase (see for example Shah et al (1994) *J Clin Microbiol* 32(11):2718).

HIV RNA was purified from Vsvg-pseudotyped virions containing HIV NL4-3 with GFP in place of env. HIV RNA was incubated with nucleotides (NTPs) and with or without Qβ replicase in reaction buffer (100 mM HEPES-NaOH, pH 7.5; 10 mM MgCl$_2$, and 1 mM EDTA). Amplified RNA was first purified using phenol and then added to the HIV-Cas13a assay. In some instances, specified as "no cleanup," the amplified mixture was directly added to the HIV-Cas13a assay.

Figure 12:
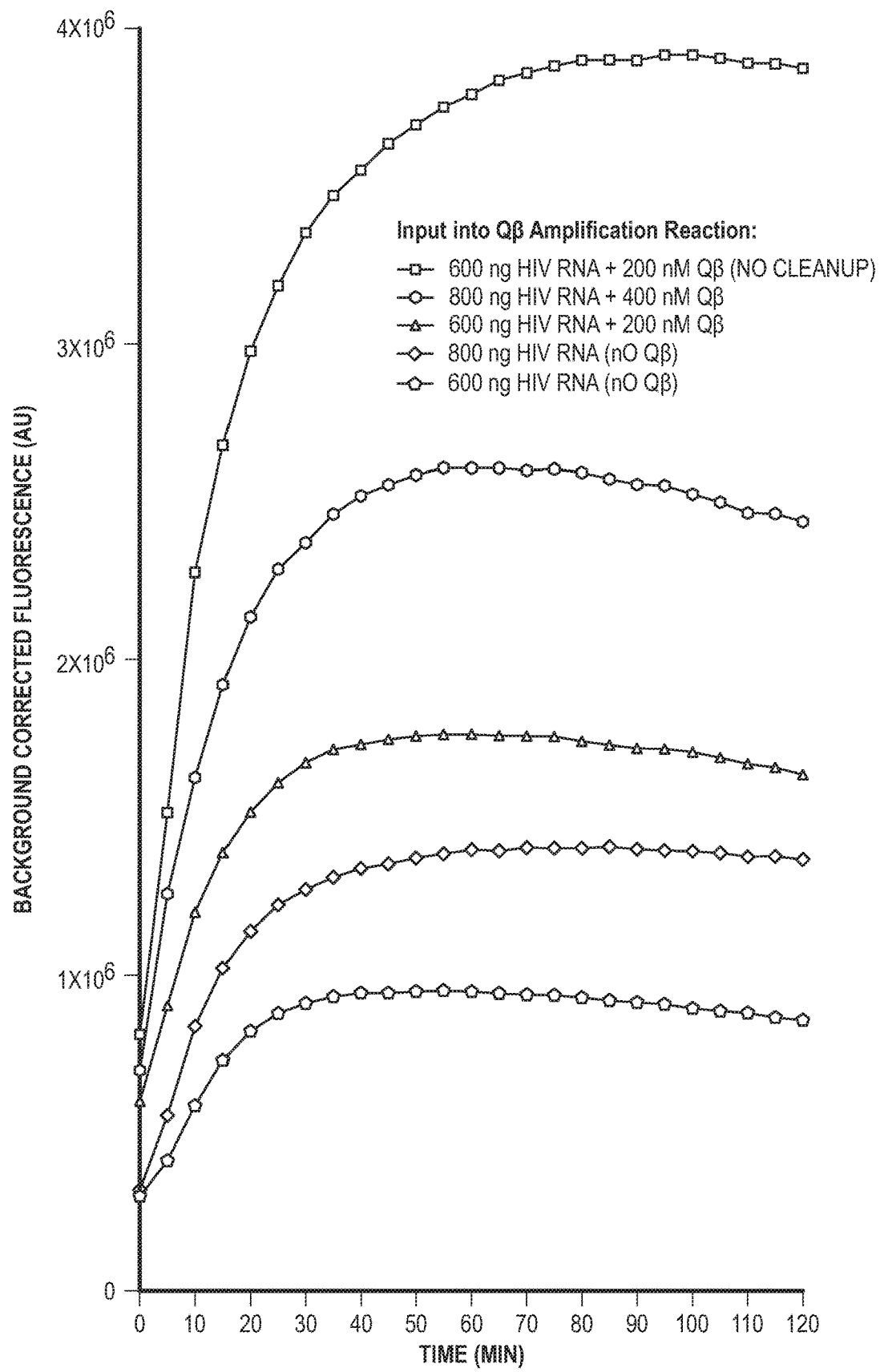
FIG. 12 illustrates that isolated HIV RNA can first be amplified using the bacteriophage-derived RNA-dependent RNA polymerase, Qβ replicase. HIV RNA from Vsvg-pseudotyped virions containing HIV NL4-3 with GFP in place of env was incubated with NTPs and with or without Qβ replicase in reaction buffer (100 mM HEPES-NaOH, pH 7.5; 10 mM $MgCl_2$, and 1 mM EDTA). Amplified RNA was in some cases purified using phenol and subsequently added to the HIV-Cas13a assay. However, in some instances, specified as "no cleanup," the amplification mixture was directly added to the HIV-Cas13a assay. Legend values reflect input concentrations in the initial amplification reaction.

As shown in FIG. 12, Qβ replicase-amplified HIV RNA can provide improved sensitivity in the HIV-Cas13a assay. No clean-up of the amplified product is needed before measuring the concentration of HIV RNA in the HIV-Cas13a assay.

Example 5: Cas13a Detection of HCV Transcripts

CRISPR RNA guides (crRNAs) were designed for HCV. Nine crRNAs were designed for HCV. Each crRNA includes a crRNA stem that is derived from a bacterial sequence, while the spacer sequence is derived from the HCV genome (reverse complement). See Table 2 (reproduced below) for crRNA sequences.

TABLE 2

Examples of HCV crRNA Sequences

| SEQ ID NO: | Name | Sequence |
|---|---|---|
| 18 | PF016_crLbu_JFH1_1 | GACCACCCCAAAAAUGAAGGGGACUAAA ACGUGUACUCACCGGUUCCGCA |
| 19 | PF017_crLbu_JFH1_2 | GACCACCCCAAAAAUGAAGGGGACUAAA ACCCCUAUCAGGCAGUACCACA |
| 20 | PF018_crLbu_JFH1_3 | GACCACCCCAAAAAUGAAGGGGACUAAA ACACCGGGUAGGUUCCCUGUUG |
| 21 | PF019_crLbu_JFH1_4 | GACCACCCCAAAAAUGAAGGGGACUAAA ACGGGCGACCAGUUCAUCAUCA |
| 22 | PF020_crLbu_JFH1_5 | GACCACCCCAAAAAUGAAGGGGACUAAA ACGACGAUGACCUUCUUCUCCA |
| 23 | PF021_crLbu_JFH1_6 | GACCACCCCAAAAAUGAAGGGGACUAAA ACUUCCACUGCCAGUUGGAGCA |
| 24 | PF022_crLbu_JFH1_7 | GACCACCCCAAAAAUGAAGGGGACUAAA ACGUUCAUCCAUUGGACCGCGC |
| 25 | PF023_crLbu_JFH1_8 | GACCACCCCAAAAAUGAAGGGGACUAAA ACGGCUCGAGAAAGUCCAGAAC |
| 26 | PF024_crLbu_JFH1_9 | GACCACCCCAAAAAUGAAGGGGACUAAA ACUCUGCAGAGAGACCAGUUAC |

Total RNA was isolated from Huh 7.5 cells infected with a MOI of 0.1 of the JFH-1 strain of HCV. Activator Huh 7.5 ssRNA targets were prepared at 100 pM in TE buffer, pH 8. RNA was calculated to 325 ng in 0.65 μL water containing diethyl pyrocarbonate (DEPC water).

A complex master mix was made by mixing 5× buffer, DEPC water, and crRNAs with SEQ ID NOs: 21 and 25 were diluted to 28 pM in TE buffer, pH 8, which was then combined with Cas13a protein. Controls without Cas13a protein were also made. The complex master mixes were then incubated at 37° C. for 30-60 minutes. DEPC water was added to lyophilized RNaseAlert (ThermoFisher Scientific) to resuspend. Target mixes were then made by adding RNase Alert, DEPC water, and 5× buffer to individually aliquoted Huh 7.5 RNA activator samples. Five μL of target mix was added to each well of a 384-well plate along with 15 μL of appropriate complex master mix. The formation of RNA cleavage products was monitored with a fluorometer.

Figure 13:
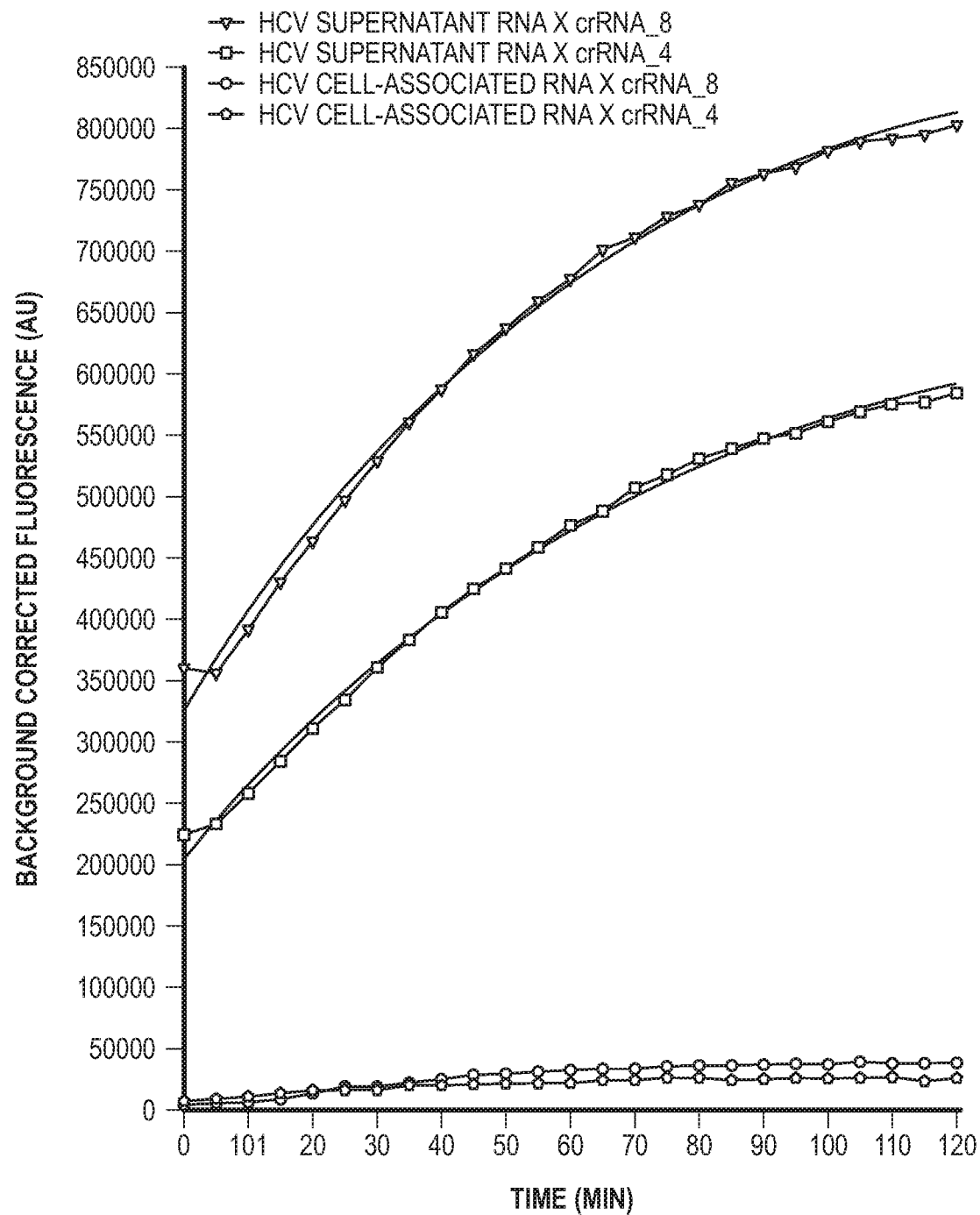
FIG. 13 shows that cell-associated supernatant HCV RNA was detected robustly with both HCV-specific crRNAs (SEQ ID NO:21 or 25), compared to no detection with mock-treated cells (not shown).

As shown in FIG. 13, cell-associated supernatant HCV RNA is detected robustly with both HCV-specific crRNAs (SEQ ID NO:21 or 25), compared to no detection with mock-treated cells (not shown).

REFERENCES

East-Seletsky et al. *Two distinct RNase activities of CRISPR-C2c2 enable guide-RNA processing and RNA detection*, NATURE 538(7624): 270-273 (2016)

East-Seletsky et al. *RNA Targeting by Functionally Orthogonal Type VI-A CRISPR-Cas Enzymes*, MOLECULAR CELL 66(3): 373-383 (2017)

All publications, patent applications, patents and other references mentioned herein are expressly incorporated by reference in their entirety, to the same extent as if each were incorporated by reference individually. In case of conflict, the present specification, including definitions, will control.

The following statements provide a summary of some aspects of the inventive nucleic acids and methods described herein.

STATEMENTS

1. A method for diagnosing the presence or absence of an HIV or HCV infection comprising:
   (a) incubating a sample containing RNA with a Cas13a protein and at least one CRISPR guide RNA (crRNA) for a period of time to form a RNA cleavage product; and
   (b) detecting a level of HIV or HCV RNA cleavage product with a detector,
   wherein the RNA is not reverse transcribed prior to the detecting step.
2. The method of statement 1, further comprising a step of amplification of the RNA and/or the HIV or HCV RNA cleavage products.
3. The method of statement 1, wherein the RNA and/or the HIV or HCV RNA cleavage product are not amplified.
3. The method of any one of the preceding statements, wherein the detector is a fluorescence detector, optionally a short quenched-fluorescent RNA.
5. The method of any one of the preceding statements, wherein the at least one crRNA is any one of SEQ ID NO: 1-8, 18-25 or 26.
6. The method of any one of the preceding statements, wherein the sample is incubated with 2, 3, 4, 5, 6, 7, 8, 9, 10 or more crRNAs.
7. The method of any one of the preceding statements, wherein the HIV or HCV RNA cleavage product concentration is determined using a standard curve and the level of the HIV or HCV RNA cleavage product.
8. The method of any one of the preceding statements, further comprising depleting a portion of the sample prior to detecting step.
9. The method of statement 8, wherein the portion of the sample is a human nucleic acid portion.
10. The method of any one of the preceding statements, further comprising removing RNase from the sample.
11. The method of statement 10, wherein RNase is removed from the sample using an RNase inhibitor and/or heat.
12. The method of any one of the preceding statements, wherein the Cas13a protein and/or crRNA is lyophilized prior to incubation with the sample.
13. A method for quantifying HIV or HCV RNA concentration comprising:
   (a) incubating a sample containing RNA with a Cas13a protein and at least one CRISPR guide RNA (crRNA) for a period of time; and
   (b) analyzing the sample for HIV or HCV RNA cleavage product concentration with a detector,
   wherein the RNA is not reverse transcribed prior to the analyzing step.
14. The method of statement 13, wherein the HIV or HCV RNA cleavage product concentration is determined using a standard curve.
15. The method of any one of statements 14, wherein the HIV or HCV RNA cleavage product concentration is determined using a standard curve and the level of the HIV or HCV RNA cleavage product.
16. The method of statement 13 or statement 14, further comprising a step of amplification of the RNA and/or the HIV or HCV RNA cleavage product.
17. The method of any one of statements 13-16, wherein the RNA and/or the HIV or HCV RNA cleavage product are not amplified.
18. The method of any one of statements 13-17, wherein the detector is a fluorescence detector, optionally a short quenched-fluorescent RNA.
19. The method of any one of statements 13-18, wherein the at least one crRNA is any one of SEQ ID NO: 1-8, 18-25 or 26.
20. The method of any one of statements 13-19, wherein the sample is incubated with 2, 3, 4, 5, 6, 7, 8, 9, 10 or more crRNAs.
21. The method of any one of statements 13-20, further comprising depleting a portion of the sample prior to the analyzing step.
22. The method of statement 21, wherein the portion of the sample is a human nucleic acid portion.
23. The method of any one of statements 13-22, further comprising removing RNase from the sample.
24. The method of statement 23, wherein RNase is removed from the sample using an RNase inhibitor and/or heat.
25. The method of any one of statements 13-24, wherein the Cas13a protein and/or crRNA is lyophilized prior to incubation with the sample.
26. A method for identifying the presence or absence of HIV or HCV splice variants and/or mutations comprising:
   (a) incubating a sample containing RNA with a Cas13a protein and at least one CRISPR guide RNA (crRNA) for a period of time to form HIV or HCV RNA cleavage product; and
   (b) detecting the HIV or HCV splice variants and/or mutations by analyzing the HIV or HCV RNA cleavage product with a detector,
   wherein the at least one crRNA recognizes the HIV or HCV splice variants and/or mutations,
   and wherein the RNA is not reverse transcribed prior to the detecting step.
27. The method of statement 26, further comprising a step of amplification of the RNA and/or the HIV or HCV RNA cleavage product.
28. The method of any one of statements 26-27, wherein the RNA and/or the HIV or HCV RNA cleavage product are not amplified.
29. The method of any one of statements 26-28, wherein the detector is a fluorescence detector, optionally a short quenched-fluorescent RNA.
30. The method of any one of statements 26-29, wherein the sample is incubated with 2, 3, 4, 5, 6, 7, 8, 9, 10 or more crRNAs.

31. The method of any one of statements 26-30, wherein the HIV or HCV RNA cleavage product concentration is determined using a standard curve and the level of the HIV or HCV RNA cleavage product.
32. The method of any one of statements 26-31, further comprising depleting a portion of the sample prior to the detecting step.
33. The method of statement 32, wherein the portion of the sample is a human nucleic acid portion.
34. The method of any one of statements 26-33, further comprising removing RNase from the sample.
35. The method of statement 34, wherein RNase is removed from the sample using an RNase inhibitor and/or heat.
36. The method of any one of statements 26-35, wherein the Cas13a protein and/or crRNA is lyophilized prior to incubation with the sample.
37. A method for monitoring reactivation or rebound of HIV or HCV transcription comprising:
    (a) incubating a sample containing RNA with a Cas13a protein and at least one CRISPR guide RNA (crRNA) for a period of time to form HIV or HCV RNA cleavage product; and
    (b) detecting an amount of the HIV or HCV RNA cleavage product in the sample with a detector.
38. The method of statement 37, further comprising a step of amplification of the RNA and/or the HIV or HCV RNA cleavage product.
39. The method of any one of statements 37-38, wherein the RNA and/or the HIV or HCV RNA cleavage product are not amplified.
40. The method of any one of statements 37-39, wherein the detector is a fluorescence detector, optionally a short quenched-fluorescent RNA.
41. The method of any one of statements 37-40, wherein the at least one crRNA is any one of SEQ ID NO: 1-8, 18-25 or 26.
42. The method of any one of statements 37-41, wherein the sample is incubated with 2, 3, 4, 5, 6, 7, 8, 9, 10 or more crRNAs.
43. The method of any one of statements 37-42, wherein the HIV or HCV RNA cleavage product concentration is determined using a standard curve and the level of the HIV or HCV RNA cleavage product.
44. The method of any one of statements 37-43, further comprising depleting a portion of the sample prior to the detecting step.
45. The method of statement 44, wherein the portion of the sample is a human nucleic acid portion.
46. The method of any one of statements 37-45, further comprising removing RNase from the sample.
47. The method of statement 46, wherein RNase is removed from the sample using an RNase inhibitor and/or heat.
48. The method of any one of statements 37-47, wherein the Cas13a protein and/or crRNA is lyophilized prior to incubation with the sample.
49. The method of any one of statements 1-48, further comprising treating a patient with a sample that has detectable HIV or HCV RNA.
50. The method of statement 49, wherein detectable HIV or HCV is at least 2 copies HIV or HCV/ml sample, at least 5 copies HIV or HCV/ml sample, or at least 10 copies HIV or HCV/ml sample, or at least 20 copies HIV or HCV/ml sample, or at least 30 copies HIV or HCV/ml sample, or at least 40 copies HIV or HCV/ml sample, or at least 50 copies HIV or HCV/ml sample.
51. A method comprising treating a patient with detectable HIV or HCV detected by a method comprising:
    (a) incubating a reaction mixture comprising an RNA sample from the patient with a Cas13a protein and at least one CRISPR guide RNA (crRNA) for a period of time sufficient to form a RNA cleavage product;
    (b) detecting a level of any HIV or HCV RNA cleavage product(s) that are in the mixture with a detector; and
    (c) treating a patent having detectable HIV or HCV in the sample with an HIV or HCV therapy.
52. The method of statement 51, wherein detectable HIV is at least 2 copies HIV/ml sample, at least 5 copies HIV/ml sample, or at least 10 copies HIV/ml sample, or at least 20 copies HIV/ml sample, or at least 30 copies HIV/ml sample, or at least 40 copies HIV/ml sample, or at least 50 copies HIV/ml sample.
53. The method of statement 51, wherein detectable HCV is at least 2 copies HCV/ml sample, at least 5 copies HCV/ml sample, or at least 10 copies HCV/ml sample, or at least 20 copies HCV/ml sample, or at least 30 copies HCV/ml sample, or at least 40 copies HCV/ml sample, or at least 50 copies HCV/ml sample.
54. The method of any one of statements 49-52, wherein treating comprises administering to the patient one or more antiretroviral therapy (ART), combined antiretroviral therapy (cART), high active antiretroviral therapy (HAART), latency reversal agent (LRA), integrase strand transfer inhibitor (INSTI)-based regimen, regimen that includes a boosted protease inhibitor active against HIV-2 (e.g., darunavir or lopinavir), or a combination of HIV therapies.
55. The method of any one of statements 49-50 or 53, wherein treating comprises administering to the patient one or more of Daclatasir, Elbasvir-Grazoprevir, Glecaprevir-Pibrentasvir, Harvoni, Ledipasvir-Sofosbuvir, Ombitasvir-Paritaprevir-Ritonavir, Ombitasvir-Paritaprevir-Ritonavir and Dasabuvir, Peginterferon alfa-2a, Peginterferon alfa-2b, Ribavirin, Simeprevir, Sofosbuvir, Technivie, Sofosbuvir-Velpatasvir, Sofosbuvir-Velpatasvir-Voxilaprevir, Zepatier, or combinations thereof.
56. A kit comprising a package containing at least one Cas13a protein, at least one CRISPR guide RNA (crRNA), and instructions for detecting and/or quantifying HIV or HCV RNA in a sample (e.g., pursuant to the method of any of statements 1-55), where each of the CRISPR guide RNA(s) can have a sequence with about 70% or more sequence identity to any one of SEQ ID NO: 1-8, 18-25 or 26.
57. The kit of statement 56, further comprising at least one short quenched-fluorescent RNA.
58. The kit of statement 56 or 57, further comprising nuclease-free water, a buffer to regulate the pH of a solution, reaction vessel(s), and/or implements for collection of a sample from a patient.
59 The kit of statement 56, 57, or 58, further comprising a therapeutic agent for treatment of HIV or HCV infection.
60. A composition comprising one or more CRISPR guide RNA(s) comprising a sequence with at least 70% sequence identity to any one of SEQ ID NO: 1-8, 18-25 or 26.
61. The composition of statement 60, further comprising at least one Cas13a protein.

It is to be understood that while the invention has been described in conjunction with the above embodiments, that the foregoing description and examples are intended to illustrate and not limit the scope of the invention. Other aspects, advantages and modifications within the scope of the invention will be apparent to those skilled in the art to which the invention pertains.

Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

In addition, where the features or aspects of the invention are described in terms of Markush groups, those skilled in the art will recognize that the invention is also thereby described in terms of any individual member or subgroup members of the Markush group.

What is claimed is:

1. A method comprising:
   (a) incubating a sample containing RNA with a Cas13a protein and at least one CRISPR guide RNA (crRNA) for a period of time to form a RNA cleavage product; and
   (b) detecting a level of HIV or HCV RNA cleavage product with a detector,
   wherein the RNA is not reverse transcribed prior to the detecting step,
   wherein the least one crRNA is SEQ ID NOs: 1-8, 18-25 or 26.

2. The method of claim 1, further comprising a step of amplification of the RNA and/or the HIV or HCV RNA cleavage products.

3. The method of claim 1, wherein the RNA and/or the HIV or HCV RNA cleavage product are not amplified.

4. The method of claim 1, wherein the detector is a fluorescence detector, optionally a short quenched-fluorescent RNA.

5. The method of claim 1, wherein the sample is incubated with 2, 3, 4, 5, 6, 7, 8, 9, 10 or more crRNAs.

6. The method of claim 1, wherein the HIV or HCV RNA cleavage product concentration is determined using a standard curve and the level of the HIV or HCV RNA cleavage product.

7. The method of claim 1, further comprising depleting a portion of the sample prior to detecting step.

8. The method of claim 7, wherein the portion of the sample is a human nucleic acid portion.

9. The method of claim 1, further comprising treating the sample with an RNase inhibitor and/or heat before the incubating step.

10. The method of claim 1, wherein the Cas13a protein and/or crRNA is lyophilized prior to incubation with the sample.

11. A method for quantifying HIV or HCV RNA concentration comprising:
(a) incubating a sample containing RNA with a Cas13a protein and at least one CRISPR guide RNA (crRNA) for a period of time; and
(b) analyzing the sample for HIV or HCV RNA cleavage product concentration with a detector,
wherein the RNA is not reverse transcribed prior to the analyzing step,
wherein the least one crRNA is SEQ ID NOs: 1-8, 18-25 or 26.

12. The method of claim 11, wherein the HIV or HCV RNA cleavage product concentration is determined using a standard curve.

13. The method of claim 11, further comprising a step of amplification of the RNA and/or the HIV or HCV RNA cleavage product.

14. The method of claim 11, wherein the detector is a fluorescence detector, optionally a short quenched-fluorescent RNA.

15. The method of claim 11, wherein the sample is incubated with 2, 3, 4, 5, 6, 7, 8, 9, 10 or more crRNAs.

16. The method of claim 11, further comprising depleting a portion of the sample prior to the analyzing step.

17. The method of claim 11, further comprising removing RNase from the sample before the incubating step.

18. The method of claim 17, further comprising treating the sample with an RNase inhibitor and/or heat before the incubating step.

19. The method of claim 11, wherein the Cas13a protein and/or crRNA is lyophilized prior to incubation with the sample.

* * * * *

```
                              SEQUENCE LISTING

<160> NUMBER OF SEQ ID NOS: 26

<210> SEQ ID NO 1
<211> LENGTH: 49
<212> TYPE: RNA
<213> ORGANISM: Human immunodeficiency virus

<400> SEQUENCE: 1
gaccacccca aaaugaagg ggacuaaacu uuuuuuuuuu uugaagcac              49

<210> SEQ ID NO 2
<211> LENGTH: 50
<212> TYPE: RNA
<213> ORGANISM: Human immunodeficiency virus

<400> SEQUENCE: 2
gaccacccca aaaugaagg ggacuaaaac cugcuuauau gcaggaucug             50

<210> SEQ ID NO 3
<211> LENGTH: 50
<212> TYPE: RNA
<213> ORGANISM: Human immunodeficiency virus

<400> SEQUENCE: 3
gaccacccca aaaugaagg ggacuaaaac ccagagagac ccaguacagg             50

<210> SEQ ID NO 4
<211> LENGTH: 50
<212> TYPE: RNA
<213> ORGANISM: Human immunodeficiency virus

<400> SEQUENCE: 4
gaccacccca aaaugaagg ggacuaaaac ccugccauag gagaugccua             50

<210> SEQ ID NO 5
<211> LENGTH: 50
<212> TYPE: RNA
<213> ORGANISM: Human immunodeficiency virus

<400> SEQUENCE: 5
gaccacccca aaaugaagg ggacuaaaac gucuccgcuu cuuccugcca             50

<210> SEQ ID NO 6
<211> LENGTH: 50
<212> TYPE: RNA
<213> ORGANISM: Human immunodeficiency virus

<400> SEQUENCE: 6
gaccacccca aaaugaagg ggacuaaaac agcuugauga gucugacugu             50

<210> SEQ ID NO 7
<211> LENGTH: 50
<212> TYPE: RNA
<213> ORGANISM: Human immunodeficiency virus

<400> SEQUENCE: 7
gaccacccca aaaugaagg ggacuaaaac uuccuucggg ccugucgggu             50
```

<210> SEQ ID NO 8
<211> LENGTH: 50
<212> TYPE: RNA
<213> ORGANISM: Human immunodeficiency virus

<400> SEQUENCE: 8
gaccacccca aaaugaagg ggacuaaaac ggaucugucu cugucucucu          50

<210> SEQ ID NO 9
<211> LENGTH: 30
<212> TYPE: RNA
<213> ORGANISM: Human immunodeficiency virus

<400> SEQUENCE: 9
gaccacccca aaaugaagg ggacuaaaac                                30

<210> SEQ ID NO 10
<211> LENGTH: 1177
<212> TYPE: PRT
<213> ORGANISM: Leptotrichia wadei

<400> SEQUENCE: 10

```
Met Lys Ile Thr Lys Ile Asp Gly Val Ser His Tyr Lys Lys Gln Asp
1               5                   10                  15

Lys Gly Ile Leu Lys Lys Lys Trp Lys Asp Leu Asp Glu Arg Lys Gln
            20                  25                  30

Arg Glu Lys Ile Glu Ala Arg Tyr Asn Lys Gln Ile Glu Ser Lys Ile
        35                  40                  45

Tyr Lys Glu Phe Phe Arg Leu Lys Asn Lys Lys Arg Ile Glu Lys Glu
    50                  55                  60

Glu Asp Gln Asn Ile Lys Ser Leu Tyr Phe Phe Ile Lys Glu Leu Tyr
65                  70                  75                  80

Leu Asn Glu Lys Asn Glu Glu Trp Glu Leu Lys Asn Ile Asn Leu Glu
                85                  90                  95

Ile Leu Asp Asp Lys Glu Arg Val Ile Lys Gly Tyr Lys Phe Lys Glu
            100                 105                 110

Asp Val Tyr Phe Phe Lys Glu Gly Tyr Lys Glu Tyr Tyr Leu Arg Ile
        115                 120                 125

Leu Phe Asn Asn Leu Ile Glu Lys Val Gln Asn Glu Asn Arg Glu Lys
    130                 135                 140

Val Arg Lys Asn Lys Glu Phe Leu Asp Leu Lys Glu Ile Phe Lys Lys
145                 150                 155                 160

Tyr Lys Asn Arg Lys Ile Asp Leu Leu Leu Lys Ser Ile Asn Asn Asn
                165                 170                 175

Lys Ile Asn Leu Glu Tyr Lys Lys Glu Asn Val Asn Glu Glu Ile Tyr
            180                 185                 190

Gly Ile Asn Pro Thr Asn Asp Arg Glu Met Thr Phe Tyr Glu Leu Leu
        195                 200                 205

Lys Glu Ile Ile Glu Lys Lys Asp Glu Gln Lys Ser Ile Leu Glu Glu
    210                 215                 220

Lys Leu Asp Asn Phe Asp Ile Thr Asn Phe Leu Glu Asn Ile Glu Lys
225                 230                 235                 240

Ile Phe Asn Glu Glu Thr Glu Ile Asn Ile Ile Lys Gly Lys Val Leu
                245                 250                 255

Asn Glu Leu Arg Glu Tyr Ile Lys Glu Lys Glu Glu Asn Asn Ser Asp
            260                 265                 270
```

-continued

```
Asn Lys Leu Lys Gln Ile Tyr Asn Leu Glu Leu Lys Lys Tyr Ile Glu
            275                 280                 285
Asn Asn Phe Ser Tyr Lys Lys Gln Lys Ser Lys Ser Lys Asn Gly Lys
290                 295                 300
Asn Asp Tyr Leu Tyr Leu Asn Phe Leu Lys Lys Ile Met Phe Ile Glu
305                 310                 315                 320
Glu Val Asp Glu Lys Lys Glu Ile Asn Lys Glu Lys Phe Lys Asn Lys
                325                 330                 335
Ile Asn Ser Asn Phe Lys Asn Leu Phe Val Gln His Ile Leu Asp Tyr
            340                 345                 350
Gly Lys Leu Leu Tyr Tyr Lys Glu Asn Asp Glu Tyr Ile Lys Asn Thr
            355                 360                 365
Gly Gln Leu Glu Thr Lys Asp Leu Glu Tyr Ile Lys Thr Lys Glu Thr
370                 375                 380
Leu Ile Arg Lys Met Ala Val Leu Val Ser Phe Ala Ala Asn Ser Tyr
385                 390                 395                 400
Tyr Asn Leu Phe Gly Arg Val Ser Gly Asp Ile Leu Gly Thr Glu Val
                405                 410                 415
Val Lys Ser Ser Lys Thr Asn Val Ile Lys Val Gly Ser His Ile Phe
            420                 425                 430
Lys Glu Lys Met Leu Asn Tyr Phe Phe Asp Phe Glu Ile Phe Asp Ala
            435                 440                 445
Asn Lys Ile Val Glu Ile Leu Glu Ser Ile Ser Tyr Ser Ile Tyr Asn
            450                 455                 460
Val Arg Asn Gly Val Gly His Phe Asn Lys Leu Ile Leu Gly Lys Tyr
465                 470                 475                 480
Lys Lys Lys Asp Ile Asn Thr Asn Lys Arg Ile Glu Glu Asp Leu Asn
                485                 490                 495
Asn Asn Glu Glu Ile Lys Gly Tyr Phe Ile Lys Lys Arg Gly Glu Ile
                500                 505                 510
Glu Arg Lys Val Lys Glu Lys Phe Leu Ser Asn Asn Leu Gln Tyr Tyr
            515                 520                 525
Tyr Ser Lys Glu Lys Ile Glu Asn Tyr Phe Glu Val Tyr Glu Phe Glu
530                 535                 540
Ile Leu Lys Arg Lys Ile Pro Phe Ala Pro Asn Phe Lys Arg Ile Ile
545                 550                 555                 560
Lys Lys Gly Glu Asp Leu Phe Asn Asn Lys Asn Lys Lys Tyr Glu
                565                 570                 575
Tyr Phe Lys Asn Phe Asp Lys Asn Ser Ala Glu Glu Lys Lys Glu Phe
                580                 585                 590
Leu Lys Thr Arg Asn Phe Leu Leu Lys Glu Leu Tyr Tyr Asn Asn Phe
            595                 600                 605
Tyr Lys Glu Phe Leu Ser Lys Lys Glu Glu Phe Glu Lys Ile Val Leu
610                 615                 620
Glu Val Lys Glu Glu Lys Lys Ser Arg Gly Asn Ile Asn Asn Lys Lys
625                 630                 635                 640
Ser Gly Val Ser Phe Gln Ser Ile Asp Tyr Asp Thr Lys Ile Asn
                645                 650                 655
Ile Ser Asp Tyr Ile Ala Ser Ile His Lys Lys Glu Met Glu Arg Val
            660                 665                 670
Glu Lys Tyr Asn Glu Glu Lys Gln Lys Asp Thr Ala Lys Tyr Ile Arg
            675                 680                 685
Asp Phe Val Glu Glu Ile Phe Leu Thr Gly Phe Ile Asn Tyr Leu Glu
```

-continued

```
                690                 695                 700
Lys Asp Lys Arg Leu His Phe Leu Lys Glu Glu Phe Ser Ile Leu Cys
705                 710                 715                 720

Asn Asn Asn Asn Val Val Asp Phe Asn Ile Asn Ile Asn Glu Glu
                725                 730                 735

Lys Ile Lys Glu Phe Leu Lys Glu Asn Asp Ser Lys Thr Leu Asn Leu
                740                 745                 750

Tyr Leu Phe Phe Asn Met Ile Asp Ser Lys Arg Ile Ser Glu Phe Arg
                755                 760                 765

Asn Glu Leu Val Lys Tyr Lys Gln Phe Thr Lys Lys Arg Leu Asp Glu
                770                 775                 780

Glu Lys Glu Phe Leu Gly Ile Lys Ile Glu Leu Tyr Glu Thr Leu Ile
785                 790                 795                 800

Glu Phe Val Ile Leu Thr Arg Glu Lys Leu Asp Thr Lys Lys Ser Glu
                805                 810                 815

Glu Ile Asp Ala Trp Leu Val Asp Lys Leu Tyr Val Lys Asp Ser Asn
                820                 825                 830

Glu Tyr Lys Glu Tyr Glu Glu Ile Leu Lys Leu Phe Val Asp Glu Lys
                835                 840                 845

Ile Leu Ser Ser Lys Glu Ala Pro Tyr Tyr Ala Thr Asp Asn Lys Thr
850                 855                 860

Pro Ile Leu Leu Ser Asn Phe Glu Lys Thr Arg Lys Tyr Gly Thr Gln
865                 870                 875                 880

Ser Phe Leu Ser Glu Ile Gln Ser Asn Tyr Lys Tyr Ser Lys Val Glu
                885                 890                 895

Lys Glu Asn Ile Glu Asp Tyr Asn Lys Lys Glu Glu Ile Glu Gln Lys
                900                 905                 910

Lys Lys Ser Asn Ile Glu Lys Leu Gln Asp Leu Lys Val Glu Leu His
                915                 920                 925

Lys Lys Trp Glu Gln Asn Lys Ile Thr Glu Lys Glu Ile Glu Lys Tyr
                930                 935                 940

Asn Asn Thr Thr Arg Lys Ile Asn Glu Tyr Asn Tyr Leu Lys Asn Lys
945                 950                 955                 960

Glu Glu Leu Gln Asn Val Tyr Leu Leu His Glu Met Leu Ser Asp Leu
                965                 970                 975

Leu Ala Arg Asn Val Ala Phe Phe Asn Lys Trp Glu Arg Asp Phe Lys
                980                 985                 990

Phe Ile Val Ile Ala Ile Lys Gln Phe Leu Arg Glu Asn Asp Lys Glu
                995                 1000                1005

Lys Val Asn Glu Phe Leu Asn Pro Pro Asp Asn Ser Lys Gly Lys Lys
                1010                1015                1020

Val Tyr Phe Ser Val Ser Lys Tyr Lys Asn Thr Val Glu Asn Ile Asp
1025                1030                1035                1040

Gly Ile His Lys Asn Phe Met Asn Leu Ile Phe Leu Asn Asn Lys Phe
                1045                1050                1055

Met Asn Arg Lys Ile Asp Lys Met Asn Cys Ala Ile Trp Val Tyr Phe
                1060                1065                1070

Arg Asn Tyr Ile Ala His Phe Leu His Leu His Thr Lys Asn Glu Lys
                1075                1080                1085

Ile Ser Leu Ile Ser Gln Met Asn Leu Leu Ile Lys Leu Phe Ser Tyr
                1090                1095                1100

Asp Lys Lys Val Gln Asn His Ile Leu Lys Ser Thr Lys Thr Leu Leu
1105                1110                1115                1120
```

```
Glu Lys Tyr Asn Ile Gln Ile Asn Phe Glu Ile Ser Asn Asp Lys Asn
            1125                1130                1135

Glu Val Phe Lys Tyr Lys Ile Lys Asn Arg Leu Tyr Ser Lys Lys Gly
            1140                1145                1150

Lys Met Leu Gly Lys Asn Asn Lys Leu Glu Asn Glu Phe Leu Glu Asn
            1155                1160                1165

Val Lys Ala Met Leu Glu Tyr Ser Glu
            1170                1175

<210> SEQ ID NO 11
<211> LENGTH: 1285
<212> TYPE: PRT
<213> ORGANISM: Herbinix hemicellulosilytica

<400> SEQUENCE: 11

Met Lys Leu Thr Arg Arg Ile Ser Gly Asn Ser Val Asp Gln Lys
1               5                   10                  15

Ile Thr Ala Ala Phe Tyr Arg Asp Met Ser Gln Gly Leu Leu Tyr Tyr
                20                  25                  30

Asp Ser Glu Asp Asn Asp Cys Thr Asp Lys Val Ile Glu Ser Met Asp
            35                  40                  45

Phe Glu Arg Ser Trp Arg Gly Arg Ile Leu Lys Asn Gly Glu Asp Asp
    50                  55                  60

Lys Asn Pro Phe Tyr Met Phe Val Lys Gly Leu Val Gly Ser Asn Asp
65                  70                  75                  80

Lys Ile Val Cys Glu Pro Ile Asp Val Asp Ser Asp Pro Asp Asn Leu
                85                  90                  95

Asp Ile Leu Ile Asn Lys Asn Leu Thr Gly Phe Gly Arg Asn Leu Lys
            100                 105                 110

Ala Pro Asp Ser Asn Asp Thr Leu Glu Asn Leu Ile Arg Lys Ile Gln
            115                 120                 125

Ala Gly Ile Pro Glu Glu Glu Val Leu Pro Glu Leu Lys Lys Ile Lys
        130                 135                 140

Glu Met Ile Gln Lys Asp Ile Val Asn Arg Lys Glu Gln Leu Leu Lys
145                 150                 155                 160

Ser Ile Lys Asn Asn Arg Ile Pro Phe Ser Leu Glu Gly Ser Lys Leu
                165                 170                 175

Val Pro Ser Thr Lys Lys Met Lys Trp Leu Phe Lys Leu Ile Asp Val
            180                 185                 190

Pro Asn Lys Thr Phe Asn Glu Lys Met Leu Glu Lys Tyr Trp Glu Ile
            195                 200                 205

Tyr Asp Tyr Asp Lys Leu Lys Ala Asn Ile Thr Asn Arg Leu Asp Lys
    210                 215                 220

Thr Asp Lys Lys Ala Arg Ser Ile Ser Arg Ala Val Ser Glu Glu Leu
225                 230                 235                 240

Arg Glu Tyr His Lys Asn Leu Arg Thr Asn Tyr Asn Arg Phe Val Ser
                245                 250                 255

Gly Asp Arg Pro Ala Ala Gly Leu Asp Asn Gly Gly Ser Ala Lys Tyr
            260                 265                 270

Asn Pro Asp Lys Glu Glu Phe Leu Leu Phe Leu Lys Glu Val Glu Gln
            275                 280                 285

Tyr Phe Lys Lys Tyr Phe Pro Val Lys Ser Lys His Ser Asn Lys Ser
            290                 295                 300

Lys Asp Lys Ser Leu Val Asp Lys Tyr Lys Asn Tyr Cys Ser Tyr Lys
```

```
            305                 310                 315                 320
        Val Val Lys Lys Glu Val Asn Arg Ser Ile Ile Asn Gln Leu Val Ala
                        325                 330                 335
        Gly Leu Ile Gln Gln Gly Lys Leu Leu Tyr Tyr Phe Tyr Tyr Asn Asp
                        340                 345                 350
        Thr Trp Gln Glu Asp Phe Leu Asn Ser Tyr Gly Leu Ser Tyr Ile Gln
                        355                 360                 365
        Val Glu Glu Ala Phe Lys Lys Ser Val Met Thr Ser Leu Ser Trp Gly
                        370                 375                 380
        Ile Asn Arg Leu Thr Ser Phe Phe Ile Asp Asp Ser Asn Thr Val Lys
        385                 390                 395                 400
        Phe Asp Asp Ile Thr Thr Lys Ala Lys Glu Ala Ile Glu Ser Asn
                        405                 410                 415
        Tyr Phe Asn Lys Leu Arg Thr Cys Ser Arg Met Gln Asp His Phe Lys
                        420                 425                 430
        Glu Lys Leu Ala Phe Phe Tyr Pro Val Tyr Val Lys Asp Lys Lys Asp
                        435                 440                 445
        Arg Pro Asp Asp Asp Ile Glu Asn Leu Ile Val Leu Val Lys Asn Ala
        450                 455                 460
        Ile Glu Ser Val Ser Tyr Leu Arg Asn Arg Thr Phe His Phe Lys Glu
        465                 470                 475                 480
        Ser Ser Leu Leu Glu Leu Leu Lys Glu Leu Asp Asp Lys Asn Ser Gly
                        485                 490                 495
        Gln Asn Lys Ile Asp Tyr Ser Val Ala Ala Glu Phe Ile Lys Arg Asp
                        500                 505                 510
        Ile Glu Asn Leu Tyr Asp Val Phe Arg Glu Gln Ile Arg Ser Leu Gly
                        515                 520                 525
        Ile Ala Glu Tyr Tyr Lys Ala Asp Met Ile Ser Asp Cys Phe Lys Thr
                        530                 535                 540
        Cys Gly Leu Glu Phe Ala Leu Tyr Ser Pro Lys Asn Ser Leu Met Pro
        545                 550                 555                 560
        Ala Phe Lys Asn Val Tyr Lys Arg Gly Ala Asn Leu Asn Lys Ala Tyr
                        565                 570                 575
        Ile Arg Asp Lys Gly Pro Lys Glu Thr Gly Asp Gln Gly Gln Asn Ser
                        580                 585                 590
        Tyr Lys Ala Leu Glu Glu Tyr Arg Glu Leu Thr Trp Tyr Ile Glu Val
                        595                 600                 605
        Lys Asn Asn Asp Gln Ser Tyr Asn Ala Tyr Lys Asn Leu Leu Gln Leu
                        610                 615                 620
        Ile Tyr Tyr His Ala Phe Leu Pro Glu Val Arg Glu Asn Glu Ala Leu
        625                 630                 635                 640
        Ile Thr Asp Phe Ile Asn Arg Thr Lys Glu Trp Asn Arg Lys Glu Thr
                        645                 650                 655
        Glu Glu Arg Leu Asn Thr Lys Asn Asn Lys Lys His Lys Asn Phe Asp
                        660                 665                 670
        Glu Asn Asp Asp Ile Thr Val Asn Thr Tyr Arg Tyr Glu Ser Ile Pro
                        675                 680                 685
        Asp Tyr Gln Gly Glu Ser Leu Asp Asp Tyr Leu Lys Val Leu Gln Arg
                        690                 695                 700
        Lys Gln Met Ala Arg Ala Lys Glu Val Asn Glu Lys Glu Gly Asn
        705                 710                 715                 720
        Asn Asn Tyr Ile Gln Phe Ile Arg Asp Val Val Val Trp Ala Phe Gly
                        725                 730                 735
```

```
Ala Tyr Leu Glu Asn Lys Leu Lys Asn Tyr Lys Asn Glu Leu Gln Pro
            740                 745                 750

Pro Leu Ser Lys Glu Asn Ile Gly Leu Asn Asp Thr Leu Lys Glu Leu
            755                 760                 765

Phe Pro Glu Glu Lys Val Lys Ser Pro Phe Asn Ile Lys Cys Arg Phe
770                 775                 780

Ser Ile Ser Thr Phe Ile Asp Asn Lys Gly Lys Ser Thr Asp Asn Thr
785                 790                 795                 800

Ser Ala Glu Ala Val Lys Thr Asp Gly Lys Glu Asp Glu Lys Asp Lys
                805                 810                 815

Lys Asn Ile Lys Arg Lys Asp Leu Leu Cys Phe Tyr Leu Phe Leu Arg
            820                 825                 830

Leu Leu Asp Glu Asn Glu Ile Cys Lys Leu Gln His Gln Phe Ile Lys
            835                 840                 845

Tyr Arg Cys Ser Leu Lys Glu Arg Arg Phe Pro Gly Asn Arg Thr Lys
850                 855                 860

Leu Glu Lys Glu Thr Glu Leu Leu Ala Glu Leu Glu Glu Leu Met Glu
865                 870                 875                 880

Leu Val Arg Phe Thr Met Pro Ser Ile Pro Glu Ile Ser Ala Lys Ala
                885                 890                 895

Glu Ser Gly Tyr Asp Thr Met Ile Lys Lys Tyr Phe Lys Asp Phe Ile
                900                 905                 910

Glu Lys Lys Val Phe Lys Asn Pro Lys Thr Ser Asn Leu Tyr Tyr His
            915                 920                 925

Ser Asp Ser Lys Thr Pro Val Thr Arg Lys Tyr Met Ala Leu Leu Met
930                 935                 940

Arg Ser Ala Pro Leu His Leu Tyr Lys Asp Ile Phe Lys Gly Tyr Tyr
945                 950                 955                 960

Leu Ile Thr Lys Lys Glu Cys Leu Glu Tyr Ile Lys Leu Ser Asn Ile
                965                 970                 975

Ile Lys Asp Tyr Gln Asn Ser Leu Asn Glu Leu His Glu Gln Leu Glu
            980                 985                 990

Arg Ile Lys Leu Lys Ser Glu Lys Gln Asn Gly Lys Asp Ser Leu Tyr
            995                 1000                1005

Leu Asp Lys Lys Asp Phe Tyr Lys Val Lys Glu Tyr Val Glu Asn Leu
            1010                1015                1020

Glu Gln Val Ala Arg Tyr Lys His Leu Gln His Lys Ile Asn Phe Glu
1025                1030                1035                1040

Ser Leu Tyr Arg Ile Phe Arg Ile His Val Asp Ile Ala Ala Arg Met
            1045                1050                1055

Val Gly Tyr Thr Gln Asp Trp Glu Arg Asp Met His Phe Leu Phe Lys
            1060                1065                1070

Ala Leu Val Tyr Asn Gly Val Leu Glu Glu Arg Arg Phe Glu Ala Ile
            1075                1080                1085

Phe Asn Asn Asn Asp Asp Asn Asp Gly Arg Ile Val Lys Lys Ile
            1090                1095                1100

Gln Asn Asn Leu Asn Asn Lys Asn Arg Glu Leu Val Ser Met Leu Cys
1105                1110                1115                1120

Trp Asn Lys Lys Leu Asn Lys Asn Glu Phe Gly Ala Ile Ile Trp Lys
            1125                1130                1135

Arg Asn Pro Ile Ala His Leu Asn His Phe Thr Gln Thr Glu Gln Asn
            1140                1145                1150
```

```
Ser Lys Ser Ser Leu Glu Ser Leu Ile Asn Ser Leu Arg Ile Leu Leu
            1155                1160                1165

Ala Tyr Asp Arg Lys Arg Gln Asn Ala Val Thr Lys Thr Ile Asn Asp
            1170                1175                1180

Leu Leu Leu Asn Asp Tyr His Ile Arg Ile Lys Trp Glu Gly Arg Val
1185                1190                1195                1200

Asp Glu Gly Gln Ile Tyr Phe Asn Ile Lys Glu Lys Asp Ile Glu
            1205                1210                1215

Asn Glu Pro Ile Ile His Leu Lys Leu His Lys Lys Asp Cys Tyr
            1220                1225                1230

Ile Tyr Lys Asn Ser Tyr Met Phe Asp Lys Gln Lys Glu Trp Ile Cys
            1235                1240                1245

Asn Gly Ile Lys Glu Glu Val Tyr Asp Lys Ser Ile Leu Lys Cys Ile
            1250                1255                1260

Gly Asn Leu Phe Lys Phe Asp Tyr Glu Asp Lys Asn Lys Ser Ser Ala
1265                1270                1275                1280

Asn Pro Lys His Thr
            1285

<210> SEQ ID NO 12
<211> LENGTH: 1159
<212> TYPE: PRT
<213> ORGANISM: Leptotrichia buccalis

<400> SEQUENCE: 12

Met Lys Val Thr Lys Val Gly Gly Ile Ser His Lys Lys Tyr Thr Ser
1               5                   10                  15

Glu Gly Arg Leu Val Lys Ser Glu Ser Glu Glu Asn Arg Thr Asp Glu
            20                  25                  30

Arg Leu Ser Ala Leu Leu Asn Met Arg Leu Asp Met Tyr Ile Lys Asn
            35                  40                  45

Pro Ser Ser Thr Glu Thr Lys Glu Asn Gln Lys Arg Ile Gly Lys Leu
        50                  55                  60

Lys Lys Phe Phe Ser Asn Lys Met Val Tyr Leu Lys Asp Asn Thr Leu
65                  70                  75                  80

Ser Leu Lys Asn Gly Lys Lys Glu Asn Ile Asp Arg Glu Tyr Ser Glu
                85                  90                  95

Thr Asp Ile Leu Glu Ser Asp Val Arg Asp Lys Lys Asn Phe Ala Val
            100                 105                 110

Leu Lys Lys Ile Tyr Leu Asn Glu Asn Val Asn Ser Glu Glu Leu Glu
            115                 120                 125

Val Phe Arg Asn Asp Ile Lys Lys Lys Leu Asn Lys Ile Asn Ser Leu
        130                 135                 140

Lys Tyr Ser Phe Glu Lys Asn Lys Ala Asn Tyr Gln Lys Ile Asn Glu
145                 150                 155                 160

Asn Asn Ile Glu Lys Val Glu Gly Lys Ser Lys Arg Asn Ile Ile Tyr
                165                 170                 175

Asp Tyr Tyr Arg Glu Ser Ala Lys Arg Asp Ala Tyr Val Ser Asn Val
            180                 185                 190

Lys Glu Ala Phe Asp Lys Leu Tyr Lys Glu Asp Ile Ala Lys Leu
            195                 200                 205

Val Leu Glu Ile Glu Asn Leu Thr Lys Leu Lys Tyr Lys Ile Arg
        210                 215                 220

Glu Phe Tyr His Glu Ile Ile Gly Arg Lys Asn Asp Lys Glu Asn Phe
225                 230                 235                 240
```

```
Ala Lys Ile Ile Tyr Glu Glu Ile Gln Asn Val Asn Met Lys Glu
                245                 250                 255

Leu Ile Glu Lys Val Pro Asp Met Ser Glu Leu Lys Lys Ser Gln Val
                260                 265                 270

Phe Tyr Lys Tyr Leu Asp Lys Glu Glu Leu Asn Asp Lys Asn Ile
                275                 280                 285

Lys Tyr Ala Phe Cys His Phe Val Glu Ile Glu Met Ser Gln Leu Leu
                290                 295                 300

Lys Asn Tyr Val Tyr Lys Arg Leu Ser Asn Ile Ser Asn Asp Lys Ile
305                 310                 315                 320

Lys Arg Ile Phe Glu Tyr Gln Asn Leu Lys Lys Leu Ile Glu Asn Lys
                325                 330                 335

Leu Leu Asn Lys Leu Asp Thr Tyr Val Arg Asn Cys Gly Lys Tyr Asn
                340                 345                 350

Tyr Tyr Leu Gln Asp Gly Glu Ile Ala Thr Ser Asp Phe Ile Ala Arg
                355                 360                 365

Asn Arg Gln Asn Glu Ala Phe Leu Arg Asn Ile Ile Gly Val Ser Ser
                370                 375                 380

Val Ala Tyr Phe Ser Leu Arg Asn Ile Leu Glu Thr Glu Asn Glu Asn
385                 390                 395                 400

Asp Ile Thr Gly Arg Met Arg Gly Lys Thr Val Lys Asn Asn Lys Gly
                405                 410                 415

Glu Glu Lys Tyr Val Ser Gly Glu Val Asp Lys Ile Tyr Asn Glu Asn
                420                 425                 430

Lys Lys Asn Glu Val Lys Glu Asn Leu Lys Met Phe Tyr Ser Tyr Asp
                435                 440                 445

Phe Asn Met Asp Asn Lys Asn Glu Ile Glu Asp Phe Phe Ala Asn Ile
                450                 455                 460

Asp Glu Ala Ile Ser Ser Ile Arg His Gly Ile Val His Phe Asn Leu
465                 470                 475                 480

Glu Leu Glu Gly Lys Asp Ile Phe Ala Phe Lys Asn Ile Ala Pro Ser
                485                 490                 495

Glu Ile Ser Lys Lys Met Phe Gln Asn Glu Ile Asn Glu Lys Lys Leu
                500                 505                 510

Lys Leu Lys Ile Phe Arg Gln Leu Asn Ser Ala Asn Val Phe Arg Tyr
                515                 520                 525

Leu Glu Lys Tyr Lys Ile Leu Asn Tyr Leu Lys Arg Thr Arg Phe Glu
                530                 535                 540

Phe Val Asn Lys Asn Ile Pro Phe Val Pro Ser Phe Thr Lys Leu Tyr
545                 550                 555                 560

Ser Arg Ile Asp Asp Leu Lys Asn Ser Leu Gly Ile Tyr Trp Lys Thr
                565                 570                 575

Pro Lys Thr Asn Asp Asp Asn Lys Thr Lys Glu Ile Ile Asp Ala Gln
                580                 585                 590

Ile Tyr Leu Leu Lys Asn Ile Tyr Tyr Gly Glu Phe Leu Asn Tyr Phe
                595                 600                 605

Met Ser Asn Asn Gly Asn Phe Phe Glu Ile Ser Lys Glu Ile Ile Glu
                610                 615                 620

Leu Asn Lys Asn Asp Lys Arg Asn Leu Lys Thr Gly Phe Tyr Lys Leu
625                 630                 635                 640

Gln Lys Phe Glu Asp Ile Gln Glu Lys Ile Pro Lys Glu Tyr Leu Ala
                645                 650                 655
```

```
Asn Ile Gln Ser Leu Tyr Met Ile Asn Ala Gly Asn Gln Asp Glu Glu
            660                 665                 670

Glu Lys Asp Thr Tyr Ile Asp Phe Ile Gln Lys Ile Phe Leu Lys Gly
        675                 680                 685

Phe Met Thr Tyr Leu Ala Asn Asn Gly Arg Leu Ser Leu Ile Tyr Ile
        690                 695                 700

Gly Ser Asp Glu Glu Thr Asn Thr Ser Leu Ala Glu Lys Lys Gln Glu
705                 710                 715                 720

Phe Asp Lys Phe Leu Lys Lys Tyr Glu Gln Asn Asn Ile Lys Ile
            725                 730                 735

Pro Tyr Glu Ile Asn Glu Phe Leu Arg Glu Ile Lys Leu Gly Asn Ile
            740                 745                 750

Leu Lys Tyr Thr Glu Arg Leu Asn Met Phe Tyr Leu Ile Leu Lys Leu
        755                 760                 765

Leu Asn His Lys Glu Leu Thr Asn Leu Lys Gly Ser Leu Glu Lys Tyr
        770                 775                 780

Gln Ser Ala Asn Lys Glu Glu Ala Phe Ser Asp Gln Leu Glu Leu Ile
785                 790                 795                 800

Asn Leu Leu Asn Leu Asp Asn Asn Arg Val Thr Glu Asp Phe Glu Leu
            805                 810                 815

Glu Ala Asp Glu Ile Gly Lys Phe Leu Asp Phe Asn Gly Asn Lys Val
            820                 825                 830

Lys Asp Asn Lys Glu Leu Lys Lys Phe Asp Thr Asn Lys Ile Tyr Phe
        835                 840                 845

Asp Gly Glu Asn Ile Ile Lys His Arg Ala Phe Tyr Asn Ile Lys Lys
850                 855                 860

Tyr Gly Met Leu Asn Leu Leu Glu Lys Ile Ala Asp Lys Ala Gly Tyr
865                 870                 875                 880

Lys Ile Ser Ile Glu Glu Leu Lys Lys Tyr Ser Asn Lys Lys Asn Glu
            885                 890                 895

Ile Glu Lys Asn His Lys Met Gln Glu Asn Leu His Arg Lys Tyr Ala
            900                 905                 910

Arg Pro Arg Lys Asp Glu Lys Phe Thr Asp Glu Asp Tyr Glu Ser Tyr
        915                 920                 925

Lys Gln Ala Ile Glu Asn Ile Glu Glu Tyr Thr His Leu Lys Asn Lys
        930                 935                 940

Val Glu Phe Asn Glu Leu Asn Leu Leu Gln Gly Leu Leu Leu Arg Ile
945                 950                 955                 960

Leu His Arg Leu Val Gly Tyr Thr Ser Ile Trp Glu Arg Asp Leu Arg
            965                 970                 975

Phe Arg Leu Lys Gly Glu Phe Pro Glu Asn Gln Tyr Ile Glu Glu Ile
        980                 985                 990

Phe Asn Phe Glu Asn Lys Lys Asn Val Lys Tyr Lys Gly Gly Gln Ile
        995                 1000                1005

Val Glu Lys Tyr Ile Lys Phe Tyr Lys Glu Leu His Gln Asn Asp Glu
    1010                1015                1020

Val Lys Ile Asn Lys Tyr Ser Ser Ala Asn Ile Lys Val Leu Lys Gln
1025                1030                1035                1040

Glu Lys Lys Asp Leu Tyr Ile Arg Asn Tyr Ile Ala His Phe Asn Tyr
            1045                1050                1055

Ile Pro His Ala Glu Ile Ser Leu Leu Glu Val Leu Glu Asn Leu Arg
            1060                1065                1070

Lys Leu Leu Ser Tyr Asp Arg Lys Leu Lys Asn Ala Val Met Lys Ser
```

-continued

```
             1075                1080                1085
Val Val Asp Ile Leu Lys Glu Tyr Gly Phe Val Ala Thr Phe Lys Ile
         1090                1095                1100
Gly Ala Asp Lys Lys Ile Gly Ile Gln Thr Leu Glu Ser Glu Lys Ile
1105                1110                1115                1120
Val His Leu Lys Asn Leu Lys Lys Lys Leu Met Thr Asp Arg Asn
             1125                1130                1135
Ser Glu Glu Leu Cys Lys Leu Val Lys Ile Met Phe Glu Tyr Lys Met
             1140                1145                1150
Glu Glu Lys Lys Ser Glu Asn
         1155
```

<210> SEQ ID NO 13
<211> LENGTH: 1120
<212> TYPE: PRT
<213> ORGANISM: Leptotrichia seeligeri

<400> SEQUENCE: 13

```
Met Trp Ile Ser Ile Lys Thr Leu Ile His His Leu Gly Val Leu Phe
1               5                   10                  15
Phe Cys Asp Tyr Met Tyr Asn Arg Arg Glu Lys Lys Ile Ile Glu Val
             20                  25                  30
Lys Thr Met Arg Ile Thr Lys Val Glu Val Asp Arg Lys Lys Val Leu
         35                  40                  45
Ile Ser Arg Asp Lys Asn Gly Gly Lys Leu Val Tyr Glu Asn Glu Met
     50                  55                  60
Gln Asp Asn Thr Glu Gln Ile Met His His Lys Ser Ser Phe Tyr
65                  70                  75                  80
Lys Ser Val Val Asn Lys Thr Ile Cys Arg Pro Glu Gln Lys Gln Met
                 85                  90                  95
Lys Lys Leu Val His Gly Leu Leu Gln Glu Asn Ser Gln Glu Lys Ile
             100                 105                 110
Lys Val Ser Asp Val Thr Lys Leu Asn Ile Ser Asn Phe Leu Asn His
         115                 120                 125
Arg Phe Lys Lys Ser Leu Tyr Tyr Phe Pro Glu Asn Ser Pro Asp Lys
     130                 135                 140
Ser Glu Glu Tyr Arg Ile Glu Ile Asn Leu Ser Gln Leu Leu Glu Asp
145                 150                 155                 160
Ser Leu Lys Lys Gln Gln Gly Thr Phe Ile Cys Trp Glu Ser Phe Ser
                 165                 170                 175
Lys Asp Met Glu Leu Tyr Ile Asn Trp Ala Glu Asn Tyr Ile Ser Ser
             180                 185                 190
Lys Thr Lys Leu Ile Lys Lys Ser Ile Arg Asn Asn Arg Ile Gln Ser
         195                 200                 205
Thr Glu Ser Arg Ser Gly Gln Leu Met Asp Arg Tyr Met Lys Asp Ile
     210                 215                 220
Leu Asn Lys Asn Lys Pro Phe Asp Ile Gln Ser Val Ser Glu Lys Tyr
225                 230                 235                 240
Gln Leu Glu Lys Leu Thr Ser Ala Leu Lys Ala Thr Phe Lys Glu Ala
                 245                 250                 255
Lys Lys Asn Asp Lys Glu Ile Asn Tyr Lys Leu Lys Ser Thr Leu Gln
             260                 265                 270
Asn His Glu Arg Gln Ile Ile Glu Glu Leu Lys Glu Asn Ser Glu Leu
         275                 280                 285
```

```
Asn Gln Phe Asn Ile Glu Ile Arg Lys His Leu Glu Thr Tyr Phe Pro
    290                 295                 300
Ile Lys Lys Thr Asn Arg Lys Val Gly Asp Ile Arg Asn Leu Glu Ile
305                 310                 315                 320
Gly Glu Ile Gln Lys Ile Val Asn His Arg Leu Lys Asn Lys Ile Val
                    325                 330                 335
Gln Arg Ile Leu Gln Glu Gly Lys Leu Ala Ser Tyr Glu Ile Glu Ser
            340                 345                 350
Thr Val Asn Ser Asn Ser Leu Gln Lys Ile Lys Ile Glu Glu Ala Phe
        355                 360                 365
Ala Leu Lys Phe Ile Asn Ala Cys Leu Phe Ala Ser Asn Asn Leu Arg
    370                 375                 380
Asn Met Val Tyr Pro Val Cys Lys Lys Asp Ile Leu Met Ile Gly Glu
385                 390                 395                 400
Phe Lys Asn Ser Phe Lys Glu Ile Lys His Lys Lys Phe Ile Arg Gln
                    405                 410                 415
Trp Ser Gln Phe Phe Ser Gln Glu Ile Thr Val Asp Asp Ile Glu Leu
            420                 425                 430
Ala Ser Trp Gly Leu Arg Gly Ala Ile Ala Pro Ile Arg Asn Glu Ile
        435                 440                 445
Ile His Leu Lys Lys His Ser Trp Lys Lys Phe Phe Asn Asn Pro Thr
    450                 455                 460
Phe Lys Val Lys Lys Ser Lys Ile Ile Asn Gly Lys Thr Lys Asp Val
465                 470                 475                 480
Thr Ser Glu Phe Leu Tyr Lys Glu Thr Leu Phe Lys Asp Tyr Phe Tyr
                    485                 490                 495
Ser Glu Leu Asp Ser Val Pro Glu Leu Ile Ile Asn Lys Met Glu Ser
            500                 505                 510
Ser Lys Ile Leu Asp Tyr Tyr Ser Ser Asp Gln Leu Asn Gln Val Phe
        515                 520                 525
Thr Ile Pro Asn Phe Glu Leu Ser Leu Leu Thr Ser Ala Val Pro Phe
    530                 535                 540
Ala Pro Ser Phe Lys Arg Val Tyr Leu Lys Gly Phe Asp Tyr Gln Asn
545                 550                 555                 560
Gln Asp Glu Ala Gln Pro Asp Tyr Asn Leu Lys Leu Asn Ile Tyr Asn
                    565                 570                 575
Glu Lys Ala Phe Asn Ser Glu Ala Phe Gln Ala Gln Tyr Ser Leu Phe
            580                 585                 590
Lys Met Val Tyr Tyr Gln Val Phe Leu Pro Gln Phe Thr Thr Asn Asn
        595                 600                 605
Asp Leu Phe Lys Ser Ser Val Asp Phe Ile Leu Thr Leu Asn Lys Glu
    610                 615                 620
Arg Lys Gly Tyr Ala Lys Ala Phe Gln Asp Ile Arg Lys Met Asn Lys
625                 630                 635                 640
Asp Glu Lys Pro Ser Glu Tyr Met Ser Tyr Ile Gln Ser Gln Leu Met
                    645                 650                 655
Leu Tyr Gln Lys Lys Gln Glu Glu Lys Glu Lys Ile Asn His Phe Glu
            660                 665                 670
Lys Phe Ile Asn Gln Val Phe Ile Lys Gly Phe Asn Ser Phe Ile Glu
        675                 680                 685
Lys Asn Arg Leu Thr Tyr Ile Cys His Pro Thr Lys Asn Thr Val Pro
    690                 695                 700
Glu Asn Asp Asn Ile Glu Ile Pro Phe His Thr Asp Met Asp Asp Ser
```

```
                                705                     710                     715                     720
                                Asn Ile Ala Phe Trp Leu Met Cys Lys Leu Leu Asp Ala Lys Gln Leu
                                                    725                     730                     735

Ser Glu Leu Arg Asn Glu Met Ile Lys Phe Ser Cys Ser Leu Gln Ser
                                                740                     745                     750

Thr Glu Glu Ile Ser Thr Phe Thr Lys Ala Arg Glu Val Ile Gly Leu
                                                755                     760                     765

Ala Leu Leu Asn Gly Lys Gly Cys Asn Asp Trp Lys Glu Leu Phe
                                770                     775                     780

Asp Asp Lys Glu Ala Trp Lys Lys Asn Met Ser Leu Tyr Val Ser Glu
                                785                     790                     795                     800

Glu Leu Leu Gln Ser Leu Pro Tyr Thr Gln Glu Asp Gly Gln Thr Pro
                                                    805                     810                     815

Val Ile Asn Arg Ser Ile Asp Leu Val Lys Lys Tyr Gly Thr Glu Thr
                                                820                     825                     830

Ile Leu Glu Lys Leu Phe Ser Ser Asp Asp Tyr Lys Val Ser Ala
                                                835                     840                     845

Lys Asp Ile Ala Lys Leu His Glu Tyr Asp Val Thr Glu Lys Ile Ala
                                850                     855                     860

Gln Gln Glu Ser Leu His Lys Gln Trp Ile Glu Lys Pro Gly Leu Ala
                                865                     870                     875                     880

Arg Asp Ser Ala Trp Thr Lys Lys Tyr Gln Asn Val Ile Asn Asp Ile
                                                    885                     890                     895

Ser Asn Tyr Gln Trp Ala Lys Thr Lys Val Glu Leu Thr Gln Val Arg
                                                900                     905                     910

His Leu His Gln Leu Thr Ile Asp Leu Leu Ser Arg Leu Ala Gly Tyr
                                                915                     920                     925

Met Ser Ile Ala Asp Arg Asp Phe Gln Phe Ser Ser Asn Tyr Ile Leu
                                                930                     935                     940

Glu Arg Glu Asn Ser Glu Tyr Arg Val Thr Ser Trp Ile Leu Leu Ser
                                945                     950                     955                     960

Glu Asn Lys Asn Lys Asn Lys Tyr Asn Asp Tyr Glu Leu Tyr Asn Leu
                                                    965                     970                     975

Lys Asn Ala Ser Ile Lys Val Ser Ser Lys Asn Asp Pro Gln Leu Lys
                                                980                     985                     990

Val Asp Leu Lys Gln Leu Arg Leu Thr Leu Glu Tyr Leu Glu Leu Phe
                                                    995                     1000                    1005

Asp Asn Arg Leu Lys Glu Lys Arg Asn Asn Ile Ser His Phe Asn Tyr
                                                1010                    1015                    1020

Leu Asn Gly Gln Leu Gly Asn Ser Ile Leu Glu Leu Phe Asp Asp Ala
                                1025                    1030                    1035                    1040

Arg Asp Val Leu Ser Tyr Asp Arg Lys Leu Lys Asn Ala Val Ser Lys
                                                    1045                    1050                    1055

Ser Leu Lys Glu Ile Leu Ser Ser His Gly Met Glu Val Thr Phe Lys
                                                1060                    1065                    1070

Pro Leu Tyr Gln Thr Asn His His Leu Lys Ile Asp Lys Leu Gln Pro
                                                1075                    1080                    1085

Lys Lys Ile His His Leu Gly Glu Lys Ser Thr Val Ser Ser Asn Gln
                                                    1090                    1095                    1100

Val Ser Asn Glu Tyr Cys Gln Leu Val Arg Thr Leu Leu Thr Met Lys
                                1105                    1110                    1115                    1120

<210> SEQ ID NO 14
```

```
<211> LENGTH: 1154
<212> TYPE: PRT
<213> ORGANISM: Paludibacter propionicigenes

<400> SEQUENCE: 14

Met Arg Val Ser Lys Val Lys Val Lys Asp Gly Gly Lys Asp Lys Met
1               5                   10                  15

Val Leu Val His Arg Lys Thr Thr Gly Ala Gln Leu Val Tyr Ser Gly
            20                  25                  30

Gln Pro Val Ser Asn Glu Thr Ser Asn Ile Leu Pro Glu Lys Lys Arg
        35                  40                  45

Gln Ser Phe Asp Leu Ser Thr Leu Asn Lys Thr Ile Ile Lys Phe Asp
    50                  55                  60

Thr Ala Lys Lys Gln Lys Leu Asn Val Asp Gln Tyr Lys Ile Val Glu
65                  70                  75                  80

Lys Ile Phe Lys Tyr Pro Lys Gln Glu Leu Pro Lys Gln Ile Lys Ala
                85                  90                  95

Glu Glu Ile Leu Pro Phe Leu Asn His Lys Phe Gln Glu Pro Val Lys
            100                 105                 110

Tyr Trp Lys Asn Gly Lys Glu Glu Ser Phe Asn Leu Thr Leu Leu Ile
        115                 120                 125

Val Glu Ala Val Gln Ala Gln Asp Lys Arg Lys Leu Gln Pro Tyr Tyr
    130                 135                 140

Asp Trp Lys Thr Trp Tyr Ile Gln Thr Lys Ser Asp Leu Leu Lys Lys
145                 150                 155                 160

Ser Ile Glu Asn Asn Arg Ile Asp Leu Thr Glu Asn Leu Ser Lys Arg
                165                 170                 175

Lys Lys Ala Leu Leu Ala Trp Glu Thr Glu Phe Thr Ala Ser Gly Ser
            180                 185                 190

Ile Asp Leu Thr His Tyr His Lys Val Tyr Met Thr Asp Val Leu Cys
        195                 200                 205

Lys Met Leu Gln Asp Val Lys Pro Leu Thr Asp Lys Gly Lys Ile
    210                 215                 220

Asn Thr Asn Ala Tyr His Arg Gly Leu Lys Lys Ala Leu Gln Asn His
225                 230                 235                 240

Gln Pro Ala Ile Phe Gly Thr Arg Glu Val Pro Asn Glu Ala Asn Arg
                245                 250                 255

Ala Asp Asn Gln Leu Ser Ile Tyr His Leu Glu Val Val Lys Tyr Leu
            260                 265                 270

Glu His Tyr Phe Pro Ile Lys Thr Ser Lys Arg Arg Asn Thr Ala Asp
        275                 280                 285

Asp Ile Ala His Tyr Leu Lys Ala Gln Thr Leu Lys Thr Thr Ile Glu
    290                 295                 300

Lys Gln Leu Val Asn Ala Ile Arg Ala Asn Ile Ile Gln Gln Gly Lys
305                 310                 315                 320

Thr Asn His His Glu Leu Lys Ala Asp Thr Thr Ser Asn Asp Leu Ile
                325                 330                 335

Arg Ile Lys Thr Asn Glu Ala Phe Val Leu Asn Leu Thr Gly Thr Cys
            340                 345                 350

Ala Phe Ala Ala Asn Asn Ile Arg Asn Met Val Asp Asn Glu Gln Thr
        355                 360                 365

Asn Asp Ile Leu Gly Lys Gly Asp Phe Ile Lys Ser Leu Leu Lys Asp
    370                 375                 380

Asn Thr Asn Ser Gln Leu Tyr Ser Phe Phe Phe Gly Glu Gly Leu Ser
```

```
            385                 390                 395                 400
            Thr Asn Lys Ala Glu Lys Glu Thr Gln Leu Trp Gly Ile Arg Gly Ala
                            405                 410                 415
            Val Gln Gln Ile Arg Asn Asn Val Asn His Tyr Lys Lys Asp Ala Leu
                            420                 425                 430
            Lys Thr Val Phe Asn Ile Ser Asn Phe Glu Asn Pro Thr Ile Thr Asp
                            435                 440                 445
            Pro Lys Gln Gln Thr Asn Tyr Ala Asp Thr Ile Tyr Lys Ala Arg Phe
                            450                 455                 460
            Ile Asn Glu Leu Glu Lys Ile Pro Glu Ala Phe Ala Gln Gln Leu Lys
            465                 470                 475                 480
            Thr Gly Gly Ala Val Ser Tyr Thr Ile Glu Asn Leu Lys Ser Leu
                            485                 490                 495
            Leu Thr Thr Phe Gln Phe Ser Leu Cys Arg Ser Thr Ile Pro Phe Ala
                            500                 505                 510
            Pro Gly Phe Lys Lys Val Phe Asn Gly Gly Ile Asn Tyr Gln Asn Ala
                            515                 520                 525
            Lys Gln Asp Glu Ser Phe Tyr Glu Leu Met Leu Glu Gln Tyr Leu Arg
                            530                 535                 540
            Lys Glu Asn Phe Ala Glu Glu Ser Tyr Asn Ala Arg Tyr Phe Met Leu
            545                 550                 555                 560
            Lys Leu Ile Tyr Asn Asn Leu Phe Leu Pro Gly Phe Thr Thr Asp Arg
                            565                 570                 575
            Lys Ala Phe Ala Asp Ser Val Gly Phe Val Gln Met Gln Asn Lys Lys
                            580                 585                 590
            Gln Ala Glu Lys Val Asn Pro Arg Lys Lys Glu Ala Tyr Ala Phe Glu
                            595                 600                 605
            Ala Val Arg Pro Met Thr Ala Ala Asp Ser Ile Ala Asp Tyr Met Ala
                            610                 615                 620
            Tyr Val Gln Ser Glu Leu Met Gln Glu Gln Asn Lys Lys Glu Glu Lys
            625                 630                 635                 640
            Val Ala Glu Glu Thr Arg Ile Asn Phe Glu Lys Phe Val Leu Gln Val
                            645                 650                 655
            Phe Ile Lys Gly Phe Asp Ser Phe Leu Arg Ala Lys Glu Phe Asp Phe
                            660                 665                 670
            Val Gln Met Pro Gln Pro Gln Leu Thr Ala Thr Ala Ser Asn Gln Gln
                            675                 680                 685
            Lys Ala Asp Lys Leu Asn Gln Leu Glu Ala Ser Ile Thr Ala Asp Cys
                            690                 695                 700
            Lys Leu Thr Pro Gln Tyr Ala Lys Ala Asp Asp Ala Thr His Ile Ala
            705                 710                 715                 720
            Phe Tyr Val Phe Cys Lys Leu Leu Asp Ala Ala His Leu Ser Asn Leu
                            725                 730                 735
            Arg Asn Glu Leu Ile Lys Phe Arg Glu Ser Val Asn Glu Phe Lys Phe
                            740                 745                 750
            His His Leu Leu Glu Ile Ile Glu Ile Cys Leu Leu Ser Ala Asp Val
                            755                 760                 765
            Val Pro Thr Asp Tyr Arg Asp Leu Tyr Ser Ser Glu Ala Asp Cys Leu
                            770                 775                 780
            Ala Arg Leu Arg Pro Phe Ile Glu Gln Gly Ala Asp Ile Thr Asn Trp
            785                 790                 795                 800
            Ser Asp Leu Phe Val Gln Ser Asp Lys His Ser Pro Val Ile His Ala
                            805                 810                 815
```

Asn Ile Glu Leu Ser Val Lys Tyr Gly Thr Thr Lys Leu Leu Glu Gln
                820                 825                 830

Ile Ile Asn Lys Asp Thr Gln Phe Lys Thr Thr Glu Ala Asn Phe Thr
            835                 840                 845

Ala Trp Asn Thr Ala Gln Lys Ser Ile Glu Gln Leu Ile Lys Gln Arg
        850                 855                 860

Glu Asp His His Glu Gln Trp Val Lys Ala Lys Asn Ala Asp Asp Lys
865                 870                 875                 880

Glu Lys Gln Glu Arg Lys Arg Glu Lys Ser Asn Phe Ala Gln Lys Phe
                885                 890                 895

Ile Glu Lys His Gly Asp Asp Tyr Leu Asp Ile Cys Asp Tyr Ile Asn
            900                 905                 910

Thr Tyr Asn Trp Leu Asp Asn Lys Met His Phe Val His Leu Asn Arg
        915                 920                 925

Leu His Gly Leu Thr Ile Glu Leu Leu Gly Arg Met Ala Gly Phe Val
    930                 935                 940

Ala Leu Phe Asp Arg Asp Phe Gln Phe Phe Asp Glu Gln Gln Ile Ala
945                 950                 955                 960

Asp Glu Phe Lys Leu His Gly Phe Val Asn Leu His Ser Ile Asp Lys
                965                 970                 975

Lys Leu Asn Glu Val Pro Thr Lys Lys Ile Lys Glu Ile Tyr Asp Ile
            980                 985                 990

Arg Asn Lys Ile Ile Gln Ile Asn Gly Asn Lys Ile Asn Glu Ser Val
        995                 1000                1005

Arg Ala Asn Leu Ile Gln Phe Ile Ser Ser Lys Arg Asn Tyr Tyr Asn
    1010                1015                1020

Asn Ala Phe Leu His Val Ser Asn Asp Glu Ile Lys Glu Lys Gln Met
1025                1030                1035                1040

Tyr Asp Ile Arg Asn His Ile Ala His Phe Asn Tyr Leu Thr Lys Asp
                1045                1050                1055

Ala Ala Asp Phe Ser Leu Ile Asp Leu Ile Asn Glu Leu Arg Glu Leu
            1060                1065                1070

Leu His Tyr Asp Arg Lys Leu Lys Asn Ala Val Ser Lys Ala Phe Ile
    1075                1080                1085

Asp Leu Phe Asp Lys His Gly Met Ile Leu Lys Leu Lys Leu Asn Ala
1090                1095                1100

Asp His Lys Leu Lys Val Glu Ser Leu Glu Pro Lys Lys Ile Tyr His
1105                1110                1115                1120

Leu Gly Ser Ser Ala Lys Asp Lys Pro Glu Tyr Gln Tyr Cys Thr Asn
                1125                1130                1135

Gln Val Met Met Ala Tyr Cys Asn Met Cys Arg Ser Leu Leu Glu Met
            1140                1145                1150

Lys Lys

<210> SEQ ID NO 15
<211> LENGTH: 1437
<212> TYPE: PRT
<213> ORGANISM: Lachnospiraceae bacterium

<400> SEQUENCE: 15

Met Lys Ile Ser Lys Val Arg Glu Glu Asn Arg Gly Ala Lys Leu Thr
1               5                   10                  15

Val Asn Ala Lys Thr Ala Val Val Ser Glu Asn Arg Ser Gln Glu Gly
            20                  25                  30

```
Ile Leu Tyr Asn Asp Pro Ser Arg Tyr Gly Lys Ser Arg Lys Asn Asp
         35                  40                  45

Glu Asp Arg Asp Arg Tyr Ile Glu Ser Arg Leu Lys Ser Ser Gly Lys
 50                  55                  60

Leu Tyr Arg Ile Phe Asn Glu Asp Lys Asn Lys Arg Glu Thr Asp Glu
 65                  70                  75                  80

Leu Gln Trp Phe Leu Ser Glu Ile Val Lys Lys Ile Asn Arg Arg Asn
                 85                  90                  95

Gly Leu Val Leu Ser Asp Met Leu Ser Val Asp Asp Arg Ala Phe Glu
                100                 105                 110

Lys Ala Phe Glu Lys Tyr Ala Glu Leu Ser Tyr Thr Asn Arg Arg Asn
                115                 120                 125

Lys Val Ser Gly Ser Pro Ala Phe Glu Thr Cys Gly Val Asp Ala Ala
                130                 135                 140

Thr Ala Glu Arg Leu Lys Gly Ile Ile Ser Glu Thr Asn Phe Ile Asn
145                 150                 155                 160

Arg Ile Lys Asn Asn Ile Asp Asn Lys Val Ser Glu Asp Ile Ile Asp
                165                 170                 175

Arg Ile Ile Ala Lys Tyr Leu Lys Lys Ser Leu Cys Arg Glu Arg Val
                180                 185                 190

Lys Arg Gly Leu Lys Lys Leu Leu Met Asn Ala Phe Asp Leu Pro Tyr
                195                 200                 205

Ser Asp Pro Asp Ile Asp Val Gln Arg Asp Phe Ile Asp Tyr Val Leu
                210                 215                 220

Glu Asp Phe Tyr His Val Arg Ala Lys Ser Gln Val Ser Arg Ser Ile
225                 230                 235                 240

Lys Asn Met Asn Met Pro Val Gln Pro Glu Gly Asp Gly Lys Phe Ala
                245                 250                 255

Ile Thr Val Ser Lys Gly Gly Thr Glu Ser Gly Asn Lys Arg Ser Ala
                260                 265                 270

Glu Lys Glu Ala Phe Lys Lys Phe Leu Ser Asp Tyr Ala Ser Leu Asp
                275                 280                 285

Glu Arg Val Arg Asp Asp Met Leu Arg Arg Met Arg Arg Leu Val Val
                290                 295                 300

Leu Tyr Phe Tyr Gly Ser Asp Asp Ser Lys Leu Ser Asp Val Asn Glu
305                 310                 315                 320

Lys Phe Asp Val Trp Glu Asp His Ala Ala Arg Arg Val Asp Asn Arg
                325                 330                 335

Glu Phe Ile Lys Leu Pro Leu Glu Asn Lys Leu Ala Asn Gly Lys Thr
                340                 345                 350

Asp Lys Asp Ala Glu Arg Ile Arg Lys Asn Thr Val Lys Glu Leu Tyr
                355                 360                 365

Arg Asn Gln Asn Ile Gly Cys Tyr Arg Gln Ala Val Lys Ala Val Glu
370                 375                 380

Glu Asp Asn Asn Gly Arg Tyr Phe Asp Asp Lys Met Leu Asn Met Phe
385                 390                 395                 400

Phe Ile His Arg Ile Glu Tyr Gly Val Glu Lys Ile Tyr Ala Asn Leu
                405                 410                 415

Lys Gln Val Thr Glu Phe Lys Ala Arg Thr Gly Tyr Leu Ser Glu Lys
                420                 425                 430

Ile Trp Lys Asp Leu Ile Asn Tyr Ile Ser Ile Lys Tyr Ile Ala Met
                435                 440                 445
```

-continued

```
Gly Lys Ala Val Tyr Asn Tyr Ala Met Asp Glu Leu Asn Ala Ser Asp
450                 455                 460

Lys Lys Glu Ile Glu Leu Gly Lys Ile Ser Glu Glu Tyr Leu Ser Gly
465                 470                 475                 480

Ile Ser Ser Phe Asp Tyr Glu Leu Ile Lys Ala Glu Glu Met Leu Gln
                485                 490                 495

Arg Glu Thr Ala Val Tyr Val Ala Phe Ala Ala Arg His Leu Ser Ser
            500                 505                 510

Gln Thr Val Glu Leu Asp Ser Glu Asn Ser Asp Phe Leu Leu Leu Lys
                515                 520                 525

Pro Lys Gly Thr Met Asp Lys Asn Asp Lys Asn Lys Leu Ala Ser Asn
530                 535                 540

Asn Ile Leu Asn Phe Leu Lys Asp Lys Glu Thr Leu Arg Asp Thr Ile
545                 550                 555                 560

Leu Gln Tyr Phe Gly Gly His Ser Leu Trp Thr Asp Phe Pro Phe Asp
                565                 570                 575

Lys Tyr Leu Ala Gly Gly Lys Asp Asp Val Asp Phe Leu Thr Asp Leu
                580                 585                 590

Lys Asp Val Ile Tyr Ser Met Arg Asn Asp Ser Phe His Tyr Ala Thr
            595                 600                 605

Glu Asn His Asn Asn Gly Lys Trp Asn Lys Glu Leu Ile Ser Ala Met
610                 615                 620

Phe Glu His Glu Thr Glu Arg Met Thr Val Val Met Lys Asp Lys Phe
625                 630                 635                 640

Tyr Ser Asn Asn Leu Pro Met Phe Tyr Lys Asn Asp Asp Leu Lys Lys
                645                 650                 655

Leu Leu Ile Asp Leu Tyr Lys Asp Asn Val Glu Arg Ala Ser Gln Val
                660                 665                 670

Pro Ser Phe Asn Lys Val Phe Val Arg Lys Asn Phe Pro Ala Leu Val
            675                 680                 685

Arg Asp Lys Asp Asn Leu Gly Ile Glu Leu Asp Leu Lys Ala Asp Ala
690                 695                 700

Asp Lys Gly Glu Asn Glu Leu Lys Phe Tyr Asn Ala Leu Tyr Tyr Met
705                 710                 715                 720

Phe Lys Glu Ile Tyr Tyr Asn Ala Phe Leu Asn Asp Lys Asn Val Arg
                725                 730                 735

Glu Arg Phe Ile Thr Lys Ala Thr Lys Val Ala Asp Asn Tyr Asp Arg
                740                 745                 750

Asn Lys Glu Arg Asn Leu Lys Asp Arg Ile Lys Ser Ala Gly Ser Asp
            755                 760                 765

Glu Lys Lys Lys Leu Arg Glu Gln Leu Gln Asn Tyr Ile Ala Glu Asn
770                 775                 780

Asp Phe Gly Gln Arg Ile Lys Asn Ile Val Gln Val Asn Pro Asp Tyr
785                 790                 795                 800

Thr Leu Ala Gln Ile Cys Gln Leu Ile Met Thr Glu Tyr Asn Gln Gln
                805                 810                 815

Asn Asn Gly Cys Met Gln Lys Ser Ala Ala Arg Lys Asp Ile Asn
                820                 825                 830

Lys Asp Ser Tyr Gln His Tyr Lys Met Leu Leu Leu Val Asn Leu Arg
            835                 840                 845

Lys Ala Phe Leu Glu Phe Ile Lys Glu Asn Tyr Ala Phe Val Leu Lys
850                 855                 860

Pro Tyr Lys His Asp Leu Cys Asp Lys Ala Asp Phe Val Pro Asp Phe
```

-continued

```
            865                 870                 875                 880
Ala Lys Tyr Val Lys Pro Tyr Ala Gly Leu Ile Ser Arg Val Ala Gly
                        885                 890                 895

Ser Ser Glu Leu Gln Lys Trp Tyr Ile Val Ser Arg Phe Leu Ser Pro
            900                 905                 910

Ala Gln Ala Asn His Met Leu Gly Phe Leu His Ser Tyr Lys Gln Tyr
            915                 920                 925

Val Trp Asp Ile Tyr Arg Arg Ala Ser Glu Thr Gly Thr Glu Ile Asn
            930                 935                 940

His Ser Ile Ala Glu Asp Lys Ile Ala Gly Val Asp Ile Thr Asp Val
945                 950                 955                 960

Asp Ala Val Ile Asp Leu Ser Val Lys Leu Cys Gly Thr Ile Ser Ser
                        965                 970                 975

Glu Ile Ser Asp Tyr Phe Lys Asp Glu Val Tyr Ala Glu Tyr Ile
                        980                 985                 990

Ser Ser Tyr Leu Asp Phe Glu Tyr Asp Gly Gly Asn Tyr Lys Asp Ser
            995                 1000                1005

Leu Asn Arg Phe Cys Asn Ser Asp Ala Val Asn Asp Gln Lys Val Ala
            1010                1015                1020

Leu Tyr Tyr Asp Gly Glu His Pro Lys Leu Asn Arg Asn Ile Ile Leu
1025                1030                1035                1040

Ser Lys Leu Tyr Gly Glu Arg Arg Phe Leu Glu Lys Ile Thr Asp Arg
            1045                1050                1055

Val Ser Arg Ser Asp Ile Val Glu Tyr Tyr Lys Leu Lys Lys Glu Thr
            1060                1065                1070

Ser Gln Tyr Gln Thr Lys Gly Ile Phe Asp Ser Glu Asp Glu Gln Lys
            1075                1080                1085

Asn Ile Lys Lys Phe Gln Glu Met Lys Asn Ile Val Glu Phe Arg Asp
            1090                1095                1100

Leu Met Asp Tyr Ser Glu Ile Ala Asp Glu Leu Gln Gly Gln Leu Ile
1105                1110                1115                1120

Asn Trp Ile Tyr Leu Arg Glu Arg Asp Leu Met Asn Phe Gln Leu Gly
                        1125                1130                1135

Tyr His Tyr Ala Cys Leu Asn Asn Asp Ser Asn Lys Gln Ala Thr Tyr
                        1140                1145                1150

Val Thr Leu Asp Tyr Gln Gly Lys Lys Asn Arg Lys Ile Asn Gly Ala
            1155                1160                1165

Ile Leu Tyr Gln Ile Cys Ala Met Tyr Ile Asn Gly Leu Pro Leu Tyr
            1170                1175                1180

Tyr Val Asp Lys Asp Ser Ser Glu Trp Thr Val Ser Asp Gly Lys Glu
1185                1190                1195                1200

Ser Thr Gly Ala Lys Ile Gly Glu Phe Tyr Arg Tyr Ala Lys Ser Phe
            1205                1210                1215

Glu Asn Thr Ser Asp Cys Tyr Ala Ser Gly Leu Glu Ile Phe Glu Asn
            1220                1225                1230

Ile Ser Glu His Asp Asn Ile Thr Glu Leu Arg Asn Tyr Ile Glu His
            1235                1240                1245

Phe Arg Tyr Tyr Ser Ser Phe Asp Arg Ser Leu Gly Ile Tyr Ser
            1250                1255                1260

Glu Val Phe Asp Arg Phe Phe Thr Tyr Asp Leu Lys Tyr Arg Lys Asn
1265                1270                1275                1280

Val Pro Thr Ile Leu Tyr Asn Ile Leu Leu Gln His Phe Val Asn Val
            1285                1290                1295
```

Arg Phe Glu Phe Val Ser Gly Lys Lys Met Ile Gly Ile Asp Lys Lys
                1300                1305                1310

Asp Arg Lys Ile Ala Lys Glu Lys Cys Ala Arg Ile Thr Ile Arg
    1315                1320                1325

Glu Lys Asn Gly Val Tyr Ser Glu Gln Phe Thr Tyr Lys Leu Lys Asn
            1330                1335                1340

Gly Thr Val Tyr Val Asp Ala Arg Asp Lys Arg Tyr Leu Gln Ser Ile
1345                1350                1355                1360

Ile Arg Leu Leu Phe Tyr Pro Glu Lys Val Asn Met Asp Glu Met Ile
                1365                1370                1375

Glu Val Lys Glu Lys Lys Pro Ser Asp Asn Thr Gly Lys Gly
            1380                1385                1390

Tyr Ser Lys Arg Asp Arg Gln Gln Asp Arg Lys Glu Tyr Asp Lys Tyr
                1395                1400                1405

Lys Glu Lys Lys Lys Lys Glu Gly Asn Phe Leu Ser Gly Met Gly Gly
            1410                1415                1420

Asn Ile Asn Trp Asp Glu Ile Asn Ala Gln Leu Lys Asn
1425                1430                1435

<210> SEQ ID NO 16
<211> LENGTH: 1389
<212> TYPE: PRT
<213> ORGANISM: Leptotrichia shahii

<400> SEQUENCE: 16

Met Gly Asn Leu Phe Gly His Lys Arg Trp Tyr Glu Val Arg Asp Lys
1               5                   10                  15

Lys Asp Phe Lys Ile Lys Arg Lys Val Lys Val Lys Arg Asn Tyr Asp
                20                  25                  30

Gly Asn Lys Tyr Ile Leu Asn Ile Asn Glu Asn Asn Asn Lys Glu Lys
            35                  40                  45

Ile Asp Asn Asn Lys Phe Ile Arg Lys Tyr Ile Asn Tyr Lys Lys Asn
    50                  55                  60

Asp Asn Ile Leu Lys Glu Phe Thr Arg Lys Phe His Ala Gly Asn Ile
65                  70                  75                  80

Leu Phe Lys Leu Lys Gly Lys Glu Gly Ile Ile Arg Ile Glu Asn Asn
                85                  90                  95

Asp Asp Phe Leu Glu Thr Glu Glu Val Val Leu Tyr Ile Glu Ala Tyr
                100                 105                 110

Gly Lys Ser Glu Lys Leu Lys Ala Leu Gly Ile Thr Lys Lys Lys Ile
            115                 120                 125

Ile Asp Glu Ala Ile Arg Gln Gly Ile Thr Lys Asp Asp Lys Lys Ile
    130                 135                 140

Glu Ile Lys Arg Gln Glu Asn Glu Glu Glu Ile Glu Ile Asp Ile Arg
145                 150                 155                 160

Asp Glu Tyr Thr Asn Lys Thr Leu Asn Asp Cys Ser Ile Ile Leu Arg
                165                 170                 175

Ile Ile Glu Asn Asp Glu Leu Glu Thr Lys Lys Ser Ile Tyr Glu Ile
                180                 185                 190

Phe Lys Asn Ile Asn Met Ser Leu Tyr Lys Ile Ile Glu Lys Ile Ile
            195                 200                 205

Glu Asn Glu Thr Glu Lys Val Phe Glu Asn Arg Tyr Tyr Glu Glu His
    210                 215                 220

Leu Arg Glu Lys Leu Leu Lys Asp Asp Lys Ile Asp Val Ile Leu Thr

```
            225                 230                 235                 240
Asn Phe Met Glu Ile Arg Glu Lys Ile Lys Ser Asn Leu Glu Ile Leu
                245                 250                 255
Gly Phe Val Lys Phe Tyr Leu Asn Val Gly Asp Lys Lys Lys Ser
                260                 265                 270
Lys Asn Lys Lys Met Leu Val Glu Lys Ile Leu Asn Ile Asn Val Asp
                275                 280                 285
Leu Thr Val Glu Asp Ile Ala Asp Phe Val Ile Lys Glu Leu Glu Phe
                290                 295                 300
Trp Asn Ile Thr Lys Arg Ile Glu Lys Val Lys Lys Val Asn Asn Glu
305                 310                 315                 320
Phe Leu Glu Lys Arg Arg Asn Arg Thr Tyr Ile Lys Ser Tyr Val Leu
                325                 330                 335
Leu Asp Lys His Glu Lys Phe Lys Ile Glu Arg Glu Asn Lys Lys Asp
                340                 345                 350
Lys Ile Val Lys Phe Phe Val Glu Asn Ile Lys Asn Asn Ser Ile Lys
                355                 360                 365
Glu Lys Ile Glu Lys Ile Leu Ala Glu Phe Lys Ile Asp Glu Leu Ile
                370                 375                 380
Lys Lys Leu Glu Lys Glu Leu Lys Lys Gly Asn Cys Asp Thr Glu Ile
385                 390                 395                 400
Phe Gly Ile Phe Lys Lys His Tyr Lys Val Asn Phe Asp Ser Lys Lys
                405                 410                 415
Phe Ser Lys Lys Ser Asp Glu Glu Lys Glu Leu Tyr Lys Ile Ile Tyr
                420                 425                 430
Arg Tyr Leu Lys Gly Arg Ile Glu Lys Ile Leu Val Asn Glu Gln Lys
                435                 440                 445
Val Arg Leu Lys Lys Met Glu Lys Ile Glu Ile Glu Lys Ile Leu Asn
                450                 455                 460
Glu Ser Ile Leu Ser Glu Lys Ile Leu Lys Arg Val Lys Gln Tyr Thr
465                 470                 475                 480
Leu Glu His Ile Met Tyr Leu Gly Lys Leu Arg His Asn Asp Ile Asp
                485                 490                 495
Met Thr Thr Val Asn Thr Asp Asp Phe Ser Arg Leu His Ala Lys Glu
                500                 505                 510
Glu Leu Asp Leu Glu Leu Ile Thr Phe Ala Ser Thr Asn Met Glu
                515                 520                 525
Leu Asn Lys Ile Phe Ser Arg Glu Asn Ile Asn Asn Asp Glu Asn Ile
                530                 535                 540
Asp Phe Phe Gly Gly Asp Arg Glu Lys Asn Tyr Val Leu Asp Lys Lys
545                 550                 555                 560
Ile Leu Asn Ser Lys Ile Lys Ile Ile Arg Asp Leu Asp Phe Ile Asp
                565                 570                 575
Asn Lys Asn Asn Ile Thr Asn Asn Phe Ile Arg Lys Phe Thr Lys Ile
                580                 585                 590
Gly Thr Asn Glu Arg Asn Arg Ile Leu His Ala Ile Ser Lys Glu Arg
                595                 600                 605
Asp Leu Gln Gly Thr Gln Asp Asp Tyr Asn Lys Val Ile Asn Ile Ile
                610                 615                 620
Gln Asn Leu Lys Ile Ser Asp Glu Glu Val Ser Lys Ala Leu Asn Leu
625                 630                 635                 640
Asp Val Val Phe Lys Asp Lys Lys Asn Ile Ile Thr Lys Ile Asn Asp
                645                 650                 655
```

-continued

Ile Lys Ile Ser Glu Glu Asn Asn Asp Ile Lys Tyr Leu Pro Ser
          660                 665                 670

Phe Ser Lys Val Leu Pro Glu Ile Leu Asn Leu Tyr Arg Asn Asn Pro
          675                 680                 685

Lys Asn Glu Pro Phe Asp Thr Ile Glu Thr Lys Ile Val Leu Asn
    690                 695                 700

Ala Leu Ile Tyr Val Asn Lys Glu Leu Tyr Lys Lys Leu Ile Leu Glu
705                 710                 715                 720

Asp Asp Leu Glu Glu Asn Glu Ser Lys Asn Ile Phe Leu Gln Glu Leu
                725                 730                 735

Lys Lys Thr Leu Gly Asn Ile Asp Glu Ile Asp Glu Asn Ile Ile Glu
          740                 745                 750

Asn Tyr Tyr Lys Asn Ala Gln Ile Ser Ala Ser Lys Gly Asn Asn Lys
    755                 760                 765

Ala Ile Lys Lys Tyr Gln Lys Lys Val Ile Glu Cys Tyr Ile Gly Tyr
770                 775                 780

Leu Arg Lys Asn Tyr Glu Glu Leu Phe Asp Phe Ser Asp Phe Lys Met
785                 790                 795                 800

Asn Ile Gln Glu Ile Lys Lys Gln Ile Lys Asp Ile Asn Asp Asn Lys
                805                 810                 815

Thr Tyr Glu Arg Ile Thr Val Lys Thr Ser Asp Lys Thr Ile Val Ile
          820                 825                 830

Asn Asp Asp Phe Glu Tyr Ile Ile Ser Ile Phe Ala Leu Leu Asn Ser
    835                 840                 845

Asn Ala Val Ile Asn Lys Ile Arg Asn Arg Phe Ala Thr Ser Val
850                 855                 860

Trp Leu Asn Thr Ser Glu Tyr Gln Asn Ile Ile Asp Ile Leu Asp Glu
865                 870                 875                 880

Ile Met Gln Leu Asn Thr Leu Arg Asn Glu Cys Ile Thr Glu Asn Trp
                885                 890                 895

Asn Leu Asn Leu Glu Glu Phe Ile Gln Lys Met Lys Glu Ile Glu Lys
          900                 905                 910

Asp Phe Asp Asp Phe Lys Ile Gln Thr Lys Lys Glu Ile Phe Asn Asn
    915                 920                 925

Tyr Tyr Glu Asp Ile Lys Asn Asn Ile Leu Thr Glu Phe Lys Asp Asp
    930                 935                 940

Ile Asn Gly Cys Asp Val Leu Glu Lys Lys Leu Glu Lys Ile Val Ile
945                 950                 955                 960

Phe Asp Asp Glu Thr Lys Phe Glu Ile Asp Lys Lys Ser Asn Ile Leu
                965                 970                 975

Gln Asp Glu Gln Arg Lys Leu Ser Asn Ile Asn Lys Lys Asp Leu Lys
          980                 985                 990

Lys Lys Val Asp Gln Tyr Ile Lys Asp Lys Asp Gln Glu Ile Lys Ser
          995                 1000                1005

Lys Ile Leu Cys Arg Ile Ile Phe Asn Ser Asp Phe Leu Lys Lys Tyr
    1010                1015                1020

Lys Lys Glu Ile Asp Asn Leu Ile Glu Asp Met Glu Ser Glu Asn Glu
1025                1030                1035                1040

Asn Lys Phe Gln Glu Ile Tyr Tyr Pro Lys Glu Arg Lys Asn Glu Leu
                1045                1050                1055

Tyr Ile Tyr Lys Lys Asn Leu Phe Leu Asn Ile Gly Asn Pro Asn Phe
          1060                1065                1070

```
Asp Lys Ile Tyr Gly Leu Ile Ser Asn Asp Ile Lys Met Ala Asp Ala
        1075                1080                1085

Lys Phe Leu Phe Asn Ile Asp Gly Lys Asn Ile Arg Lys Asn Lys Ile
        1090                1095                1100

Ser Glu Ile Asp Ala Ile Leu Lys Asn Leu Asn Asp Lys Leu Asn Gly
1105                1110                1115                1120

Tyr Ser Lys Glu Tyr Lys Glu Lys Tyr Ile Lys Lys Leu Lys Glu Asn
        1125                1130                1135

Asp Asp Phe Phe Ala Lys Asn Ile Gln Asn Lys Asn Tyr Lys Ser Phe
        1140                1145                1150

Glu Lys Asp Tyr Asn Arg Val Ser Glu Tyr Lys Lys Ile Arg Asp Leu
        1155                1160                1165

Val Glu Phe Asn Tyr Leu Asn Lys Ile Glu Ser Tyr Leu Ile Asp Ile
        1170                1175                1180

Asn Trp Lys Leu Ala Ile Gln Met Ala Arg Phe Glu Arg Asp Met His
1185                1190                1195                1200

Tyr Ile Val Asn Gly Leu Arg Glu Leu Gly Ile Ile Lys Leu Ser Gly
        1205                1210                1215

Tyr Asn Thr Gly Ile Ser Arg Ala Tyr Pro Lys Arg Asn Gly Ser Asp
        1220                1225                1230

Gly Phe Tyr Thr Thr Thr Ala Tyr Tyr Lys Phe Phe Asp Glu Glu Ser
        1235                1240                1245

Tyr Lys Lys Phe Glu Lys Ile Cys Tyr Gly Phe Gly Ile Asp Leu Ser
        1250                1255                1260

Glu Asn Ser Glu Ile Asn Lys Pro Glu Asn Glu Ser Ile Arg Asn Tyr
1265                1270                1275                1280

Ile Ser His Phe Tyr Ile Val Arg Asn Pro Phe Ala Asp Tyr Ser Ile
        1285                1290                1295

Ala Glu Gln Ile Asp Arg Val Ser Asn Leu Leu Ser Tyr Ser Thr Arg
        1300                1305                1310

Tyr Asn Asn Ser Thr Tyr Ala Ser Val Phe Glu Val Phe Lys Lys Asp
        1315                1320                1325

Val Asn Leu Asp Tyr Asp Glu Leu Lys Lys Lys Phe Lys Leu Ile Gly
        1330                1335                1340

Asn Asn Asp Ile Leu Glu Arg Leu Met Lys Pro Lys Lys Val Ser Val
1345                1350                1355                1360

Leu Glu Leu Glu Ser Tyr Asn Ser Asp Tyr Ile Lys Asn Leu Ile Ile
        1365                1370                1375

Glu Leu Leu Thr Lys Ile Glu Asn Thr Asn Asp Thr Leu
        1380                1385

<210> SEQ ID NO 17
<211> LENGTH: 1159
<212> TYPE: PRT
<213> ORGANISM: Leptotrichia buccalis

<400> SEQUENCE: 17

Met Lys Val Thr Lys Val Gly Gly Ile Ser His Lys Lys Tyr Thr Ser
1               5                   10                  15

Glu Gly Arg Leu Val Lys Ser Glu Ser Glu Glu Asn Arg Thr Asp Glu
            20                  25                  30

Arg Leu Ser Ala Leu Leu Asn Met Arg Leu Asp Met Tyr Ile Lys Asn
        35                  40                  45

Pro Ser Ser Thr Glu Thr Lys Glu Asn Gln Lys Arg Ile Gly Lys Leu
    50                  55                  60
```

```
Lys Lys Phe Phe Ser Asn Lys Met Val Tyr Leu Lys Asp Asn Thr Leu
 65                  70                  75                  80

Ser Leu Lys Asn Gly Lys Lys Glu Asn Ile Asp Arg Glu Tyr Ser Glu
                 85                  90                  95

Thr Asp Ile Leu Glu Ser Asp Val Arg Asp Lys Lys Asn Phe Ala Val
            100                 105                 110

Leu Lys Lys Ile Tyr Leu Asn Glu Asn Val Asn Ser Glu Glu Leu Glu
            115                 120                 125

Val Phe Arg Asn Asp Ile Lys Lys Leu Asn Lys Ile Asn Ser Leu
130                 135                 140

Lys Tyr Ser Phe Glu Lys Asn Lys Ala Asn Tyr Gln Lys Ile Asn Glu
145                 150                 155                 160

Asn Asn Ile Glu Lys Val Glu Gly Lys Ser Lys Arg Asn Ile Ile Tyr
                165                 170                 175

Asp Tyr Tyr Arg Glu Ser Ala Lys Arg Asp Ala Tyr Val Ser Asn Val
            180                 185                 190

Lys Glu Ala Phe Asp Lys Leu Tyr Lys Glu Glu Asp Ile Ala Lys Leu
            195                 200                 205

Val Leu Glu Ile Glu Asn Leu Thr Lys Leu Glu Lys Tyr Lys Ile Arg
210                 215                 220

Glu Phe Tyr His Glu Ile Ile Gly Arg Lys Asn Asp Lys Glu Asn Phe
225                 230                 235                 240

Ala Lys Ile Ile Tyr Glu Glu Ile Gln Asn Val Asn Asn Met Lys Glu
                245                 250                 255

Leu Ile Glu Lys Val Pro Asp Met Ser Glu Leu Lys Lys Ser Gln Val
            260                 265                 270

Phe Tyr Lys Tyr Tyr Leu Asp Lys Glu Glu Leu Asn Asp Lys Asn Ile
            275                 280                 285

Lys Tyr Ala Phe Cys His Phe Val Glu Ile Glu Met Ser Gln Leu Leu
            290                 295                 300

Lys Asn Tyr Val Tyr Lys Arg Leu Ser Asn Ile Ser Asn Asp Lys Ile
305                 310                 315                 320

Lys Arg Ile Phe Glu Tyr Gln Asn Leu Lys Lys Leu Ile Glu Asn Lys
                325                 330                 335

Leu Leu Asn Lys Leu Asp Thr Tyr Val Arg Asn Cys Gly Lys Tyr Asn
            340                 345                 350

Tyr Tyr Leu Gln Asp Gly Glu Ile Ala Thr Ser Asp Phe Ile Ala Arg
            355                 360                 365

Asn Arg Gln Asn Glu Ala Phe Leu Arg Asn Ile Ile Gly Val Ser Ser
370                 375                 380

Val Ala Tyr Phe Ser Leu Arg Asn Ile Leu Glu Thr Glu Asn Glu Asn
385                 390                 395                 400

Asp Ile Thr Gly Arg Met Arg Gly Lys Thr Val Lys Asn Asn Lys Gly
            405                 410                 415

Glu Glu Lys Tyr Val Ser Gly Glu Val Asp Lys Ile Tyr Asn Glu Asn
            420                 425                 430

Lys Lys Asn Glu Val Lys Glu Asn Leu Lys Met Phe Tyr Ser Tyr Asp
            435                 440                 445

Phe Asn Met Asp Asn Lys Asn Glu Ile Glu Asp Phe Phe Ala Asn Ile
            450                 455                 460

Asp Glu Ala Ile Ser Ser Ile Arg His Gly Ile Val His Phe Asn Leu
465                 470                 475                 480
```

```
Glu Leu Glu Gly Lys Asp Ile Phe Ala Phe Lys Asn Ile Ala Pro Ser
                    485                 490                 495

Glu Ile Ser Lys Lys Met Phe Gln Asn Glu Ile Asn Glu Lys Lys Leu
            500                 505                 510

Lys Leu Lys Ile Phe Arg Gln Leu Asn Ser Ala Asn Val Phe Arg Tyr
            515                 520                 525

Leu Glu Lys Tyr Lys Ile Leu Asn Tyr Leu Lys Arg Thr Arg Phe Glu
        530                 535                 540

Phe Val Asn Lys Asn Ile Pro Phe Val Pro Ser Phe Thr Lys Leu Tyr
545                 550                 555                 560

Ser Arg Ile Asp Asp Leu Lys Asn Ser Leu Gly Ile Tyr Trp Lys Thr
                565                 570                 575

Pro Lys Thr Asn Asp Asp Asn Lys Thr Lys Glu Ile Ile Asp Ala Gln
            580                 585                 590

Ile Tyr Leu Leu Lys Asn Ile Tyr Tyr Gly Glu Phe Leu Asn Tyr Phe
        595                 600                 605

Met Ser Asn Asn Gly Asn Phe Phe Glu Ile Ser Lys Glu Ile Ile Glu
610                 615                 620

Leu Asn Lys Asn Asp Lys Arg Asn Leu Lys Thr Gly Phe Tyr Lys Leu
625                 630                 635                 640

Gln Lys Phe Glu Asp Ile Gln Glu Lys Ile Pro Lys Glu Tyr Leu Ala
                645                 650                 655

Asn Ile Gln Ser Leu Tyr Met Ile Asn Ala Gly Asn Gln Asp Glu Glu
            660                 665                 670

Glu Lys Asp Thr Tyr Ile Asp Phe Ile Gln Lys Ile Phe Leu Lys Gly
        675                 680                 685

Phe Met Thr Tyr Leu Ala Asn Asn Gly Arg Leu Ser Leu Ile Tyr Ile
690                 695                 700

Gly Ser Asp Glu Glu Thr Asn Thr Ser Leu Ala Glu Lys Lys Gln Glu
705                 710                 715                 720

Phe Asp Lys Phe Leu Lys Lys Tyr Glu Gln Asn Asn Ile Lys Ile
                725                 730                 735

Pro Tyr Glu Ile Asn Glu Phe Leu Arg Glu Ile Lys Leu Gly Asn Ile
            740                 745                 750

Leu Lys Tyr Thr Glu Arg Leu Asn Met Phe Tyr Leu Ile Leu Lys Leu
        755                 760                 765

Leu Asn His Lys Glu Leu Thr Asn Leu Lys Gly Ser Leu Glu Lys Tyr
770                 775                 780

Gln Ser Ala Asn Lys Glu Glu Ala Phe Ser Asp Gln Leu Glu Leu Ile
785                 790                 795                 800

Asn Leu Leu Asn Leu Asp Asn Asn Arg Val Thr Glu Asp Phe Glu Leu
                805                 810                 815

Glu Ala Asp Glu Ile Gly Lys Phe Leu Asp Phe Asn Gly Asn Lys Val
            820                 825                 830

Lys Asp Asn Lys Glu Leu Lys Lys Phe Asp Thr Asn Lys Ile Tyr Phe
        835                 840                 845

Asp Gly Glu Asn Ile Ile Lys His Arg Ala Phe Tyr Asn Ile Lys Lys
850                 855                 860

Tyr Gly Met Leu Asn Leu Leu Glu Lys Ile Ala Asp Lys Ala Gly Tyr
865                 870                 875                 880

Lys Ile Ser Ile Glu Glu Leu Lys Lys Tyr Ser Asn Lys Lys Asn Glu
                885                 890                 895

Ile Glu Lys Asn His Lys Met Gln Glu Asn Leu His Arg Lys Tyr Ala
```

-continued

```
                900             905             910
Arg Pro Arg Lys Asp Glu Lys Phe Thr Asp Glu Asp Tyr Glu Ser Tyr
            915                 920             925

Lys Gln Ala Ile Glu Asn Ile Glu Glu Tyr Thr His Leu Lys Asn Lys
            930                 935             940

Val Glu Phe Asn Glu Leu Asn Leu Leu Gln Gly Leu Leu Leu Arg Ile
945                 950             955                 960

Leu His Arg Leu Val Gly Tyr Thr Ser Ile Trp Glu Arg Asp Leu Arg
                965             970                 975

Phe Arg Leu Lys Gly Glu Phe Pro Glu Asn Gln Tyr Ile Glu Glu Ile
            980                 985             990

Phe Asn Phe Glu Asn Lys Lys Asn Val Lys Tyr Lys Gly Gly Gln Ile
            995                 1000            1005

Val Glu Lys Tyr Ile Lys Phe Tyr Lys Glu Leu His Gln Asn Asp Glu
            1010                1015            1020

Val Lys Ile Asn Lys Tyr Ser Ser Ala Asn Ile Lys Val Leu Lys Gln
1025                1030            1035                1040

Glu Lys Lys Asp Leu Tyr Ile Arg Asn Tyr Ile Ala His Phe Asn Tyr
            1045                1050            1055

Ile Pro His Ala Glu Ile Ser Leu Leu Glu Val Leu Glu Asn Leu Arg
            1060                1065            1070

Lys Leu Leu Ser Tyr Asp Arg Lys Leu Lys Asn Ala Val Met Lys Ser
            1075                1080            1085

Val Val Asp Ile Leu Lys Glu Tyr Gly Phe Val Ala Thr Phe Lys Ile
            1090                1095            1100

Gly Ala Asp Lys Lys Ile Gly Ile Gln Thr Leu Glu Ser Glu Lys Ile
1105                1110            1115                1120

Val His Leu Lys Asn Leu Lys Lys Lys Leu Met Thr Asp Arg Asn
            1125                1130            1135

Ser Glu Glu Leu Cys Lys Leu Val Lys Ile Met Phe Gly Tyr Lys Met
            1140                1145            1150

Glu Glu Lys Lys Ser Glu Asn
            1155

<210> SEQ ID NO 18
<211> LENGTH: 50
<212> TYPE: RNA
<213> ORGANISM: Hepatitis C virus

<400> SEQUENCE: 18
gaccacccca aaaugaagg ggacuaaaac guguacucac cgguuccgca                50

<210> SEQ ID NO 19
<211> LENGTH: 50
<212> TYPE: RNA
<213> ORGANISM: Hepatitis C virus

<400> SEQUENCE: 19
gaccacccca aaaugaagg ggacuaaaac cccuaucagg caguaccaca                50

<210> SEQ ID NO 20
<211> LENGTH: 50
<212> TYPE: RNA
<213> ORGANISM: Hepatitis C virus

<400> SEQUENCE: 20
gaccacccca aaaugaagg ggacuaaaac accgggugagg uucccuguug               50
```

```
<210> SEQ ID NO 21
<211> LENGTH: 50
<212> TYPE: RNA
<213> ORGANISM: Hepatitis C virus

<400> SEQUENCE: 21
gaccacccca aaaaugaagg ggacuaaaac gggcgaccag uucaucauca          50

<210> SEQ ID NO 22
<211> LENGTH: 50
<212> TYPE: RNA
<213> ORGANISM: Hepatitis C virus

<400> SEQUENCE: 22
gaccacccca aaaaugaagg ggacuaaaac gacgaugacc uucuucucca          50

<210> SEQ ID NO 23
<211> LENGTH: 50
<212> TYPE: RNA
<213> ORGANISM: Hepatitis C virus

<400> SEQUENCE: 23
gaccacccca aaaaugaagg ggacuaaaac uuccacugcc aguuggagca          50

<210> SEQ ID NO 24
<211> LENGTH: 50
<212> TYPE: RNA
<213> ORGANISM: Hepatitis C virus

<400> SEQUENCE: 24
gaccacccca aaaaugaagg ggacuaaaac guucauccau uggaccgcgc          50

<210> SEQ ID NO 25
<211> LENGTH: 50
<212> TYPE: RNA
<213> ORGANISM: Hepatitis C virus

<400> SEQUENCE: 25
gaccacccca aaaaugaagg ggacuaaaac ggcucgagaa aguccagaac          50

<210> SEQ ID NO 26
<211> LENGTH: 50
<212> TYPE: RNA
<213> ORGANISM: Hepatitis C virus

<400> SEQUENCE: 26
gaccacccca aaaaugaagg ggacuaaaac ucugcagaga gaccaguuac          50
```

UNITED STATES PATENT AND TRADEMARK OFFICE
CERTIFICATE OF CORRECTION

| | | |
|---|---|---|
| PATENT NO. | : 12,215,377 B2 | Page 1 of 1 |
| APPLICATION NO. | : 17/273752 | |
| DATED | : February 4, 2025 | |
| INVENTOR(S) | : Fozouni et al. | |

It is certified that error appears in the above-identified patent and that said Letters Patent is hereby corrected as shown below:

In the Specification

In Column 1, Line 18, before "R61 AI140465", delete "DE"

Signed and Sealed this
Eighteenth Day of March, 2025

Coke Morgan Stewart
*Acting Director of the United States Patent and Trademark Office*